United States Patent [19]
Ausich et al.

[11] Patent Number: 5,656,472
[45] Date of Patent: Aug. 12, 1997

[54] BETA-CAROTENE BIOSYNTHESIS IN GENETICALLY ENGINEERED HOSTS

[75] Inventors: Rodney L. Ausich, Glen Ellyn; Friedhelm Luetke Brinkhaus, Lisle; Indrani Mukharji, Evanston; John Proffitt, Oak Park; James Yarger, St. Charles; Huei-Che Bill Yen, Naperville, all of Ill.

[73] Assignee: Amoco Corporation, Chicago, Ill.

[21] Appl. No.: 473,512

[22] Filed: Jun. 7, 1995

Related U.S. Application Data

[60] Division of Ser. No. 95,726, Jul. 21, 1993, Pat. No. 5,530,188, which is a continuation-in-part of Ser. No. 662,921, Feb. 28, 1991, abandoned, which is a continuation-in-part of Ser. No. 562,674, Aug. 3, 1990, abandoned, which is a continuation-in-part of Ser. No. 525,551, May 18, 1990, abandoned, which is a continuation-in-part of Ser. No. 487,613, Mar. 2, 1990, abandoned.

[51] Int. Cl.$^6$ .................. C12N 1/20; C12N 15/00; C07H 21/02; C07H 21/04
[52] U.S. Cl. .......... 435/193; 536/23.1; 536/23.2; 536/23.6; 435/69.1; 435/67; 435/189; 435/252.33; 435/252.2; 435/320.1; 435/847; 435/252.3
[58] Field of Search ............ 435/67, 69.1, 69.9, 435/252.3, 252.33, 254.1; 536/23.1, 23.2, 23.6; 930/240; 935/14, 29, 69, 72, 73; 530/350

[56] References Cited

U.S. PATENT DOCUMENTS

| | | | |
|---|---|---|---|
| 3,833,350 | 9/1974 | Cooke et al. | 426/268 |
| 4,769,061 | 9/1988 | Comai | 435/172.3 |
| 5,034,323 | 7/1991 | Jorgensen et al. | 435/172.3 |
| 5,349,126 | 9/1994 | Chappell et al. | 800/205 |
| 5,429,939 | 7/1995 | Misawa et al. | 435/67 |

FOREIGN PATENT DOCUMENTS 0393690  10/1990  European Pat. Off.

OTHER PUBLICATIONS

Straub, "Key to Carotenoids", Pfander et al., eds. (Birkhauser Verlag: 1987).
Nelson et al., *Mol. Cell. Biol.*, 9: 1271–1276 (1989).
Tuveson et al., *J. Bacteriol.*, 170(10):4675–4680 (1988).
Perry et al., *J. Bacteriol.*, 168(2):607–612 (1993).
Romer et al., *Biochem. Biophys. Res. Commun.*, 196(3):1414–1421 (1993).
Cunningham et al., *FEBS Lett.*, 328:130–138 (1993).
Armstrong et al.,*Mol. Gen. Genet.*, 216:254–265 (1989).
Bryant, *Plants Today* 1:23–28 (1988).
Bartels et al., *Weed Sci.*, 26:198–203 (1978).
Sagar et al.,*Plant Physiol.*, 88:340–347 (1988).
Bartley et al., *J. Biol. Chem.*, 264:13109–13113 (1989).
Armstrong et al., *J. Biol. Chem.*, 265:8329–8338 (1990).
Bartley et al., *J. Biol. Chem.*, 265:16020–16024 (1990).
Schmidt et al., *European J.Biol. Chem.*, 184:375–378 (1989).
Thiry, *J. Gen. Microbio.*, 130:1623–1631 (1984).
Schmidt et al., *Gene*, 91:113–117 (1990).
Armstrong et al., *Proc. Natl. Acad. Sci. USA*, 87:9975–9979 (1990).
Tichy et al., *J. Bacteriol.*, 171:4914–4922 (1989).
Misawa et al., *J. Bacteriol.*, 172:6704–6712 (1990).
Giuliano et al., *Mol. Gen. Genet.*, 213:78–83 (1988).
Armstrong et al., *Mol. Gen. Genet.*, 216:254–268 )1989).
Young et al., *Mol. Gen. Genet.*, 218:1–12 (1989).

(List continued on next page.)

*Primary Examiner*—Robert A. Wax
*Assistant Examiner*—Tekchand Saidha
*Attorney, Agent, or Firm*—Welsh & Katz, Ltd.

[57] ABSTRACT

DNA segments encoding the *Erwinia herbicola* enzymes geranylgeranyl pyrophosphate (GGPP) synthase, phytoene synthase, phytoene dehydrogenase-4H and lycopene cyclase, vectors containing those DNA segments, host cells containing the vectors and methods for producing those enzymes and beta-carotene by recombinant DNA technology in transformed host organisms are disclosed.

15 Claims, 33 Drawing Sheets

OTHER PUBLICATIONS

Schnurr et al., *FEMS Microbio. Lett.*, 78:157–162 (1991).
Bennetzen et al., *J. Cell. Biochem.*, 12C:246 (1988).
Botterman et al., *Trends in Genet.*, 4:219–222 (1988).
Hinchee et al., *Bio/Technology*, 6:915–922 (1988).
Pemberton et al., *Cur. Microbio.*, 15:67–71 (1987).
Daub et al., *Phytopathology*, 79:180–185 (1989).
Ben–Amotz et al., *J. Phycology*, 23:176–181 (1987).
Chamovitz et al., *Zeitschrift fur Naturforschung*, 45c:482–486 (1990).

Carotenoid Biosynthesis Scheme

```
Bgl II
AGATCTAAAGGCACAGGTCTCATGCTTCGCACAATGTAAAACTGCTTCAGAACCTGGCG            60

Hpa I
AGAGCTATCCGGCGGGTCTAACGGTTAACTGATACTAAAAGACAATTCAGCGGGTAACCTT         120

Nru I
GCAATGGTGAGTGGCAGTAAAGCGGGGCGTTTCGCCTCATCGCGAAATAGAGGTAATGAGA         180
        MetValSerGlySerLysAlaGlyValSerProHisArgGluIleGluValMetArg

CAATCCATTGACGATCACCTGGCCTGTTACCTGAAAACCGACAGCCAGGATATCGTC             240
GlnSerIleAspAspHisLeuAlaGlyLeuLeuProGluThrAspSerGlnAspIleVal

Bam HI
AGCCTTGCGATGCGTGAAGGCGTCATGGCACCCGGTAAAACGGATCCGTCCGCTGCTGATG        300
SerLeuAlaMetArgGluGlyValMetAlaProGlyLysArgIleArgProLeuLeuMet

CTGCTGGCCGCCCGCGACCTCCGCGACTATGCCAGGGCAGTATGCCTACGCTGCTCGATCTCCGCC   360
LeuLeuAlaAlaArgAspLeuArgAspTyrGlnGlySerMetProThrLeuLeuAspLeuAla

TGCGCCGTTGAACTGACCATACCGCGTCGATGCTCGACGACATGCCCTGCATGGAC             420
CysAlaValGluLeuThrHisThrAlaSerLeuMetLeuAspAspMetProCysMetAsp

FIG. 2A
```

ACCGGCGAGCTGGCGGCGCGGGTCAGCTGGTCAGCCCACTACCCACAAAAATTTGGTGAGAGCGTGGCG  480
AsnAlaGluLeuArgArgGlyGlnProThrThrHisLysLysPheGlyGluSerValAla

ATCCTTGCCTCCGTTGGCTGCTCTCTAAAGCCTTTGGTCTTGATCGCCGCCACCGGCGAT  540
IleLeuAlaSerValGlyLeuLeuSerLysAlaPheGlyLeuIleAlaAlaThrGlyAsp

CTGCCCGGGGAGAGGGGTGCCCAGGCGGGTCAACGAGCTCTACCGGCTGTGCAG  600
LeuProGlyGluArgArgAlaGlnAlaValAlaAsnGluLeuSerThrAlaValGlyLeuGln

GGCCTGGTACTGGGGCCAGTTTCGGCGATCTTAACGATGCCGCCCTCGACCGTACCCCCTGAC  660
GlyLeuValLeuGlyGlnPheArgAspLeuAsnAspAlaAlaLeuAspArgThrProAsp

GCTATCCTTCAGCACCAACCACCTCAAGACCGGCATTCTGTTCAGGCGGATGCTGCAGATC  720
AlaIleLeuSerThrAsnHisLeuLysThrGlyIleLeuPheSerAlaMetLeuGlnIle

GTCGCCATTGCTTCCGCCTGCTTCGCCGAGCACGGCGAGAGACGCTGCACGCCTTCGCCCTC  780
ValAlaIleAlaSerAlaSerSerProSerThrArgGluThrLeuHisAlaPheAlaLeu

FIG. 2B

```
GACTTCGGCCAGGCGTTTCAACTGCTGCTGGACGATCTGCGTGACGATCACCCGGAAACCGGT    840
AspPheGlyGlnAlaPheGlnLeuLeuLeuAspAspLeuArgAspAspHisProGluThrGly

AAAGATCGCAATAAGGACGGGGAAAAATCGACGCTGGTCAACCGGCTGGGCGCAGACGCG        900
LysAspArgAsnLysAspAlaGlyLysSerThrLeuValAsnArgLeuGlyAlaAspAla

GCCCGGCAAAAGCTGCGCGAGCATATTGATTCCGCCGACAAACACCTCACTTTTGCCTGT        960
AlaArgGlnLysLeuArgGluHisIleAspSerAlaAspLysHisLeuThrPheAlaCys
                                  Bal I

CCGCAGGGGGCGGCCATCCGACAGTTTATGCATCACCTTGTGGTTTGGCCATCACCTTGCCGAC  1020
ProGlnGlyGlyAlaIleArgGlnPheMetHisHisLeuTrpPheGlyHisHisLeuAlaAsp

TGGTCACCGGTCATGAAAAATCGCCCTGATACCGGCCCTTTTGGGTTCAAGCAGTACATAACG   1080
TrpSerProValMetLysIleAla

ATGGAACCACATTACAGGAGTAGTGATGAATGAAGGACGAGCGCCTTGTTCAGGGTAAGA      1140
EcoRV
ACGATCATCTGGATATC
```

FIG. 2C

```
Bgl II
AGATCTAAAGGCACAGGCGTCTCATGCTTCGCACAATGTAAAACTGCTTCAGAACCTGGCG          60

Hpa I
AGAGCTATCCGCGGGTCTACGGTTAACTGATACTAAAAGACAATTCAGCGGGTAACCCTT         120

Nco I      Nru I
GCAATGGTGAGTGGCAGTAAAGCGGGCGTCATGGCCGAATTCGAAATAGAGGTAATGAGA         180
                              MetAlaGluPheGluIleGluValMetArg

CAATCCATTGACGATCACCTGGCCCTGTTACCTGAAACCGACAGCCAGGATATCGTC            240
GlnSerIleAspAspHisLeuAlaGlyLeuLeuLeuProGluThrAspSerGlnAspIleVal

Bam HI
AGCCTTGCGGATGGCGTGAAGGCGTCATGGCACCCGGTAAACGGATCCGTCCGCTGCTGATG       300
SerLeuAlaMetArgGluGlyValMetAlaProGlyLysArgIleArgProLeuLeuMet

CTGCTGGCCGCCCGCGATGCCCTGCCTACCAGGGCAGTATGCCGCTACGCTTCGCC             360
LeuLeuAlaAlaArgAspLeuArgTyrGlnGlySerMetProThrLeuLeuAspLeuAla

TGCGCCGGTTGAACTGACCCATACCGGTCGCTGATGCTCGACGACATGCCCTGCATGGAC        420
CysAlaValGluLeuThrHisThrAlaSerLeuMetLeuAspAspMetProCysMetAsp
```

FIG. 3A

```
ACCGGCCGAGCTGCGCCGCGGTCAGCCACTACCCACAAAAATTGGTGAGAGCGTGGCG          480
AsnAlaGluLeuArgArgGlyGlnProThrThrHisLysLysPheGlyGluSerValAla

ATCCTTGCCTCCGTTGGCTGTGCTCTCTAAAGCCTTTGGTCTGATCGCCGCCACCGGCGAT       540
IleLeuAlaSerValGlyLeuLeuSerLysAlaPheGlyLeuIleAlaAlaThrGlyAsp

CTGCCGGGGGAGAGGCGTGCCCAGGCGGTCAACGAGCTCTCTACCGCCGTGGGGCTGCAG        600
LeuProGlyGluArgArgAlaGlnAlaValAsnGluLeuSerThrAlaValGlyLeuGln

GGCCTGGTACTGGGGCAGTTTCGCGATCTTAACGATGCCGCCCTGACCGTACCCCCTGAC        660
GlyLeuValLeuGlyGlnPheArgAspLeuAsnAspAlaAlaLeuThrValProProAsp

GCTATCCTCAGCACCAACCACCTCAAGACCGGCATTCTGTTCAGCGCCGATGCTGCAGATC      720
AlaIleLeuSerThrAsnHisLeuLysThrGlyIleLeuPheSerAlaMetLeuGlnIle

GTCGCCATTGCTTCCGCCTCGTCGCCGAGCACGCCGAGAGACGCTGCACGCCTTCGCCCTC       780
ValAlaIleAlaSerProSerThrArgGluThrLeuHisAlaPheAlaLeu
```

FIG. 3B

```
GACTTCGGCCAGGCGTTTCAACTGCTGGACGATCTGCTGGACGATCACCCGGAAACCGGT      840
AspPheGlyGlnAlaPheGlnLeuLeuAspAspLeuLeuAspAspHisProGluThrGly

AAAGATCGCAATAAGGACGCGGAAAATCGACGCTGGTCAACCGGCTGGGCGCAGACGCG      900
LysAspArgAsnLysAspAlaGluAsnArgArgTrpSerThrGlyTrpAlaAspAla

GCCCGGCAAAAGCTGCGCGAGCATATTGATTCCGCCGACAAACACCTCACTTTTGCCTGT      960
AlaArgGlnLysLeuArgGluHisIleAspSerAlaAspLysHisLeuThrPheAlaCys
                                                    Bal I

CCGCAGGGCGGGGCGGCCATCCCGACAGTTTATGCATCTGTGGTTTGGCCATCACCTTTGCCGAC   1020
ProGlnGlyGlyAlaIleProThrValTyrAlaSerValValTrpProSerProLeuProThr
                                                              ?

TGGTCACCGGTCATGAAAAATCGCCTGATACCGCCCTTTTGGGTTCAAGCAGTACATAACG    1080
TrpSerProValMetLysIleAla

ATGGAACCACATTACAGGAGTAGTGATGATGAATGAAGGACGAGCCCTTGTTCAGGGTAAGA   1140

Eco RV
ACGATCATCTGGATATC
```

FIG. 3C

```
         Bgl II                    Nco I
GATTGAGGATCTGCAATGAGCCAACCGCCGCTGCTTGACCACGCCAGACCATGGCC        60
              MetSerGlnProProLeuLeuAspHisAlaThrGlnThrMetAla

AACGGCTCGAAAAGTTTGCCACCGCTGCGAAGCTGTTCGACCCGGCCACCCGCGTAGC     120
AsnGlySerLysSerPheAlaThrAlaAlaLysLeuPheAspProAlaThrArgArgSer

GTGCTGATGCTCTACACCTGGTGCCGCCACTGCGATGACGTCATTGACGACCAGACCCAC    180
ValLeuMetLeuTyrThrTrpCysArgHisCysAspAspValIleAspAspGlnThrHis

GGCTTCGCCAGCGAGGCCGGCGAGGAGGCCACCGCAGGCGCTGGCCCGGCTGCGC        240
GlyPheAlaSerGluAlaGlyGluGluAlaThrAlaThrGlnArgLeuAlaArgLeuArg
                                              Bam HI
ACGCTGACCCTGGCGGCGTTTGAAGGGCCGAGATGCAGGATCCGGCCTTCGCCTTT        300
ThrLeuThrLeuAlaAlaPheGluGlyAlaGluMetGlnAspProAlaPheAlaAlaPhe

CAGGAGGTGGCGCTGACCACGGTATTACGCCCCGCATGGCGCTCGATCACCTGACGGC    360
GlnGluValAlaLeuThrHisGlyIleThrProArgMetAlaLeuAspHisLeuAspGly
```

FIG. 4A

```
TTTGCGATGGACGTGGCTCAGACCCGGTATGTCACCTTTGAGGATACGCTGCGCTACTGC      420
PheAlaMetAspValAlaGlnThrArgTyrValThrPheGluAspThrLeuArgTyrCys

TATCACGTGGGCGTGGTGGTCGGTGATGATGGCCAGGGTGATGGGCGTGCGGGATGAG       480
TyrHisValAlaGlyValValGlyLeuMetMetAlaArgValMetGlyValArgAspGlu
                                                            Sma I
CGGGTGCTGGATCGCGCGCCTGCGGCCTTCCAGCTGACGAATATGGCCCGG               540
ArgValLeuAspArgAlaCysAspLeuGlyLeuAlaPheGlnLeuThrAsnMetAlaArg
                                                Pst I
GATATTATTGACGATGGGGCTATTGACCGCTGCTATCTGCCCGAGTGGCTGCAGGAT        600
AspIleIleAspAspAlaAlaIleAspArgCysTyrLeuProAlaGluTrpLeuGlnAsp

GCCGGGCTGGCCCCCGGAGAACTATGCCGGGAGAATCGCCGGGCCCTGGCCGCGGTGG       660
AlaGlyLeuAlaProGluAsnTyrAlaAlaArgGluAsnArgProAlaLeuAlaArgTrp

CGGAGGCTTATTGATGCCGCAGAGCCGTACTACATCTCCTCCCAGGCCGGGCTACACGAT    720
ArgArgLeuIleAspAlaAlaGluProTyrTyrIleSerSerGlnAlaGlyLeuHisAsp
```

FIG. 4B

```
CTGGCGGGCGCTCCGCGTGGGCGATCGCCACCGCCCGCAGCGTCTACCGGGAGATCGGT    780
LeuArgArgSerAlaTrpAlaIleAlaThrAlaArgSerValTyrArgGluIleGly

ATTAAGGTAAAAAGCGCGGGAGGCAGGCGCCTGGGATCGCCGCAGCACCAGCAAAGGT    840
IleLysValAlaAlaGlyGlySerAlaTrpAspArgArgGlnHisThrSerLysGly

GAAAAAATTGCCATGCTGATGGCGCACCGGGCAGGTTATTCGGGCGAAGACGACGAGG    900
GluLysIleAlaMetLeuMetAlaAlaProGlyGlnValIleArgAlaLysThrThrArg

GTGACGCCGCCTCCGGCCGTCTTTGGCAGCGTCCCGTTTAGGCGGGCCATGACGTT      960
ValThrProArgProAlaGlyLeuTrpGlnArgProVal

CACGCAGGATCGCCTGTAGGTCGGCAGGCTTGCGGGCGTAAATAAAACCGAAGGAGACGC  1020
         Bam HI

AGCCCCTCCCGGCACCGCGTGGTGCAGGCGGTGGGCGACGTAGAGCCGCTTCAGGT     1080

AGCCCCGGCGGGGATCCAGTGGAAGGGCCAGCGCTGATGCACCAGACCGTCGTGCACCA  1140
                                                Pst I

GGAAGTAGAGCAGGCCATAGACCGTCATGCCGCAGCCAATCCACTGCAGGGCCAAAC    1200
```

FIG. 4C

```
                     Nco I
TAAACCATGGAAAAACCGTTGTGATTGGCGCAGGCTTTGGTGGCCTGGCGCTGGCGATT      60
        MetLysThrValValIleGlyAlaGlyPheGlyGlyLeuAlaLeuAlaIle

Pst I       Bam HI
CGCCTGCAGGCGGGCAGGGGATCCCAACCGTACTGTGCTGGAGCAGCGGGACAAGCCCGGT    120
ArgLeuGlnAlaAlaGlyIleProThrValLeuLeuGluGlnArgAspLysProGlyGly

CGGGCCTACGTGTCTGGCATGACCAGGGCTTTACCTTTGACGCCGACGGTGATCACC       180
ArgAlaTyrValTrpHisAspGlnGlyPheThrPheAspAlaGlyProThrValIleThr

GATCCTACCGCGCTTGAGGGCTGTTCACCCTGGCCGCAGGCGCATGGAGGATTACGTC      240
AspProThrAlaLeuGluAlaLeuPheThrLeuAlaGlyArgArgMetGluAspTyrVal

AGGCTGCTGCCGGTAAAACCCTTCTACCGACTCTGCTGGGAGTCCGGAAGACCCTCGAC     300
ArgLeuLeuProValLysProPheTyrArgLeuCysTrpGluSerGlyLysThrLeuAsp

TATGCTAACGACAGCTTCGAGCTTGAGGCGCAGATTACCCAGTTCAACCCCCGCGACGTC    360
TyrAlaAsnAspSerPheGluLeuGluAlaGlnIleThrGlnPheAsnProArgAspVal

GAGGGCTACCGGCGCTTTCTGGCTTACTCCCAGGCGTATTCCAGGAGGATATTTGCGC      420
GluGlyTyrArgArgPheLeuAlaTyrSerGlnAlaValPheGlnGluGlyTyrLeuArg
```

FIG. 11A

```
                    Nru I
          480  CTCGGGCAGGGTGCCGTTCCTCTTCTTTTCGCGACATGCTGCCGCCGGGCCGCAGCTGCTT
               LeuGlySerValProPheLeuSerPheArgAspMetLeuArgAlaGlyProGlnLeuLeu

540  AAGCTCCAGGCCGTGGCCAGAGCGTCTACCAGTCGGTTTCGCGTTTATTGAGGATGAGCAT
               LysLeuGlnAlaTrpGlnSerValTyrGlnSerValSerArgPheIleGluAspGluHis

600  CTGCGGGCAGGCCTTCTCGTTCCACTCCCTGCTGGTAGGCGGCAACCCCTTCACCACCTCG
               LeuArgGlnAlaPheSerPheHisSerLeuLeuValGlyGlyAsnProPheThrThrSer

660  TCCATCTACACCCTGATCCACGCCCTTGAGCGGGAGTGGGGGTCTGTTCCCTGAGGGC
               SerIleTyrThrLeuIleHisAlaLeuGluArgGluTrpGlyValTrpPheProGluGly

720  GGCACCGGGGCGGCTGGTGAACGGCATGGTGAAGCTGTTTACCGATCTGGGCGGGAGATC
               GlyThrGlyAlaLeuValAsnGlyMetValLysLeuPheThrAspLeuGlyGlyGluIle

Sma I
          780  GAACTCAACGCCCGGGTCGAAGAGCTGGTGGCCGATAACCGCGTAAGCCAGGTCCGG
               GluLeuAsnAlaArgValGluLeuValAlaAspAsnArgValSerGlnValArg
```

FIG. 11B

```
CTCGCGGATGGTCGGATCTTTGACACCGACGCCCTCGAACGCTGACGTGGTGAAC      840
LeuAlaAspGlyValAspIlePheAspThrAspAlaLeuAsnAlaAspValValAsn

ACCTATAAAAAGCTGCTCGGCACCACCATACCGGTGGGGCAGAAGCGGGCACGGCTGGAG   900
ThrTyrLysLysLeuLeuGlyThrIleProValGlyGlnLysArgAlaArgLeuGlu

CGCAAGAGCATGAGCAACTCGCTGTTTGTGCTCTACTTCGGCCTGAACCAGCCTCATTCC   960
ArgLysSerMetSerAsnSerLeuPheValLeuTyrPheGlyLeuAsnGlnProHisSer
                                                    Bgl II
CAGCTGGGGCACCATACCATCTGTTTTGGTCCCCGCTACCGGGAGCTGATCGACGAGATC   1020
GlnLeuAlaHisThrIleCysPheGlyProArgTyrArgGluLeuIleAspGluIle

TTTACCGGCAGCGCCTGGGCGGATGACTTCTCGCTCTACTTGCACTCGCCCTGCGTGACC   1080
PheThrGlySerAlaLeuAlaAspAspPheSerLeuTyrLeuHisSerProCysValThr

GATCCCCTCGCTGCGCCTCCCCCGTGCGCCAGCTTCTACGTGCTGGCCGTGCCGCAT      1140
AspProSerLeuAlaProProProCysAlaSerPheTyrValLeuAlaProValProHis
```

FIG. 11C

```
CTTGGCAACGCGCCGCTGGACTGGGCGCAGGAGGGCGCAGAAGCTGCCGACCGCATCTTT    1200
LeuGlyAsnAlaProLeuAspTrpAlaGlnGluGlyProLysLeuArgAspArgIlePhe

GACTACCTTGAAGAGCGCTATATGCCCGGCCTGCGTAGCCAGTCTGGTGACCCAGCGGATC    1260
AspTyrLeuGluGluArgTyrMetProGlyLeuArgSerGlnLeuValThrGlnArgIle

TTTACCCGGCAGACTTCACGACACGCTTGGATCGCGATCTTGGAGATCGCTTTTCATCGAG    1320
PheThrArgGlnThrSerArgHisAlaTrpIleAlaIleLeuGlySerLeuPheIleGlu

CCGCCTTCGTTGACCCAAGGCTTGTTGTTCGCCCGCAAACGCGACAGCAGACATTCAAACCTCTAC    1380
ProProSerLeuThrGlnGlyLeuPheAlaAlaAsnAlaThrArgHisSerAsnLeuTyr

CTGGTGGCCGCAGGTACTCACCCTGGCGGGCATTCCTGGCGGCATTCCTGGGGCCTCGCCGAA    1440
LeuValAlaAlaGlyThrHisProGlyAlaGlyIleProGlyValValGlyLeuAlaGlu

AGCACCGCCAGCCTGATGATTGAGGATCTGCAATGAGCCAACCGCCTGCTTGACCACG    1500
SerThrAlaSerLeuMetIleGluAspLeuGln

Nco I Bal I
CCACGCAGACCATGGCCA
```

FIG. 11D

```
                                                                                      GAGG
Sal I
TCGACGATGGAAAAACCGTTGTGATTGGGCGCAGGCTTTGGTGGCCTGGCGCTGGCGATT              64
              MetGluLysThrValValIleGlyAlaGlyPheGlyGlyLeuAlaLeuAlaIle

Pst I    Bam HI
CGCCTGCAGGGCGGCAGGGATCCCAACCGTACTGCTGGAGCAGCGGGACAAGCCCGGCGT             124
ArgLeuGlnAlaAlaGlyIleProThrValLeuLeuGluGlnArgAspLysProGlyGly

CGGGGCCTACGTCTCTGGCATGACCAGGCTTTACCTTTGACGCCCGACGGTGATCACC              184
ArgAlaTyrValTrpHisAspGlnGlyPheThrPheAspAlaGlyProThrValIleThr

GATCCTACCGGCGCTTGAGGCGCTGTTCACCCTGGCCGCCAGGCGCATGGAGGATTACGTC           244
AspProThrAlaLeuGluAlaLeuPheThrLeuAlaGlyArgArgMetGluAspTyrVal

AGGCTGCTGCCGGTAAAACCCTTCTACCGACTCTGCTGGGAGTCCGGAAGACCCTCGAC             304
ArgLeuLeuProValLysProPheTyrArgLeuCysTrpGluSerGlyLysThrLeuAsp

TATGCTAACGACAGCTTCGAGGCGCAGATTACCCCAGTTCAACCCCCGCGACGTC                 364
TyrAlaAsnAspSerPheGluAlaGlnIleThrGlnPheAsnProArgAspVal
```

FIG. 15A

```
GAGGGCTACCGGCGCTTTCTGGCTTACTCCCAGGCGGTATTCCAGGAGGATATTTGCGC    424
GluGlyTyrArgArgPheLeuAlaTyrSerGlnAlaValPheGlnGluGlyTyrLeuArg
                        Nru I
CTCGGCAGCGTGCCGTTCCTCTCTTTCGCGACATGCTGCGCCGGGCCGCAGCTGCTT      484
LeuGlySerValProPheLeuSerPheArgAspMetLeuArgAlaGlyProGlnLeuLeu

AAGCTCCAGGCGTGGACAGAGCGTCTACCAGTCGGTTTCGCTTTATTGAGGATGAGCAT    544
LysLeuGlnAlaTrpGlnSerValTyrGlnSerValSerArgPheIleGluAspGluHis

CTGCGGCAGGCCTTCTCGTTCCACTCCCTGCTGGAGGCGGCAACCCCCTTCACCACCTCG   604
LeuArgGlnAlaPheSerPheHisSerLeuLeuValGlyAsnProPheThrThrSer

TCCATCTACACCCTGATCCACGCCCTTGAGCGGGAGTGGGGGTCTGTTCCCTGAGGC       664
SerIleTyrThrLeuIleHisAlaLeuGluArgGluTrpGlyValTrpPheProGluGly

GGCACCGGGGGCTGGTGAACGGCATGGTGAAGCTGTTTACCGATCTGGGCGGGAGATC     724
GlyThrGlyAlaLeuValAsnGlyMetValLysLeuPheThrAspLeuGlyGlyGluIle

GAACTCAACGCCCGGGTCGAAGAGCTGGTGGCCGATAACCGCGTAAGCCAGGTCCGG      784
GluLeuAsnAlaArgValGluGluLeuValAlaAspAsnArgValSerGlnValArg
                                          Sma I
```

FIG. 15B

```
CTCGCGGGATGGTCGGATCTTTGACACCGACGCCCTCGAACGCCTCGACGTGGTGAAC    844
LeuAlaAspGlyArgIlePheAspThrAspAlaSerAsnAlaAspValValAsn

ACCTATAAAAGCTGCTCGGCACCATACCGGTGGGGCAGAAGCGGGCGGCACGGCTGGAG    904
ThrTyrLysLysLeuLeuGlyThrIleProValGlyGlnLysArgAlaAlaArgLeuGlu

CGCAAGAGAGCATGAGCAACTCGCTGTTTGTGCTCTACTTCGGCCTGAACCAGCTCATTCC    964
ArgLysSerMetSerAsnSerLeuPheValLeuTyrPheGlyLeuAsnGlnProHisSer
                                                    Bgl II
CAGCTGGCACCATACCATCTGTTTTGGTCCCCGCTACCGGGAGCTGATCGACGAGATC    1024
GlnLeuAlaHisHisThrIleCysPheGlyProArgTyrArgGluLeuIleAspGluIle

TTTACCGGCAGCGCGTGGCGGATGACTTCTGCTCTACCTGCACTCGCCCTGCCTGACC    1084
PheThrArgGlnThrSerArgHisAlaTrpIleAlaIleLeuGlySerLeuPheIleGlu

GATCCCTCGCTCGCGCCTCCCCCGTGCCCAGCTTCTACGTGCTGGCCCCGTGCCGCAT    1144
AspProSerLeuAlaProProProCysAlaSerPheTyrValLeuAlaProValProHis

CTTGGCAACGCGCCGCTGGACTGGGCGCAGGAGGGGCCGAAGCTGCGGGACCGGCATCTTT    1204
LeuGlyAsnAlaProLeuAspTrpAlaGlnGluGlyProLysLeuArgAspArgIlePhe
```

FIG. 15C

```
GACTACCTTGAAGAGCGCTATATGCCCGGCCTGCGTAGCCAGCTGGTGACCCAGCGGATC    1264
AspTyrLeuGluArgArgTyrMetProGlyLeuArgSerGlnLeuValThrGlnArgIle

TTTACCCGCAGACTTCACGACACGCTTGGATCGCGATCTTCATCGAG    1324
PheThrArgGlnThrSerArgHisAlaTrpIleAlaIleLeuGlySerLeuPheIleGlu

CCGCCTTCGTTGACCCAAGGCTTGTTCGCCGCAAACGCGACACATTCAAACCTCTAC    1384
ProProSerLeuThrGlnGlyLeuPheAlaAlaAsnAlaThrArgHisSerAsnLeuTyr

CTGGTGGCCGCAGGTACTCACCCTGGGCGGCATTCCTGGCTAGTGGGCCTCGCCGAA    1444
LeuValAlaAlaGlyThrHisProGlyAlaGlyIleProGlyValValGlyLeuAlaGlu

AGCACCGCCAGCCTGATGATTGAGGATCTGCAATGAGCCAACCGCCGCTGCTTGACCACG    1504
SerThrAlaSerLeuMetIleGluAspLeuGln

Sal I
CCACGTCGACCATGGCCA
```

FIG. 15D

```
ATG GCT TCC TCA GTT CTT TCC TCT GCA GCA GTT GCC ACC CGC AGC
MET Ala Ser Ser Val Leu Ser Ser Ala Ala Val Ala Thr Arg Ser
                        27                                              81
AAT GTT GCT CAA GCT AAC ATG GTG GCG CCT TTC ACT GGC CTT AAG
Asn Val Ala Gln Ala Asn MET Val Ala Pro Phe Thr Gly Leu Lys
                        108                                             135
TCA GCC TCA TTC CCT GTT TCA AGG AAG CAA AAC CTT GAC ATC
Ser Ala Ala Ser Phe Pro Val Ser Arg Lys Gln Asn Leu Asp Ile
                        162
ACT TCC ATT GCC AGC AAC GGC GGA AGA GTG CAA TGC ATG CAG
Thr Ser Ile Ala Ser Asn Gly Gly Arg Val Gln Cys MET Gln
```

FIG. 17

```
                    Sph I
AGGGAGTGAGAGCGTATCGTGAGGGATCTGATTTTAGTCGGGGCCTGGCCAACGGG              60
                            GCGGCATGCGG
                               MetArgAspLeuIleLeuValGlyGlyGlyLeuAlaAsnGly

CTGATCGCCTGGCGTCTGCGCCAGCGCTTAACCTGCTGCTGATCGAGGCC                   120
LeuIleAlaTrpArgLeuArgGlnArgTyrProGlnLeuAsnLeuLeuIleGluAla

GGGGAGCAGCCCGGGGAACCATACCTGGTCATTCCATGAAGACGATCTGACTCCCGG            180
GlyGluGlnProGlyGlyAsnHisThrTrpSerPheHisGluAspAspLeuThrProGly

CAGCACGCCCTGGCTGGCCCCGCTACCTCTGGCCCCACGCCTGGCCTATGAGGTGCAGTTT        240
GlnHisAlaLeuAlaProLeuLeuAlaAlaHisAlaAlaTrpProGlyTyrGluValGlnPhe

CCCGATCTTCGCCTCCGTCGCGCCTACTACTCCATTACCTCAGAGCGCTTTGCC               300
ProAspLeuArgArgArgLeuAlaArgGlyTyrTyrSerIleThrSerGluArgPheAla

GAGGCCCTGCATCAGGGCGCTGGGGAGAACATCTGCTAAACTGTTCGGTGAGGAGGTG           360
GluAlaLeuHisGlnAlaLeuGlyGluAsnIleTrpLeuAsnCysSerValSerGluVal

TTACCCAATAGCGTGCGCCTTGCCAACGGTGAGGCGCTGCTTGCCGAGCCGGTGATTGAC         420
LeuProAsnSerValArgLeuAlaAsnGlyGluAlaLeuLeuAlaGlyAlaValIleAsp
```

FIG. 19A

```
GGACGCGGGCGTGACCGGCCAGTTCGGCGATGCAAACCGGCTATCAGCTCTTTCTTGGTCAG   480
GlyArgGlyValThrAlaSerSerAlaMetGlnThrGlyTyrGlnLeuPheLeuGlyGln

CAGTGGCGGCTGACACAGCCCCACGGCCTGACCGTACCGATCCTGATGGATGCCACGGTG   540
GlnTrpArgLeuThrGlnProHisGlyLeuThrValProIleLeuMetAspAlaThrVal

GCGCAGCAGGGCTATCGCTTTGTCTACACGCGCTGCTCCCGCCGACACGCTGCTG       600
AlaGlnGlnGlyTyrArgPheValTyrThrLeuProLeuSerAlaAspThrLeuLeu

ATCGAGGATACGCGCTACGCCAATGTCCCGCCAGCGTGATGATAATGCCCTACGCCAGACG   660
IleGluAspThrArgTyrAlaAsnValProGlnArgAspAspAsnAlaLeuArgGlnThr

GTTACCGACTATGCTCACAGCAAAGGGTGGCAGCTGGCCCAGCTTGAACGCGAGGAGACC   720
ValThrAspTyrAlaHisSerLysGlyTrpGlnLeuAlaGlnLeuGluArgGluGluThr

GGCTGTCTGCCGATTACCTGGCGGGTGACATCCAGGTCTCTGTGGGCCGATGCGCCGGCGT   780
GlyCysLeuProIleThrTrpArgValThrSerArgLeuCysGlyProMetArgArgArg

GCCGCGTCGGGAATGCGGGCTGGGCTGCTATTCACCCTACCACTGGCTATTCGCTGCCGCTG   840
AlaAlaSerGlyMetArgAlaGlyLeuPheHisProThrThrGlyTyrSerLeuProLeu
```

FIG. 19B

```
GCGGTGGCCCTTGCCGACGGGATTGCCGACAGCCCGGCTGGGCAGCGGTTCCGCTCTAT   900
AlaValAlaLeuAlaAspGlyIleAlaAspSerProArgLeuGlySerValProLeuTyr

CAGCTCACCCGGCAGTTTGCCGAACGCCACTGGCGCAGGCAGGATTCTTCCGCCTGCTG   960
GlnLeuThrArgGlnPheAlaGluArgHisTrpArgArgGlnGlyPhePheArgLeuLeu

AACCGGATGCTTTTCCTGGCCGGGGCGGAGGAGAACCGCTGGCGGGTGATGCAGCGCTTT  1020
AsnArgMetLeuPheLeuAlaGlyAlaGluGluAsnArgTrpArgValMetGlnArgPhe

TATGGGCTGCCGGAGCCCACCGGAGCCCTAGAGCCGCTTTTACGCCGGCTCTCTCTTTGAT  1080
TyrGlyLeuProGluProThrValGluArgPheTyrAlaGlyArgLeuSerLeuPheAsp

AAGGCCCGCATTTTGACGGGCAAGCCACCGGTTCCGCTGGCGAAGTCTGGCGGGGGCGC  1140
LysAlaArgIleLeuThrGlyLysProProValProLeuAlaLysSerGlyGlyArgArg

TGAACCATTTTCCTGACAGAGAGATAAAGGATGAAAAAAACCGTTGTGATTGGCCAGG    1200
                                                    BamHI
GATCCGATG
Pst I
CTTTGGTGGCCTGGCCTGGCGCTGGCCGATTCGCCTGCAG
```

FIG. 19C

SEQUENCE LISTING ( 1 ) GENERAL INFORMATION:

( i i i ) NUMBER OF SEQUENCES: 79

( 2 ) INFORMATION FOR SEQ ID NO:1:

( i ) SEQUENCE CHARACTERISTICS:
        ( A ) LENGTH: 1157 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:1:

|  |  |  |  |  |  | AGA | 3 |
|---|---|---|---|---|---|---|---|
| TCTAAAGGCA | CAGCGTCTCA | TGCTTCGCAC | AATGTAAAAC | TGCTTCAGAA | CCTGGCGAGA | | 63 |
| GCTATCCGCG | CGGTCTACGG | TTAACTGATA | CTAAAAGACA | ATTCAGCGGG | TAACCTTGCA | | 123 |
| ATGGTGAGTG | GCAGTAAAGC | GGGCGTTTCG | CCTCATCGCG | AAATAGAGGT | AATGAGACAA | | 183 |
| TCCATTGACG | ATCACCTGGC | TGGCCTGTTA | CCTGAAACCG | ACAGCCAGGA | TATCGTCAGC | | 243 |
| CTTGCGATGC | GTGAAGGCGT | CATGGCACCC | GGTAAACGGA | TCCGTCCGCT | GCTGATGCTG | | 303 |
| CTGGCCGCCC | GCGACCTCCG | CTACCAGGGC | AGTATGCCTA | CGCTGCTCGA | TCTCGCCTGC | | 363 |
| GCCGTTGAAC | TGACCCATAC | CGCGTCGCTG | ATGCTCGACG | ACATGCCCTG | CATGGACACC | | 423 |
| GCCGAGCTGC | GCCGCGGTCA | GCCCACTACC | CACAAAAAAT | TGGTGAGAG | CGTGGCGATC | | 483 |
| CTTGCCTCCG | TTGGGCTGCT | CTCTAAAGCC | TTTGGTCTGA | TCGCCGCCAC | CGGCGATCTG | | 543 |
| CCGGGGGAGA | GGCGTGCCCA | GGCGGTCAAC | GAGCTCTCTA | CCGCCGTGGG | GCTGCAGGGC | | 603 |
| CTGGTACTGG | GGCAGTTTCG | CGATCTTAAC | GATGCCGCCC | TCGACCGTAC | CCCTGACGCT | | 663 |
| ATCCTCAGCA | CCAACCACCT | CAAGACCGGC | ATTCTGTTCA | GCGCGATGCT | GCAGATCGTC | | 723 |
| GCCATTGCTT | CCGCCTCGTC | GCCGAGCACG | CGAGAGACGC | TGCACGCCTT | CGCCCTCGAC | | 783 |
| TTCGGCCAGG | CGTTTCAACT | GCTGGACGAT | CTGCGTGACG | ATCACCCGGA | AACCGGTAAA | | 843 |
| GATCGCAATA | AGGACGCGGG | AAAATCGACG | CTGGTCAACC | GGCTGGGCGC | AGACGCGGCC | | 903 |
| CGGCAAAAGC | TGCGCGAGCA | TATTGATTCC | GCCGACAAAC | ACCTCACTTT | TGCCTGTCCG | | 963 |
| CAGGGCGGCG | CCATCCGACA | GTTTATGCAT | CTGTGGTTTG | CCATCACCT | TGCCGACTGG | | 1023 |
| TCACCGGTCA | TGAAAATCGC | CTGATACCGC | CCTTTTGGGT | TCAAGCAGTA | CATAACGATG | | 1083 |
| GAACCACATT | ACAGGAGTAG | TGATGAATGA | AGGACGAGCG | CCTTGTTCAG | CGTAAGAACG | | 1143 |
| ATCATCTGGA | TATC |  |  |  |  |  | 1157 |

( 2 ) INFORMATION FOR SEQ ID NO:2:

( i ) SEQUENCE CHARACTERISTICS:
( A ) LENGTH: 307 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Val Ser Gly Ser Lys Ala Gly Val Ser Pro His Arg Glu Ile Glu
 1               5                  10                  15

Val Met Arg Gln Ser Ile Asp Asp His Leu Ala Gly Leu Leu Pro Glu
            20                  25                  30

Thr Asp Ser Gln Asp Ile Val Ser Leu Ala Met Arg Glu Gly Val Met
            35                  40                  45

Ala Pro Gly Lys Arg Ile Arg Pro Leu Leu Met Leu Leu Ala Ala Arg
        50                  55                  60

Asp Leu Arg Tyr Gln Gly Ser Met Pro Thr Leu Leu Asp Leu Ala Cys
65                  70                  75                  80

Ala Val Glu Leu Thr His Thr Ala Ser Leu Met Leu Asp Asp Met Pro
                85                  90                  95

Cys Met Asp Asn Ala Glu Leu Arg Arg Gly Gln Pro Thr Thr His Lys
                100                 105                 110
```

```
Lys Phe Gly Glu Ser Val Ala Ile Leu Ala Ser Val Gly Leu Leu Ser
        115                 120             125
Lys Ala Phe Gly Leu Ile Ala Thr Gly Asp Leu Pro Gly Glu Arg
    130             135                 140
Arg Ala Gln Ala Val Asn Glu Leu Ser Thr Ala Val Gly Leu Gln Gly
145             150             155                     160
Leu Val Leu Gly Gln Phe Arg Asp Leu Asn Asp Ala Ala Leu Asp Arg
                165             170                 175
Thr Pro Asp Ala Ile Leu Ser Thr Asn His Leu Lys Thr Gly Ile Leu
            180             185                 190
Phe Ser Ala Met Leu Gln Ile Val Ala Ile Ala Ser Ala Ser Ser Pro
        195                 200             205
Ser Thr Arg Glu Thr Leu His Ala Phe Ala Leu Asp Phe Gly Gln Ala
    210             215                 220
Phe Gln Leu Leu Asp Asp Leu Arg Asp Asp His Pro Glu Thr Gly Lys
225             230             235                     240
Asp Arg Asn Lys Asp Ala Gly Lys Ser Thr Leu Val Asn Arg Leu Gly
                245             250                 255
Ala Asp Ala Ala Arg Gln Lys Leu Arg Glu His Ile Asp Ser Ala Asp
            260             265                 270
Lys His Leu Thr Phe Ala Cys Pro Gln Gly Gly Ala Ile Arg Gln Phe
        275                 280             285
Met His Leu Trp Phe Gly His His Leu Ala Asp Trp Ser Pro Val Met
    290             295                 300
Lys Ile Ala
305
```

( 2 ) INFORMATION FOR SEQ ID NO:3:

( i ) SEQUENCE CHARACTERISTICS:
      ( A ) LENGTH: 1157 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:3:

```
                                        AGATCTAAAG GCACAGCGTC TCATGCTTCG    30
CACAATGTAA AACTGCTTCA GAACCTGGCG AGAGCTATCC GCGCGGTCTA CGGTTAACTG    90
ATACTAAAAG ACAATTCAGC GGGTAACCTT GCAATGGTGA GTGGCAGTAA AGCGGGCGTC   150
ATGGCCGAAT TCGAAATAGA GGTAATGAGA CAATCCATTG ACGATCACCT GGCTGGCCTG   210
TTACCTGAAA CCGACAGCCA GGATATCGTC AGCCTTGCGA TGCGTGAAGG CGTCATGGCA   270
CCCGGTAAAC GGATCCGTCC GCTGCTGATG CTGCTGGCCG CCCGCGACCT CCGCTACCAG   330
GGCAGTATGC CTACGCTGCT CGATCTCGCC TGCGCCGTTG AACTGACCCA TACCGCGTCG   390
CTGATGCTCG ACGACATGCC CTGCATGGAC ACCGCCGAGC TGCGCCGCGG TCAGCCCACT   450
ACCCACAAAA AATTTGGTGA GAGCGTGGCG ATCCTTGCCT CCGTTGGGCT GCTCTCTAAA   510
GCCTTTGGTC TGATCGCCGC CACCGGCGAT CTGCCGGGGG AGAGGCGTGC CAGGCGGTC   570
AACGAGCTCT CTACCGCCGT GGGGCTGCAG GGCCTGGTAC TGGGGCAGTT CGCGATCTT   630
AACGATGCCG CCCTCGACCG TACCCCTGAC GCTATCCTCA GCACCAACCA CCTCAAGACC   690
GGCATTCTGT TCAGCGCGAT GCTGCAGATC GTCGCCATTG CTTCCGCCTC GTCGCCGAGC   750
ACGCGAGAGA CGCTGCACGC CTTCGCCCTC GACTTCGGCC AGGCGTTTCA ACTGCTGGAC   810
```

```
GATCTGCGTG ACGATCACCC GGAAACCGGT AAAGATCGCA ATAAGGACGC GGGAAAATCG   870

ACGCTGGTCA ACCGGCTGGG CGCAGACGCG GCCCGGCAAA AGCTGCGCGA GCATATTGAT   930

TCCGCCGACA AACACCTCAC TTTTGCCTGT CCGCAGGGCG GCGCCATCCG ACAGTTTATG   990

CATCTGTGGT TTGGCCATCA CCTTGCCGAC TGGTCACCGG TCATGAAAAT CGCCTGATAC  1050

CGCCCTTTTG GGTTCAAGCA GTACATAACG ATGGAACCAC ATTACAGGAG TAGTGATGAA  1110

TGAAGGACGA GCGCCTTGTT CAGCGTAAGA ACGATCATCT GGATATC                1157
```

(2) INFORMATION FOR SEQ ID NO:4:

(i) SEQUENCE CHARACTERISTICS:
      (A) LENGTH: 298 amino acids
      (B) TYPE: amino acid
      (D) TOPOLOGY: linear (ii) MOLECULE TYPE: protein (xi) SEQUENCE DESCRIPTION: SEQ ID NO:4:

```
Met Ala Glu Phe Glu Ile Glu Val Met Arg Gln Ser Ile Asp Asp His
 1               5                  10                  15

Leu Ala Gly Leu Leu Pro Glu Thr Asp Ser Gln Asp Ile Val Ser Leu
                20                  25                  30

Ala Met Arg Glu Gly Val Met Ala Pro Gly Lys Arg Ile Arg Pro Leu
         35                  40                  45

Leu Met Leu Leu Ala Ala Arg Asp Leu Arg Tyr Gln Gly Ser Met Pro
 50                  55                  60

Thr Leu Leu Asp Leu Ala Cys Ala Val Glu Leu Thr His Thr Ala Ser
 65                  70                  75                  80

Leu Met Leu Asp Asp Met Pro Cys Met Asp Asn Ala Glu Leu Arg Arg
                85                  90                  95

Gly Gln Pro Thr Thr His Lys Lys Phe Gly Glu Ser Val Ala Ile Leu
                100                 105                 110

Ala Ser Val Gly Leu Leu Ser Lys Ala Phe Gly Leu Ile Ala Ala Thr
         115                 120                 125

Gly Asp Leu Pro Gly Glu Arg Arg Ala Gln Ala Val Asn Glu Leu Ser
 130                 135                 140

Thr Ala Val Gly Leu Gln Gly Leu Val Leu Gly Gln Phe Arg Asp Leu
145                  150                 155                 160

Asn Asp Ala Ala Leu Asp Arg Thr Pro Asp Ala Ile Leu Ser Thr Asn
                165                 170                 175

His Leu Lys Thr Gly Ile Leu Phe Ser Ala Met Leu Gln Ile Val Ala
                180                 185                 190

Ile Ala Ser Ala Ser Ser Pro Ser Thr Arg Glu Thr Leu His Ala Phe
         195                 200                 205

Ala Leu Asp Phe Gly Gln Ala Phe Gln Leu Leu Asp Asp Leu Arg Asp
 210                 215                 220

Asp His Pro Glu Thr Gly Lys Asp Arg Asn Lys Asp Ala Gly Lys Ser
225                  230                 235                 240

Thr Leu Val Asn Arg Leu Gly Ala Asp Ala Ala Arg Gln Lys Leu Arg
                245                 250                 255

Glu His Ile Asp Ser Ala Asp Lys His Leu Thr Phe Ala Cys Pro Gln
                260                 265                 270

Gly Gly Ala Ile Arg Gln Phe Met His Leu Trp Phe Gly His His Leu
         275                 280                 285

Ala Asp Trp Ser Pro Val Met Lys Ile Ala
```

( 2 ) INFORMATION FOR SEQ ID NO:5:

( i ) SEQUENCE CHARACTERISTICS:
        ( A ) LENGTH: 1198 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
                                                         GATTG AGGATCTGCA      15
ATGAGCCAAC CGCCGCTGCT TGACCACGCC ACGCAGACCA TGGCCAACGG CTCGAAAAGT              75
TTTGCCACCG CTGCGAAGCT GTTCGACCCG GCCACCCGCC GTAGCGTGCT GATGCTCTAC             135
ACCTGGTGCC GCCACTGCGA TGACGTCATT GACGACCAGA CCCACGGCTT CGCCAGCGAG             195
GCCGCGGCGG AGGAGGAGGC CACCCAGCGC CTGGCCCGGC TGCGCACGCT GACCCTGGCG             255
GCGTTTGAAG GGGCCGAGAT GCAGGATCCG GCCTTCGCTG CCTTTCAGGA GGTGGCGCTG             315
ACCCACGGTA TTACGCCCCG CATGGCGCTC GATCACCTCG ACGGCTTTGC GATGGACGTG             375
GCTCAGACCC GGTATGTCAC CTTTGAGGAT ACGCTGCGCT ACTGCTATCA CGTGGCGGGC             435
GTGGTGGGTC TGATGATGGC CAGGGTGATG GGCGTGCGGG ATGAGCGGGT GCTGGATCGC             495
GCCTGCGATC TGGGGCTGGC CTTCCAGCTG ACGAATATGG CCCGGGATAT TATTGACGAT             555
GCGGCTATTG ACCGCTGCTA TCTGCCCGCC GAGTGGCTGC AGGATGCCGG GCTGGCCCCG             615
GAGAACTATG CCGCGCGGGA GAATCGCCCC GCGCTGGCGC GGTGGCGGAG GCTTATTGAT             675
GCCGCAGAGC CGTACTACAT CTCCTCCCAG GCCGGGCTAC ACGATCTGCG GCGGCGCTCC             735
GCGTGGGCGA TCGCCACCGC CGCAGCGTC TACCGGGAGA TCGGTATTAA GGTAAAAGCG              795
GCGGGAGGCA GCGCCTGGGA TCGCCGCCAG CACACCAGCA AAGGTGAAAA AATTGCCATG             855
CTGATGGCGG CACCGGGGCA GGTTATTCGG GCGAAGACGA CGAGGGTGAC GCCGCGTCCG             915
GCCGGTCTTT GGCAGCGTCC CGTTTAGGCG GGCGGCCATG ACGTTCACGC AGGATCGCCT             975
GTAGGTCGGC AGGCTTGCGG GCGTAAATAA AACCGAAGGA GACGCAGCCC TCCCGGCCGC            1035
GCACCGCGTG GTGCAGGCGG TGGGCGACGT AGAGCCGCTT CAGGTAGCCC CGGCGCGGGA            1095
TCCAGTGGAA GGGCCAGCGC TGATGCACCA GACCGTCGTG CACCAGGAAG TAGAGCAGGC            1155
CATAGACCGT CATGCCGCAG CCAATCCACT GCAGGGGCCA AAC                             1198
```

( 2 ) INFORMATION FOR SEQ ID NO:6:

( i ) SEQUENCE CHARACTERISTICS:
        ( A ) LENGTH: 308 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ser Gln Pro Pro Leu Leu Asp His Ala Thr Gln Thr Met Ala Asn
 1               5                  10                  15
Gly Ser Lys Ser Phe Ala Thr Ala Ala Lys Leu Phe Asp Pro Ala Thr
            20                  25                  30
Arg Arg Ser Val Leu Met Leu Tyr Thr Trp Cys Arg His Cys Asp Asp
        35                  40                  45
Val Ile Asp Asp Gln Thr His Gly Phe Ala Ser Glu Ala Ala Ala Glu
    50                  55                  60
```

|     |     |     |     |     |     |     |     |     |     |     |     |     |     |     |     |
| --- | --- | --- | --- | --- | --- | --- | --- | --- | --- | --- | --- | --- | --- | --- | --- |
| Glu | Glu | Ala | Thr | Gln | Arg | Leu | Ala | Arg | Leu | Arg | Thr | Leu | Thr | Leu | Ala |
| 65  |     |     |     | 70  |     |     |     |     | 75  |     |     |     |     |     | 80  |
| Ala | Phe | Glu | Gly | Ala | Glu | Met | Gln | Asp | Pro | Ala | Phe | Ala | Ala | Phe | Gln |
|     |     |     |     | 85  |     |     |     |     | 90  |     |     |     |     | 95  |     |
| Glu | Val | Ala | Leu | Thr | His | Gly | Ile | Thr | Pro | Arg | Met | Ala | Leu | Asp | His |
|     |     |     |     | 100 |     |     |     |     | 105 |     |     |     | 110 |     |     |
| Leu | Asp | Gly | Phe | Ala | Met | Asp | Val | Ala | Gln | Thr | Arg | Tyr | Val | Thr | Phe |
|     |     | 115 |     |     |     |     | 120 |     |     |     |     | 125 |     |     |     |
| Glu | Asp | Thr | Leu | Arg | Tyr | Cys | Tyr | His | Val | Ala | Gly | Val | Val | Gly | Leu |
|     | 130 |     |     |     |     | 135 |     |     |     |     | 140 |     |     |     |     |
| Met | Met | Ala | Arg | Val | Met | Gly | Val | Arg | Asp | Glu | Arg | Val | Leu | Asp | Arg |
| 145 |     |     |     |     | 150 |     |     |     |     | 155 |     |     |     |     | 160 |
| Ala | Cys | Asp | Leu | Gly | Leu | Ala | Phe | Gln | Leu | Thr | Asn | Met | Ala | Arg | Asp |
|     |     |     |     | 165 |     |     |     |     | 170 |     |     |     |     | 175 |     |
| Ile | Ile | Asp | Asp | Ala | Ala | Ile | Asp | Arg | Cys | Tyr | Leu | Pro | Ala | Glu | Trp |
|     |     |     | 180 |     |     |     |     | 185 |     |     |     |     | 190 |     |     |
| Leu | Gln | Asp | Ala | Gly | Leu | Ala | Pro | Glu | Asn | Tyr | Ala | Ala | Arg | Glu | Asn |
|     |     | 195 |     |     |     |     | 200 |     |     |     |     | 205 |     |     |     |
| Arg | Pro | Ala | Leu | Ala | Arg | Trp | Arg | Arg | Leu | Ile | Asp | Ala | Ala | Glu | Pro |
|     | 210 |     |     |     |     | 215 |     |     |     |     | 220 |     |     |     |     |
| Tyr | Tyr | Ile | Ser | Ser | Gln | Ala | Gly | Leu | His | Asp | Leu | Arg | Arg | Arg | Ser |
| 225 |     |     |     |     | 230 |     |     |     |     | 235 |     |     |     |     | 240 |
| Ala | Trp | Ala | Ile | Ala | Thr | Ala | Arg | Ser | Val | Tyr | Arg | Glu | Ile | Gly | Ile |
|     |     |     |     | 245 |     |     |     |     | 250 |     |     |     |     | 255 |     |
| Lys | Val | Lys | Ala | Ala | Gly | Gly | Ser | Ala | Trp | Asp | Arg | Arg | Gln | His | Thr |
|     |     |     | 260 |     |     |     |     | 265 |     |     |     |     | 270 |     |     |
| Ser | Lys | Gly | Glu | Lys | Ile | Ala | Met | Leu | Met | Ala | Ala | Pro | Gly | Gln | Val |
|     |     | 275 |     |     |     |     | 280 |     |     |     |     | 285 |     |     |     |
| Ile | Arg | Ala | Lys | Thr | Thr | Arg | Val | Thr | Pro | Arg | Pro | Ala | Gly | Leu | Trp |
|     | 290 |     |     |     |     | 295 |     |     |     |     | 300 |     |     |     |     |
| Gln | Arg | Pro | Val |     |     |     |     |     |     |     |     |     |     |     |     |
| 305 |     |     |     |     |     |     |     |     |     |     |     |     |     |     |     |

( 2 ) INFORMATION FOR SEQ ID NO:7:

( i ) SEQUENCE CHARACTERISTICS:
         ( A ) LENGTH: 1518 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:7:

```
                                                                    TAAACC       6
ATGGAAAAAA  CCGTTGTGAT  TGGCGCAGGC  TTTGGTGGCC  TGGCGCTGGC  GATTCGCCTG     66
CAGGCGGCAG  GGATCCCAAC  CGTACTGCTG  GAGCAGCGGG  ACAAGCCCGG  CGGTCGGGCC    126
TACGTCTGGC  ATGACCAGGG  CTTTACCTTT  GACGCCGGGC  CGACGGTGAT  CACCGATCCT    186
ACCGCGCTTG  AGGCGCTGTT  CACCCTGGCC  GGCAGGCGCA  TGGAGGATTA  CGTCAGGCTG    246
CTGCCGGTAA  AACCCTTCTA  CCGACTCTGC  TGGGAGTCCG  GAAGACCCT   CGACTATGCT    306
AACGACAGCT  TCGAGCTTGA  GGCGCAGATT  ACCCAGTTCA  ACCCCGCGA   CGTCGAGGGC    366
TACCGGCGCT  TTCTGGCTTA  CTCCCAGGCG  GTATTCCAGG  AGGGATATTT  GCGCCTCGGC    426
AGCGTGCCGT  TCCTCTCTTT  TCGCGACATG  CTGCGCGCCG  GGCCGCAGCT  GCTTAAGCTC    486
```

-continued

```
CAGGCGTGGC AGAGCGTCTA CCAGTCGGTT TCGCGCTTTA TTGAGGATGA GCATCTGCGG      546
CAGGCCTTCT CGTTCCACTC CCTGCTGGTA GGCGGCAACC CCTTCACCAC CTCGTCCATC      606
TACACCCTGA TCCACGCCCT TGAGCGGGAG TGGGGGGTCT GGTTCCCTGA GGGCGGCACC      666
GGGGCGCTGG TGAACGGCAT GGTGAAGCTG TTTACCGATC TGGGCGGGGA GATCGAACTC      726
AACGCCCGGG TCGAAGAGCT GGTGGTGGCC GATAACCGCG TAAGCCAGGT CCGGCTCGCG      786
GATGGTCGGA TCTTTGACAC CGACGCCGTA GCCTCGAACG CTGACGTGGT GAACACCTAT      846
AAAAAGCTGC TCGGCACCAT ACCGGTGGGG CAGAAGCGGG CGGCACGGCT GGAGCGCAAG      906
AGCATGAGCA ACTCGCTGTT TGTGCTCTAC TTCGGCCTGA ACCAGCCTCA TTCCCAGCTG      966
GCGCACCATA CCATCTGTTT TGGTCCCCGC TACCGGGAGC TGATCGACGA GATCTTTACC     1026
GGCAGCGCGC TGGCGGATGA CTTCTCGCTC TACCTGCACT CGCCCTGCGT GACCGATCCC     1086
TCGCTCGCGC CTCCCCCGTG CGCCAGCTTC TACGTGCTGG CCCCGGTGCC GCATCTTGGC     1146
AACGCGCCGC TGGACTGGGC GCAGGAGGGG CCGAAGCTGC GCGACCGCAT CTTTGACTAC     1206
CTTGAAGAGC GCTATATGCC CGGCCTGCGT AGCCAGCTGG TGACCCAGCG GATCTTTACC     1266
CGGCAGACTT CACGACACGC TTGGATCGCG ATCTTGGGAT CGCTTTTCAT CGAGCCGCCT     1326
TCGTTGACCC AAGGCTTGTT CGCCGCAAAC GCGACACGAC ATTCAAACCT CTACCTGGTG     1386
GCCGCAGGTA CTCACCCTGG CGCGGGCATT CCTGGCGTAG TGGGCCTCGC CGAAAGCACC     1446
GCCAGCCTGA TGATTGAGGA TCTGCAATGA GCCAACCGCC GCTGCTTGAC CACGCCACGC     1506
AGACCATGGC CA                                                        1518
```

( 2 ) INFORMATION FOR SEQ ID NO:8:

( i ) SEQUENCE CHARACTERISTICS:
( A ) LENGTH: 489 amino acids
( B ) TYPE: amino acid
( D ) TOPOLOGY: linear ( i i ) MOLECULE TYPE: protein ( x i ) SEQUENCE DESCRIPTION: SEQ ID NO:8:

```
Met Lys Lys Thr Val Val Ile Gly Ala Gly Phe Gly Gly Leu Ala Leu
 1               5                  10                  15

Ala Ile Arg Leu Gln Ala Ala Gly Ile Pro Thr Val Leu Leu Glu Gln
            20                  25                  30

Arg Asp Lys Pro Gly Gly Arg Ala Tyr Val Trp His Asp Gln Gly Phe
        35                  40                  45

Thr Phe Asp Ala Gly Pro Thr Val Ile Thr Asp Pro Thr Ala Leu Glu
    50                  55                  60

Ala Leu Phe Thr Leu Ala Gly Arg Arg Met Glu Asp Tyr Val Arg Leu
65                  70                  75                  80

Leu Pro Val Lys Pro Phe Tyr Arg Leu Cys Trp Glu Ser Gly Lys Thr
                85                  90                  95

Leu Asp Tyr Ala Asn Asp Ser Phe Glu Leu Glu Ala Gln Ile Thr Gln
           100                 105                 110

Phe Asn Pro Arg Asp Val Glu Gly Tyr Arg Arg Phe Leu Ala Tyr Ser
       115                 120                 125

Gln Ala Val Phe Gln Glu Gly Tyr Leu Arg Leu Gly Ser Val Pro Phe
   130                 135                 140

Leu Ser Phe Arg Asp Met Leu Arg Ala Gly Pro Gln Leu Leu Lys Leu
145                 150                 155                 160

Gln Ala Trp Gln Ser Val Tyr Gln Ser Val Ser Arg Phe Ile Glu Asp
               165                 170                 175
```

```
Glu  His  Leu  Arg  Gln  Ala  Phe  Ser  Phe  His  Ser  Leu  Leu  Val  Gly  Gly
          180                      185                          190

Asn  Pro  Phe  Thr  Thr  Ser  Ser  Ile  Tyr  Thr  Leu  Ile  His  Ala  Leu  Glu
          195                      200                          205

Arg  Glu  Trp  Gly  Val  Trp  Phe  Pro  Glu  Gly  Gly  Thr  Gly  Ala  Leu  Val
          210                      215                          220

Asn  Gly  Met  Val  Lys  Leu  Phe  Thr  Asp  Leu  Gly  Gly  Glu  Ile  Glu  Leu
225                           230                     235                      240

Asn  Ala  Arg  Val  Glu  Glu  Leu  Val  Val  Ala  Asp  Asn  Arg  Val  Ser  Gln
                    245                      250                     255

Val  Arg  Leu  Ala  Asp  Gly  Arg  Ile  Phe  Asp  Thr  Asp  Ala  Val  Ala  Ser
               260                      265                     270

Asn  Ala  Asp  Val  Val  Asn  Thr  Tyr  Lys  Lys  Leu  Leu  Gly  Thr  Ile  Pro
          275                      280                          285

Val  Gly  Gln  Lys  Arg  Ala  Ala  Arg  Leu  Glu  Arg  Lys  Ser  Met  Ser  Asn
     290                      295                     300

Ser  Leu  Phe  Val  Leu  Tyr  Phe  Gly  Leu  Asn  Gln  Pro  His  Ser  Gln  Leu
305                      310                     315                          320

Ala  His  His  Thr  Ile  Cys  Phe  Gly  Pro  Arg  Tyr  Arg  Glu  Leu  Ile  Asp
                    325                      330                          335

Glu  Ile  Phe  Thr  Gly  Ser  Ala  Leu  Ala  Asp  Asp  Phe  Ser  Leu  Tyr  Leu
                    340                     345                     350

His  Ser  Pro  Cys  Val  Thr  Asp  Pro  Ser  Leu  Ala  Pro  Pro  Cys  Ala
          355                      360                     365

Ser  Phe  Tyr  Val  Leu  Ala  Pro  Val  Pro  His  Leu  Gly  Asn  Ala  Pro  Leu
     370                      375                     380

Asp  Trp  Ala  Gln  Glu  Gly  Pro  Lys  Leu  Arg  Asp  Arg  Ile  Phe  Asp  Tyr
385                      390                           395                      400

Leu  Glu  Glu  Arg  Tyr  Met  Pro  Gly  Leu  Arg  Ser  Gln  Leu  Val  Thr  Gln
               405                      410                          415

Arg  Ile  Phe  Thr  Arg  Gln  Thr  Ser  Arg  His  Ala  Trp  Ile  Ala  Ile  Leu
               420                      425                          430

Gly  Ser  Leu  Phe  Ile  Glu  Pro  Pro  Ser  Leu  Thr  Gln  Gly  Leu  Phe  Ala
          435                      440                          445

Ala  Asn  Ala  Thr  Arg  His  Ser  Asn  Leu  Tyr  Leu  Val  Ala  Ala  Gly  Thr
     450                           455                     460

His  Pro  Gly  Ala  Gly  Ile  Pro  Gly  Val  Val  Gly  Leu  Ala  Glu  Ser  Thr
465                      470                     475                          480

Ala  Ser  Leu  Met  Ile  Glu  Asp  Leu  Gln
               485
```

( 2 ) INFORMATION FOR SEQ ID NO:9:

( i ) SEQUENCE CHARACTERISTICS:
        ( A ) LENGTH: 1522 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
                                                            GAGGTCGACG    10
ATGGAAAAAA  CCGTTGTGAT  TGGCGCAGGC  TTTGGTGGCC  TGGCGCTGGC  GATTCGCCTG    70
CAGGCGGCAG  GGATCCCAAC  CGTACTGCTG  GAGCAGCGGG  ACAAGCCCGG  CGGTCGGGCC   130
```

-continued

```
TACGTCTGGC ATGACCAGGG CTTTACCTTT GACGCCGGGC CGACGGTGAT CACCGATCCT    190
ACCGCGCTTG AGGCGCTGTT CACCCTGGCC GGCAGGCGCA TGGAGGATTA CGTCAGGCTG    250
CTGCCGGTAA AACCCTTCTA CCGACTCTGC TGGGAGTCCG GAAGACCCT CGACTATGCT     310
AACGACAGCT TCGAGCTTGA GGCGCAGATT ACCCAGTTCA ACCCCGCGA CGTCGAGGGC     370
TACCGGCGCT TTCTGGCTTA CTCCCAGGCG GTATTCCAGG AGGGATATTT GCGCCTCGGC    430
AGCGTGCCGT TCCTCTCTTT TCGCGACATG CTGCGCGCCG GCCGCAGCT GCTTAAGCTC     490
CAGGCGTGGC AGAGCGTCTA CCAGTCGGTT TCGCGCTTTA TTGAGGATGA GCATCTGCGG    550
CAGGCCTTCT CGTTCCACTC CCTGCTGGTA GGCGGCAACC CCTTCACCAC CTCGTCCATC    610
TACACCCTGA TCCACGCCCT TGAGCGGGAG TGGGGGGTCT GGTTCCCTGA GGGCGGCACC    670
GGGGCGCTGG TGAACGGCAT GGTGAAGCTG TTTACCGATC TGGGCGGGGA GATCGAACTC    730
AACGCCCGGG TCGAAGAGCT GGTGGTGGCC GATAACCGCG TAAGCCAGGT CCGGCTCGCG    790
GATGGTCGGA TCTTTGACAC CGACGCCGTA GCCTCGAACG CTGACGTGGT GAACACCTAT    850
AAAAAGCTGC TCGGCACCAT ACCGGTGGGG CAGAAGCGGG CGGCACGGCT GGAGCGCAAG    910
AGCATGAGCA ACTCGCTGTT TGTGCTCTAC TTCGGCCTGA CCAGCCTCA TTCCCAGCTG     970
GCGCACCATA CCATCTGTTT TGGTCCCCGC TACCGGGAGC TGATCGACGA GATCTTTACC   1030
GGCAGCGCGC TGGCGGATGA CTTCTCGCTC TACCTGCACT CGCCCTGCGT GACCGATCCC   1090
TCGCTCGCGC CTCCCCCGTG CGCCAGCTTC TACGTGCTGG CCCCGGTGCC GCATCTTGGC   1150
AACGCGCCGC TGGACTGGGC GCAGGAGGGG CCGAAGCTGC GCGACCGCAT CTTTGACTAC   1210
CTTGAAGAGC GCTATATGCC CGGCCTGCGT AGCCAGCTGG TGACCCAGCG GATCTTTACC   1270
CGGCAGACTT CACGACACGC TTGGATCGCG ATCTTGGGAT CGCTTTTCAT CGAGCCGCCT   1330
TCGTTGACCC AAGGCTTGTT CGCCGCAAAC GCGACACGAC ATTCAAACCT CTACCTGGTG   1390
GCCGCAGGTA CTCACCCTGG CGCGGGCATT CCTGGCGTAG TGGGCCTCGC CGAAAGCACC   1450
GCCAGCCTGA TGATTGAGGA TCTGCAATGA GCCAACCGCC GCTGCTTGAC CACGCCACGT   1510
CGACCATGGC CA                                                       1522
```

( 2 ) INFORMATION FOR SEQ ID NO:10:

( i ) SEQUENCE CHARACTERISTICS:
( A ) LENGTH: 489 amino acids
( B ) TYPE: amino acid
( D ) TOPOLOGY: linear ( i i ) MOLECULE TYPE: protein ( x i ) SEQUENCE DESCRIPTION: SEQ ID NO:10:

```
Met Glu Lys Thr Val Val Ile Gly Ala Gly Phe Gly Gly Leu Ala Leu
 1               5                  10                  15

Ala Ile Arg Leu Gln Ala Ala Gly Ile Pro Thr Val Leu Leu Glu Gln
            20                  25                  30

Arg Asp Lys Pro Gly Gly Arg Ala Tyr Val Trp His Asp Gln Gly Phe
        35                  40                  45

Thr Phe Asp Ala Gly Pro Thr Val Ile Thr Asp Pro Thr Ala Leu Glu
    50                  55                  60

Ala Leu Phe Thr Leu Ala Gly Arg Arg Met Glu Asp Tyr Val Arg Leu
65                  70                  75                  80

Leu Pro Val Lys Pro Phe Tyr Arg Leu Cys Trp Glu Ser Gly Lys Thr
                85                  90                  95

Leu Asp Tyr Ala Asn Asp Ser Phe Glu Leu Glu Ala Gln Ile Thr Gln
            100                 105                 110
```

```
Phe  Asn  Pro  Arg  Asp  Val  Glu  Gly  Tyr  Arg  Arg  Phe  Leu  Ala  Tyr  Ser
          115                      120                      125
Gln  Ala  Val  Phe  Gln  Glu  Gly  Tyr  Leu  Arg  Leu  Gly  Ser  Val  Pro  Phe
          130                      135                      140
Leu  Ser  Phe  Arg  Asp  Met  Leu  Arg  Ala  Gly  Pro  Gln  Leu  Leu  Lys  Leu
145                      150                      155                      160
Gln  Ala  Trp  Gln  Ser  Val  Tyr  Gln  Ser  Val  Ser  Arg  Phe  Ile  Glu  Asp
               165                      170                      175
Glu  His  Leu  Arg  Gln  Ala  Phe  Ser  Phe  His  Ser  Leu  Leu  Val  Gly  Gly
               180                      185                      190
Asn  Pro  Phe  Thr  Thr  Ser  Ser  Ile  Tyr  Thr  Leu  Ile  His  Ala  Leu  Glu
          195                      200                      205
Arg  Glu  Trp  Gly  Val  Trp  Phe  Pro  Glu  Gly  Gly  Thr  Gly  Ala  Leu  Val
     210                      215                      220
Asn  Gly  Met  Val  Lys  Leu  Phe  Thr  Asp  Leu  Gly  Gly  Glu  Ile  Glu  Leu
225                      230                      235                      240
Asn  Ala  Arg  Val  Glu  Glu  Leu  Val  Val  Ala  Asp  Asn  Arg  Val  Ser  Gln
               245                                250                 255
Val  Arg  Leu  Ala  Asp  Gly  Arg  Ile  Phe  Asp  Thr  Asp  Ala  Val  Ala  Ser
               260                      265                      270
Asn  Ala  Asp  Val  Val  Asn  Thr  Tyr  Lys  Lys  Leu  Leu  Gly  Thr  Ile  Pro
          275                      280                      285
Val  Gly  Gln  Lys  Arg  Ala  Ala  Arg  Leu  Glu  Arg  Lys  Ser  Met  Ser  Asn
     290                      295                      300
Ser  Leu  Phe  Val  Leu  Tyr  Phe  Gly  Leu  Asn  Gln  Pro  His  Ser  Gln  Leu
305                      310                      315                      320
Ala  His  His  Thr  Ile  Cys  Phe  Gly  Pro  Arg  Tyr  Arg  Glu  Leu  Ile  Asp
               325                      330                      335
Glu  Ile  Phe  Thr  Gly  Ser  Ala  Leu  Ala  Asp  Asp  Phe  Ser  Leu  Tyr  Leu
               340                      345                      350
His  Ser  Pro  Cys  Val  Thr  Asp  Pro  Ser  Leu  Ala  Pro  Pro  Cys  Ala
          355                      360                      365
Ser  Phe  Tyr  Val  Leu  Ala  Pro  Val  Pro  His  Leu  Gly  Asn  Ala  Pro  Leu
     370                      375                      380
Asp  Trp  Ala  Gln  Glu  Gly  Pro  Lys  Leu  Arg  Asp  Arg  Ile  Phe  Asp  Tyr
385                      390                      395                      400
Leu  Glu  Glu  Arg  Tyr  Met  Pro  Gly  Leu  Arg  Ser  Gln  Leu  Val  Thr  Gln
                    405                      410                      415
Arg  Ile  Phe  Thr  Arg  Gln  Thr  Ser  Arg  His  Ala  Trp  Ile  Ala  Ile  Leu
               420                      425                      430
Gly  Ser  Leu  Phe  Ile  Glu  Pro  Pro  Ser  Leu  Thr  Gln  Gly  Leu  Phe  Ala
          435                      440                      445
Ala  Asn  Ala  Thr  Arg  His  Ser  Asn  Leu  Tyr  Leu  Val  Ala  Ala  Gly  Thr
     450                      455                      460
His  Pro  Gly  Ala  Gly  Ile  Pro  Gly  Val  Val  Gly  Leu  Ala  Glu  Ser  Thr
465                      470                      475                      480
Ala  Ser  Leu  Met  Ile  Glu  Asp  Leu  Gln
                    485
```

( 2 ) INFORMATION FOR SEQ ID NO:11:

( i ) SEQUENCE CHARACTERISTICS:
        ( A ) LENGTH: 59 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

| Met | Ala | Ser | Ser | Val | Leu | Ser | Ser | Ala | Ala | Val | Ala | Thr | Arg | Ser | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Ala | Gln | Ala | Asn | Met | Val | Ala | Pro | Phe | Thr | Gly | Leu | Lys | Ser | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | Ser | Phe | Pro | Val | Ser | Arg | Lys | Gln | Asn | Leu | Asp | Ile | Thr | Ser | Ile |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ala | Ser | Asn | Gly | Gly | Arg | Val | Gln | Cys | Met | Gln |
|-----|-----|-----|-----|-----|-----|-----|-----|-----|-----|-----|
|     |     | 50  |     |     |     | 55  |     |     |     |     |

( 2 ) INFORMATION FOR SEQ ID NO:12:

( i ) SEQUENCE CHARACTERISTICS:
      ( A ) LENGTH: 177 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:12:

```
ATGGCTTCCT CAGTTCTTTC CTCTGCAGCA GTTGCCACCC GCAGCAATGT TGCTCAAGCT      60
AACATGGTGG CGCCTTTCAC TGGCCTTAAG TCAGCTGCCT CATTCCCTGT TTCAAGGAAG     120
CAAAACCTTG ACATCACTTC CATTGCCAGC AACGGCGGAA GAGTGCAATG CATGCAG       177
```

( 2 ) INFORMATION FOR SEQ ID NO:13:

( i ) SEQUENCE CHARACTERISTICS:
      ( A ) LENGTH: 1235 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:13:

```
                                                  CAGGGAGTG AGAGCGTATC      19
GTGAGGGATC TGATTTTAGT CGGCGGCGGC CTGGCCAACG GGCTGATCGC CTGGCGTCTG      79
CGCCAGCGCT ACCCGCAGCT TAACCTGCTG CTGATCGAGG CCGGGGAGCA GCCCGGCGGG     139
AACCATACCT GGTCATTCCA TGAAGACGAT CTGACTCCCG GGCAGCACGC CTGGCTGGCC     199
CCGCTGGTGG CCCACGCCTG GCCGGGCTAT GAGGTGCAGT TCCCGATCT TCGCCGTCGC     259
CTCGCGCGCG GCTACTACTC CATTACCTCA GAGCGCTTTG CCGAGGCCCT GCATCAGGCG     319
CTGGGGAGA ACATCTGGCT AAACTGTTCG GTGAGCGAGG TGTTACCCAA TAGCGTGCGC     379
CTTGCCAACG GTGAGGCGCT GCTTGCCGGA GCGGTGATTG ACGGACGCGG CGTGACCGCC     439
AGTTCGGCGA TGCAAACCGG CTATCAGCTC TTTCTTGGTC AGCAGTGGCG GCTGACACAG     499
CCCCACGGCC TGACCGTACC GATCCTGATG GATGCCACGG TGGCGCAGCA GCAGGGCTAT     559
CGCTTTGTCT ACACGCTGCC GCTCTCCGCC GACACGCTGC TGATCGAGGA TACGCGCTAC     619
GCCAATGTCC CGCAGCGTGA TGATAATGCC CTACGCCAGA CGGTTACCGA CTATGCTCAC     679
AGCAAAGGGT GGCAGCTGGC CCAGCTTGAA CGCGAGGAGA CCGGCTGTCT GCCGATTACC     739
TGGCGGGTGA CATCCAGGCT CTGTGGGCCG ATGCGCCGGC GTGCCGCGTC GGGAATGCGG     799
GCTGGGCTAT TTCACCCTAC CACTGGCTAT TCGCTGCCGC TGGCGGTGGC CCTTGCCGAC     859
GCGATTGCCG ACAGCCCGCG GCTGGGCAGC GTTCCGCTCT ATCAGCTCAC CCGGCAGTTT     919
```

```
GCCGAACGCC ACTGGCGCAG GCAGGGATTC TTCCGCCTGC TGAACCGGAT GCTTTTCCTG    979

GCCGGGCGCG AGGAGAACCG CTGGCGGGTG ATGCAGCGCT TTTATGGGCT GCCGGAGCCC   1039

ACCGTAGAGC GCTTTTACGC CGGTCGGCTC TCTCTCTTTG ATAAGGCCCG CATTTTGACG   1099

GGCAAGCCAC CGGTTCCGCT GGCGAAGTCT GGCGGGCGGC GCTGAACCAT TTTCCTGACA   1159

GACGAGATAA AGGATGAAAA AAACCGTTGT GATTGGCGCA GGCTTTGGTG GCCTGGCGCT   1219

GGCGATTCGC CTGCAG                                                   1235
```

( 2 ) INFORMATION FOR SEQ ID NO:14:

( i ) SEQUENCE CHARACTERISTICS:
        ( A ) LENGTH: 374 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Arg Asp Leu Ile Leu Val Gly Gly Gly Leu Ala Asn Gly Leu Ile
  1           5                  10                  15

Ala Trp Arg Leu Arg Gln Arg Tyr Pro Gln Leu Asn Leu Leu Leu Ile
             20                  25                  30

Glu Ala Gly Glu Gln Pro Gly Gly Asn His Thr Trp Ser Phe His Glu
             35                  40                  45

Asp Asp Leu Thr Pro Gly Gln His Ala Trp Leu Ala Pro Leu Val Ala
 50                  55                  60

His Ala Trp Pro Gly Tyr Glu Val Gln Phe Pro Asp Leu Arg Arg Arg
 65                  70                  75                  80

Leu Ala Arg Gly Tyr Tyr Ser Ile Thr Ser Glu Arg Phe Ala Glu Ala
                 85                  90                  95

Leu His Gln Ala Leu Gly Glu Asn Ile Trp Leu Asn Cys Ser Val Ser
            100                 105                 110

Glu Val Leu Pro Asn Ser Val Arg Leu Ala Asn Gly Glu Ala Leu Leu
            115                 120                 125

Ala Gly Ala Val Ile Asp Gly Arg Gly Val Thr Ala Ser Ser Ala Met
130                 135                 140

Gln Thr Gly Tyr Gln Leu Phe Leu Gly Gln Gln Trp Arg Leu Thr Gln
145                 150                 155                 160

Pro His Gly Leu Thr Val Pro Ile Leu Met Asp Ala Thr Val Ala Gln
                165                 170                 175

Gln Gln Gly Tyr Arg Phe Val Tyr Thr Leu Pro Leu Ser Ala Asp Thr
            180                 185                 190

Leu Leu Ile Glu Asp Thr Arg Tyr Ala Asn Val Pro Gln Arg Asp Asp
            195                 200                 205

Asn Ala Leu Arg Gln Thr Val Thr Asp Tyr Ala His Ser Lys Gly Trp
        210                 215                 220

Gln Leu Ala Gln Leu Glu Arg Glu Glu Thr Gly Cys Leu Pro Ile Thr
225                 230                 235                 240

Trp Arg Val Thr Ser Arg Leu Cys Gly Pro Met Arg Arg Arg Ala Ala
                245                 250                 255

Ser Gly Met Arg Ala Gly Leu Phe His Pro Thr Thr Gly Tyr Ser Leu
            260                 265                 270

Pro Leu Ala Val Ala Leu Ala Asp Ala Ile Ala Asp Ser Pro Arg Leu
            275                 280                 285

Gly Ser Val Pro Leu Tyr Gln Leu Thr Arg Gln Phe Ala Glu Arg His
```

```
                              290                           295                           300
            Trp  Arg  Arg  Gln  Gly  Phe  Phe  Arg  Leu  Leu  Asn  Arg  Met  Leu  Phe  Leu
            305                           310                           315                      320

Ala  Gly  Arg  Glu  Glu  Asn  Arg  Trp  Arg  Val  Met  Gln  Arg  Phe  Tyr  Gly
                                325                           330                           335

Leu  Pro  Glu  Pro  Thr  Val  Glu  Arg  Phe  Tyr  Ala  Gly  Arg  Leu  Ser  Leu
                                340                           345                           350

Phe  Asp  Lys  Ala  Arg  Ile  Leu  Thr  Gly  Lys  Pro  Pro  Val  Pro  Leu  Ala
                                355                           360                           365

Lys  Ser  Gly  Gly  Arg  Arg
                                370
```

( 2 ) INFORMATION FOR SEQ ID NO:15:

( i ) SEQUENCE CHARACTERISTICS:
        ( A ) LENGTH: 1235 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
                                                              CAGGGAGTG   AGAGGCGCGC     19
ATGCGGGATC   TGATTTTAGT   CGGCCGCGGC   CTGGCCAACG   GGCTGATCGC   CTGGCGTCTG     79
CGCCAGCGCT   ACCCGCAGCT   TAACCTGCTG   CTGATCGAGG   CCGGGGAGCA   GCCCGGCGGG    139
AACCATACCT   GGTCATTCCA   TGAAGACGAT   CTGACTCCCG   GGCAGCACGC   CTGGCTGGCC    199
CCGCTGGTGG   CCCACGCCTG   GCCGGGCTAT   GAGGTGCAGT   TTCCCGATCT   TCGCCGTCGC    259
CTCGCGCGCG   GCTACTACTC   CATTACCTCA   GAGCGCTTTG   CCGAGGCCCT   GCATCAGGCG    319
CTGGGGGAGA   ACATCTGGCT   AAACTGTTCG   GTGAGCGAGG   TGTTACCCAA   TAGCGTGCGC    379
CTTGCCAACG   GTGAGGCGCT   GCTTGCCGGA   GCGGTGATTG   ACGGACGCGG   CGTGACCGCC    439
AGTTCGGCGA   TGCAAACCGG   CTATCAGCTC   TTTCTTGGTC   AGCAGTGGCG   GCTGACACAG    499
CCCCACGGCC   TGACCGTACC   GATCCTGATG   GATGCCACGG   TGGCGCAGCA   GCAGGGCTAT    559
CGCTTTGTCT   ACACGCTGCC   GCTCTCCGCC   GACACGCTGC   TGATCGAGGA   TACGCGCTAC    619
GCCAATGTCC   CGCAGCGTGA   TGATAATGCC   CTACGCCAGA   CGGTTACCGA   CTATGCTCAC    679
AGCAAAGGGT   GGCAGCTGGC   CCAGCTTGAA   CGCGAGGAGA   CCGGCTGTCT   GCCGATTACC    739
TGGCGGGTGA   CATCCAGGCT   CTGTGGGCCG   ATGCGCCGGC   GTGCCGCGTC   GGGAATGCGG    799
GCTGGGCTAT   TTCACCCTAC   CACTGGCTAT   TCGCTGCCGC   TGGCGGTGGC   CCTTGCCGAC    859
GCGATTGCCG   ACAGCCCGCG   GCTGGGCAGC   GTTCCGCTCT   ATCAGCTCAC   CCGGCAGTTT    919
GCCGAACGCC   ACTGGCGCAG   GCAGGGATTC   TTCCGCCTGC   TGAACCGGAT   GCTTTTCCTG    979
GCCGGGCGCG   AGGAGAACCG   CTGGCGGGTG   ATGCAGCGCT   TTTATGGGCT   GCCGGAGCCC   1039
ACCGTAGAGC   GCTTTTACGC   CGGTCGGCTC   TCTCTCTTTG   ATAAGGCCCG   CATTTTGACG   1099
GGCAAGCCAC   CGGTTCCGCT   GGCGAAGTCT   GGCGGGCGGC   GCTGAACCAT   TTTCCTGACA   1159
GACGAGATAA   AGGGATCCGA   TGACCGTTGT   GATTGGCGCA   GGCTTTGGTG   GCCTGGCGCT   1219
GGCGATTCGC   CTGCAG                                                          1235
```

( 2 ) INFORMATION FOR SEQ ID NO:16:

( i ) SEQUENCE CHARACTERISTICS:
        ( A ) LENGTH: 39 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

TCAGCGGGTA ACCTTGCCAT GGGGAGTGGC AGTAAAGCG 39

( 2 ) INFORMATION FOR SEQ ID NO:17:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

TTGCAATGGT GA 12

( 2 ) INFORMATION FOR SEQ ID NO:18:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

TTGCCATGGG GA 12

( 2 ) INFORMATION FOR SEQ ID NO:19:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

CATGGCGAAA TAGAAGCCAT GGGACAATCC ATTGACGAT 39

( 2 ) INFORMATION FOR SEQ ID NO:20:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

AAGTAATGAG AC 12

( 2 ) INFORMATION FOR SEQ ID NO:21:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

AAGCCATGGG AC  12

( 2 ) INFORMATION FOR SEQ ID NO:22:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

Met Val Ser Gly Ser Lys Ala Gly Val Ser Pro His Arg Glu Ile
1               5                   10                  15

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

Met Ala Glu Phe Glu Ile
1               5

( 2 ) INFORMATION FOR SEQ ID NO:24:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

TAAGCATGCT CGAATTCGAA ATAGAAGTAA TG  32

( 2 ) INFORMATION FOR SEQ ID NO:25:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

CCGCGCATGC GACCCTTGTG TATCAAACAA G  31

( 2 ) INFORMATION FOR SEQ ID NO:26:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

CTTGTTTGAT ACACAAGGGT CGCATCTGCG G  31

( 2 ) INFORMATION FOR SEQ ID NO:27:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

CTTGTTTGAT ACACAAGGGT CGCATGCGCG G    31

( 2 ) INFORMATION FOR SEQ ID NO:28:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

CATGGCTTCC TCAGTTCTTT CCTCTGCAGC AGTTGCC    37

( 2 ) INFORMATION FOR SEQ ID NO:29:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

GGGTGGCAAC TGCTGCAGAG GAAAGAACTG AGGAAGC    37

( 2 ) INFORMATION FOR SEQ ID NO:30:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

ACCCGCAGCA ATGTTGCTCA AGCTAACATG GTGG    34

( 2 ) INFORMATION FOR SEQ ID NO:31:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

CGCCACCATG TTAGCTTGAG CAACATTGCT GC    32

( 2 ) INFORMATION FOR SEQ ID NO:32:

( i ) SEQUENCE CHARACTERISTICS:
        ( A ) LENGTH: 50 base pairs
        ( B ) TYPE: nucleic acid (C) STRANDEDNESS: single
(D) TOPOLOGY: linear (i i) MOLECULE TYPE: DNA (genomic)

(x i) SEQUENCE DESCRIPTION: SEQ ID NO:32:

CGCCTTTCAC TGGCCTTAAG TCAGCTGCCT CATTCCCTGT TTCAAGGAAG 50

(2) INFORMATION FOR SEQ ID NO:33:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:33:

TTTGCTTCCT TGAAACAGGG AATGAGGCAG CGAATGAGGC AGCTGACTTA AGGCCAGTCA 60

AAGG 64

(2) INFORMATION FOR SEQ ID NO:34:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:34:

CAAAACCTTG ACATCACTTC CATTGCCAGC AACGGCGGAA GAGTGCAATG CATG 54

(2) INFORMATION FOR SEQ ID NO:35:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:35:

CATTGCACTC TTCCGCCGTT GCTGGCAATG GAAGTGATGT CAAGGT 46

(2) INFORMATION FOR SEQ ID NO:36:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:36:

CATGGCTTCC TCAGTTCTTT CCTCTGCAGC AGTTGCCACC CGCAGCAATG TTGCTCAAGC 60

TAACATGGTG G 71

(2) INFORMATION FOR SEQ ID NO:37:

(i) SEQUENCE CHARACTERISTICS:
        (A) LENGTH: 68 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:37:

CGCCACCATG TTAGCTTGAG CAACATTGCT GCGGGTGGCA CTGCTGCAG AGGAAAGAAC 59

TGAGGAAGC 68

(2) INFORMATION FOR SEQ ID NO:38:

(i) SEQUENCE CHARACTERISTICS:
    (A) LENGTH: 104 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:38:

CGCCTTTCAC TGGCCTTAAG TCAGCTGCCT CATTCCCTGT TTCAAGGAAG CAAAACCTTG 60

ACATCACTTC CATTGCCAGC AACGGCGGAA GAGTGCAATG CATG 104

(2) INFORMATION FOR SEQ ID NO:39:

(i) SEQUENCE CHARACTERISTICS:
    (A) LENGTH: 97 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:39:

CATTGCACTC TCCGCCGTT GCTGGCAATG GAAGTGATGT CAAGGTTTTG CTTCCTTGAA 59

ACAGGGAATG AGGCAGCTGA CTTAAGGCCA GTGAAAGG 97

(2) INFORMATION FOR SEQ ID NO:40:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:40:

CCTGCAGGCA TCCAACCATG GCGTAATCAT GGTCAT 36

(2) INFORMATION FOR SEQ ID NO:41:

(i) SEQUENCE CHARACTERISTICS:
    (A) LENGTH: 46 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:41:

GATCTAAAAT GAGCCAACCG CCGCTGCTTG ACCACGCCAC GCAGAC 46

(2) INFORMATION FOR SEQ ID NO:42:

(i) SEQUENCE CHARACTERISTICS:
    (A) LENGTH: 46 base pairs
    (B) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:42:

CATGGTCTGC GTGGCGTGGT CAAGCAGCGG CGGTTGGCTC ATTTTA    46

( 2 ) INFORMATION FOR SEQ ID NO:43:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

ACAACAAAAT ATAAAAACAA TGTCTTTA    28

( 2 ) INFORMATION FOR SEQ ID NO:44:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

ACAACAAGAT CTAAAAACAA TGTCTTTA    28

( 2 ) INFORMATION FOR SEQ ID NO:45:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

AATTCCCGGG CCATGGC    17

( 2 ) INFORMATION FOR SEQ ID NO:46:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

AATTGCCATG GCCCGGG    17

( 2 ) INFORMATION FOR SEQ ID NO:47:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

TCGCATGCGC CAACGCCGCT GCTTGACCAC GC    32

( 2 ) INFORMATION FOR SEQ ID NO:48:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

CTGTCGACGG CTACTGAGCG GCTCTACGTC    30

( 2 ) INFORMATION FOR SEQ ID NO:49:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

GACGTAGAGC CGCTTCAGGT AGCCCCGGCG    30

( 2 ) INFORMATION FOR SEQ ID NO:50:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

CACGTAGAGC CGCTCAGTAG CCGTCGACAG    30

( 2 ) INFORMATION FOR SEQ ID NO:51:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

AAACCATGGA AAAAACCGTT GTGATTGGC    29

( 2 ) INFORMATION FOR SEQ ID NO:52:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

GGCCATGGTC TGCGTGGCGT G    21

( 2 ) INFORMATION FOR SEQ ID NO:53:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:53:

TAAAGGATGA AAAAAACCGT TGTGATTGGC  30

( 2 ) INFORMATION FOR SEQ ID NO:54:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:54:

Met Lys Lys Thr Val Val Ile Gly
  1       5

( 2 ) INFORMATION FOR SEQ ID NO:55:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:55:

TAAACCATGG AAAAAACCGT TGTGATTGGC  30

( 2 ) INFORMATION FOR SEQ ID NO:56:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:56:

Met Glu Lys Thr Val Val Ile Gly
  1       5

( 2 ) INFORMATION FOR SEQ ID NO:57:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:57:

GAGATAAAGG ATGAAAAAAA CCGTTGTGAT  30

( 2 ) INFORMATION FOR SEQ ID NO:58:

( i ) SEQUENCE CHARACTERISTICS:
    ( A ) LENGTH: 30 base pairs
    ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:58:

GAGGTCGACG ATGAAAAAAA CCGTTGTGAT    30

(2) INFORMATION FOR SEQ ID NO:59:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:59:

ATGGTCGACG TGGCGTGGTC AAGCAGCGG    29

(2) INFORMATION FOR SEQ ID NO:60:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:60:

GAGATAAAGG ATGAAAAAAA CCGTTGTGAT    30

(2) INFORMATION FOR SEQ ID NO:61:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:61:

Met Lys Lys Thr Val Val
1               5

(2) INFORMATION FOR SEQ ID NO:62:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:62:

CCATGGAAAA AACCGTTGTG AT    22

(2) INFORMATION FOR SEQ ID NO:63:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:63:

```
    Met  Glu  Lys  Thr  Val  Val
    1                   5
```

( 2 ) INFORMATION FOR SEQ ID NO:64:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

GAGGTCGACG ATGAAAAAAA CCGTTGTGAT   30

( 2 ) INFORMATION FOR SEQ ID NO:65:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:65:

```
    Met  Lys  Lys  Thr  Val  Val
    1                   5
```

( 2 ) INFORMATION FOR SEQ ID NO:66:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:66:

CCGCTGCTTG ACCACGCCAC GCAGACCATG G   31

( 2 ) INFORMATION FOR SEQ ID NO:67:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:67:

CCGCTGCTTG ACCACGCCAC GTCGACCATG G   31

( 2 ) INFORMATION FOR SEQ ID NO:68:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:68:

GACGAGATAA AGCATGCAAA AAACCGTTGT   30

( 2 ) INFORMATION FOR SEQ ID NO:69:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:69:

Met  Gln  Lys  Thr  Val
    1                        5

( 2 ) INFORMATION FOR SEQ ID NO:70:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:70:

GACGAGATAA AGGATGAAAA AAACCGTTGT    30

( 2 ) INFORMATION FOR SEQ ID NO:71:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:71:

Met  Lys  Lys  Thr  Val
    1                        5

( 2 ) INFORMATION FOR SEQ ID NO:72:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:72:

GACGAGATAA AGCATGCAAA AAACCGTTGT    30

( 2 ) INFORMATION FOR SEQ ID NO:73:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:73:

Met  Gln  Lys  Thr  Val
    1                        5

( 2 ) INFORMATION FOR SEQ ID NO:74:

( i ) SEQUENCE CHARACTERISTICS:
        ( A ) LENGTH: 35 base pairs
        ( B ) TYPE: nucleic acid (C) STRANDEDNESS: single
(D) TOPOLOGY: linear (i i) MOLECULE TYPE: DNA (genomic)

(x i) SEQUENCE DESCRIPTION: SEQ ID NO:74:

AGAGCGTATC GTGAGGGATC TGATTTTAGT CGGCG    35

(2) INFORMATION FOR SEQ ID NO:75:

(i) SEQUENCE CHARACTERISTICS:
(A) LENGTH: 35 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:75:

GCGCGGATCC ATGGGGGATC TGATTTTAGT CGGCG    35

(2) INFORMATION FOR SEQ ID NO:76:

(i) SEQUENCE CHARACTERISTICS:
(A) LENGTH: 10 amino acids
(B) TYPE: amino acid
(D) TOPOLOGY: linear (i i) MOLECULE TYPE: protein (x i) SEQUENCE DESCRIPTION: SEQ ID NO:76:

Met Arg Asp Leu Ile Leu Val Gly Gly Gly
1               5                   10

(2) INFORMATION FOR SEQ ID NO:77:

(i) SEQUENCE CHARACTERISTICS:
(A) LENGTH: 10 amino acids
(B) TYPE: amino acid
(D) TOPOLOGY: linear (i i) MOLECULE TYPE: protein (x i) SEQUENCE DESCRIPTION: SEQ ID NO:77:

Met Gly Asp Leu Ile Leu Val Gly Gly Gly
1               5                   10

(2) INFORMATION FOR SEQ ID NO:78:

(i) SEQUENCE CHARACTERISTICS:
(A) LENGTH: 32 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:78:

GCGGCGCATG CGGGATCTGA TTTTAGTCGG CG    32

(2) INFORMATION FOR SEQ ID NO:79:

(i) SEQUENCE CHARACTERISTICS:
(A) LENGTH: 30 base pairs
(B) TYPE: nucleic acid
(C) STRANDEDNESS: single
(D) TOPOLOGY: linear (i i) MOLECULE TYPE: DNA (genomic)

( x i ) SEQUENCE DESCRIPTION: SEQ ID NO:79:

CATCGGATCC TGTCAGGAAA ATGGTTCAGC    30

BETA-CAROTENE BIOSYNTHESIS IN GENETICALLY ENGINEERED HOSTS

CROSS-REFERENCE TO RELATED APPLICATION

This is a division of application Ser. No. 08/095,726 filed Jul. 21, 1993 that is now U.S. Pat. No. 5,530,188, which was a continuation-in-part of application Ser. No. 07/662,921, filed Feb. 28, 1991, now abandoned, and whose continuation application Ser. No. 096,043 filed Jul. 22, 1993 is now U.S. Pat. No. 5,530,189. Application Ser. No. 07/785,569 filed Oct. 30, 1991, now abandoned, whose continuation Ser. No. 093,577 filed Jul. 19, 1993, now U.S. Pat. No. 5,545,816, was also a continuation-in-part of Ser. No. 07/662,921, which was a continuation-in-part of application Ser. No. 07/562,674, filed Aug. 3, 1990, now abandoned, which was a continuation-in-part of application Ser. No. 07/525,551, filed May 18, 1990, now abandoned, which was a continuation-in-part of application Ser. No. 07/487,613 filed Mar. 2, 1990, now abandoned, and whose disclosures are incorporated by reference.

DESCRIPTION

1. Technical Field

The present invention relates to carotenoid biosynthesis. More specifically, this invention relates to the isolation, characterization and expression of the *Erwinia herbicola* gene encoding the enzyme lycopene cyclase that catalyzes the formation of the carotenoid, beta-carotene. The invention also relates to methods for expression of this *Erwinia herbicola* enzyme gene in prokaryote hosts such as *Escherichia coli* (*E. coli*) and *Agrobacterium tumefaciens* (*A. tumefaciens*), in eukaryote hosts such as yeasts like *Saccharomyces cerevisiae* (*S. cerevisiae*) and higher plants such as alfalfa and tobacco, as well as to methods for preparation of the carotenoid, beta-carotene.

2. Background Art

Carotenoids are 40-carbon ($C_{40}$) terpenoids consisting generally of eight isoprene ($C_5$) units joined together. Linking of the units is reversed at the center of the molecule. Trivial names and abbreviations will be used throughout this disclosure, with IUPAC-recommended semisystematic names given in parentheses after first mention of each name.

Carotenoids are pigments with a variety of applications.

Phytoene (7,8,11,12,7',8',11',12'-ω octahydro-ω,ω-carotene) is the first carotenoid in the carotenoid biosynthesis pathway and is produced by the dimerization of a 20-carbon atom precursor, geranylgeranyl pyrophosphate (GGPP). Phytoene has useful applications in treating skin disorders (U.S. Pat. No. 4,642,318) and is itself a precursor for colored carotenoids. Aside from certain mutant organisms, such as *Phycomyces blakesleeanus carB*, no current methods are available for producing phytoene via any biological process.

In some organisms, the red carotenoid lycopene (ω,ω-carotene) is the next carotenoid produced in the phytoene in the pathway. Lycopene imparts the characteristic red color to ripe tomatoes.

Lycopene has utility as a food colorant. It is also an intermediate in the biosynthesis of other carotenoids in some bacteria, fungi and green plants.

Lycopene is prepared biosynthetically from phytoene through four sequential dehydrogenation reactions by the removal of eight atoms of hydrogen. The enzymes that remove hydrogen from phytoene are phytoene dehydrogenases. One or more phytoene dehydrogenases can be used to convert phytoene to lycopene and dehydrogenated derivatives of phytoene intermediate to lycopene are also known. For example, some strains of *Rhodobacter sphaeroides* contain a phytoene dehydrogenase that removes six atoms of hydrogen from phytoene to produce neurosporene.

Of interest herein is a single dehydrogenase that converts phytoene into lycopene. That enzyme removes four moles of hydrogen from each mole of phytoene, and is therefore referred to hereinafter as phytoene dehydrogenase-4H. The *Rhodobacter* phytoene dehydrogenase that removes three moles of hydrogen from each mole of phytoene will be hereinafter referred to as phytoene dehydrogenase-3H so that the distinctions between the two enzymes discussed herein can be readily maintained.

Lycopene is an intermediate in the biosynthesis of carotenoids in some bacteria, fungi, and all green plants. Carotenoid-specific genes that can be used for synthesis of lycopene from the ubiquitous precursor farnesyl pyrophosphate include those for the enzymes GGPP synthase, phytoene synthase, and phytoene dehydrogenase-4H.

Beta-carotene is the third carotenoid produced in the *Erwinia* carotenoid biosynthesis pathway. It is also synthesized by a number of bacteria, fungi, and most green plants.

Beta-carotene has utility as a colorant for margarine and butter, as a source for vitamin A production, and has recently been implicated as having preventative effects against certain kinds of cancers.

For example, prospective and retrospective epidemiologic studies have consistently shown that low levels of serum or plasma beta-carotene are associated with the subsequent development of lung cancer. Because retinol is not similarly related to lung cancer risk, beta-carotene appears to have a protective effect without its conversion to vitamin A. Ziegler, *Amer. Instit. Nutr.*, publication 022/3166/89, 116 (1989).

Beta-carotene is produced by the cyclization of unsaturated carotenoids in a procedure not yet well understood. Bramley et al, In *Current Topics in Cellular Regulation* 29:291,297 (1988). Because only mutants that accumulate lycopene but not gamma-carotene (another potential precursor) have been found, it is believed that in both plants and microorganisms a single cyclase is responsible for conversion of lycopene to beta-carotene. Generally, the enzymes involved in this cyclization have been found as integral membrane proteins.

Current methods for commercial production of beta-carotene include isolation from carrots, chemical synthesis [Isler. et al., U.S. Pat. No. 2,917,539 (1959)] and microbial production by *Choanephora trispora* [Zajic, U.S. Pat. No. 2,959,521 (1960) and 3,128,236 (1964)].

Carotenoids are synthesized in a variety of bacteria, fungi, algae, and higher plants. At the present time only a few plants are widely used for commercial carotenoid production. However, the productivity of carotenoid synthesis in these plants is relatively low and the resulting carotenoids are expensively produced.

One way to increase the productive capacity of biosynthesis would be to apply recombinant DNA technology. Thus, it would be desireable to produce carotenoids generally and beta-carotene specifically by recombinant DNA technology. This would permit control over quality, quantity and selection of the most suitable and efficient producer organisms. The latter is especially important for commercial production economics and therefore availability to consumers. For example, yeast, such as *S. cerevisiae* in large fermentors and higher plants, such as alfalfa or tobacco, can be mobilized for carotenoid production as described hereinafter.

An organism capable of carotenoid synthesis and a potential source of genes for such an endeavor is *Erwinia herbicola*, which is believed to carry putative genes for carotenoid production on a plasmid (Thiry, *J. Gen. Microbiol.*, 130:1623 (1984)) or chromosomally (Perry et al., *J. Bacteriol*, 168:607 (1986)). *Erwinia herbicola* is a genus of Gram-negative bacteria of the ENTEROBACTERIACEAE family, which are facultative anaerobes. Indeed, recently published European patent application 0 393 690 A1 (published Apr. 20, 1990; sometimes referred to herein as "EP 0 393 690") reports use of DNA from another *Erwinia* species, *Erwinia uredovoa* 20D3 (ATCC 19321) for preparing carotenoid molecules.

As is discussed in detail hereinafter, the present invention utilizes DNA from *Erwinia herbicola* EHO-10 (ATCC 39368) for preparation of carotenoid molecules and the enzymes used in their synthesis. *Erwinia herbicola* EHO-10 used herein is also referred to as *Escherichia vulneris*.

The genus is commonly divided into three groups. Of the three, the Herbicola group includes species (e.g. *Erwinia herbicola*) which typically form yellow pigments that have now been found to be carotenoids.

These bacteria exist as saprotrophs on plant surfaces and as secondary organisms in lesions caused by many plant pathogens. They can also be found in soil, water and as opportunistic pathogens in animals, including man.

A precise organismic function has yet to be ascribed to the pigment(s) produced by *Erwinia herbicola*. Perry et al., 168:607 (1986), showed that the genes coding for the production of an unknown yellow pigment lie within an approximately 13-kilobase (kb) sequence coding for at least seven polypeptides, and that the expression of the yellow pigment is cyclic AMP mediated. Tuveson, *J. Bacteriol.*, 170:4675 (1988), demonstrated that these genes, cloned from *Erwinia herbicola* and expressed in an *E. coli* strain, offered the host some protection against inactivation by near-UV light and specific phototoxic molecules.

*E. coli* and *S. cerevisiae* are commonly used for expressing foreign genes, but to optimize yields and minimize technical maintenance procedures, it would be preferable to utilize a higher plant species.

BRIEF SUMMARY OF THE INVENTION

Because of the utility of beta-carotene as an effective and apparently harmless food colorant, the ability to produce natural beta-carotene in commercially advantageous amounts from transgenic biological sources with the aid of recombinant DNA technology is a major benefit flowing from this invention. In addition, beta-carotene is in the pathway for biological synthesis of further $C_{40}$ carotenoids such as zeaxanthin and zeaxanthin diglucoside so that beta-carotene and a gene that encodes an enzyme for preparing beta-carotene are useful for the synthesis of such other carotenoids. To realize these benefits, several aspects and embodiments are contemplated by this invention.

One aspect contemplated by this invention is an isolated DNA segment comprising a nucleotide sequence of at least about 1125 base pairs, including a sequence defining a structural gene capable of expressing the *Erwinia herbicola* enzyme lycopene cyclase, a DNA variant or analog thereof. This lycopene cyclase enzyme has a molecular mass of about 39,000 daltons, and converts lycopene to β-carotene.

A typical, useful DNA segment contains at least about 1125 base pairs and preferably at least about 1150 base pairs and lies within the approximately 1548 bp Sal I (9340) to Pst I (7792) DNA fragment from pARC376 illustrated in FIG. 5. The native *Erwinia herbicola* structural gene for lycopene cyclase contains about 1125 base pairs and is located between positions 9002 and 7878 of pARC376. Larger DNA segments are also contemplated, as discussed hereinafter.

A preferred DNA segment includes a nucleotide base sequence shown in FIG. 19, panels 1-3, from about base 19 to about base 1234. A more preferred sequence of about 1140 bp is present in the approximately 1142 bp Sph I-Bam HI restriction fragment of the plasmid pARC1509, shown in FIG. 19.

A still further particularly preferred DNA segment is an approximately 1319 bp Nco I-Bam HI fragment. This fragment contains an approximately 177 bp portion that encodes a chloroplast transit peptide operatively linked in frame to the 5' end of the above Sph I-Bam HI 1142 bp lycopene cyclase gene. This DNA segment can be used for expression of lycopene cyclase in higher plants and transport of the expressed lycopene cyclase into chloroplasts such as those of tobacco.

Another aspect of this invention is a recombinant DNA molecule comprising a vector operatively linked to an exogenous DNA segment isolated from *Erwinia herbicola*. This exogenous DNA segment defines a structural gene capable of expressing the *Erwinia herbicola* enzyme lycopene cyclase, a DNA variant or analog thereof. Also included is a promoter suitable for driving the expression of the enzyme in a compatible host organism. Exemplary, particularly preferred vectors are plasmids pARC1509, pARC1510 and pARC1520.

A further aspect of this invention is a method for preparing the enzyme lycopene cyclase, or enzyme having substantially the same biological activity that is encoded by a DNA variant or analog thereof. This method comprises initiating a culture, in a nutrient medium, of prokaryotic or eukaryotic host cells transformed with a recombinant DNA molecule containing an expression vector compatible with the cells. This vector is operatively linked to an isolated exogenous *Erwinia herbicola* DNA segment defining the structural gene for lycopene cyclase as discussed before. The culture is maintained for a time period sufficient for the cells to express the lycopene cyclase protein molecule.

Still another aspect contemplated by this invention is a method for producing beta-carotene that comprises initiating a culture in a nutrient medium of prokaryotic or eukaryotic host cells that provides lycopene, those prokaryotic or eukaryotic host cells being transformed with one or more recombinant DNA molecule(s) described herein that include a structural gene that can express lycopene cyclase, its DNA analog or variant. The culture is maintained for a time period sufficient for the host cells to express lycopene cyclase and for the expressed lycopene cyclase to convert the provided lycopene into beta-carotene. The beta-carotene is then recovered. Preferably, these recombinant DNA molecules contain an expression vector compatible with the host cells operatively linked to an exogenous *Erwinia herbicola* DNA segment comprising (i) a nucleotide base sequence corresponding to a sequence defining a structural gene for geranylgeranyl pyrophosphate synthase, its DNA variants and analogs, (ii) a nucleotide base sequence corresponding to a sequence defining a structural gene for phytoene synthase, its DNA variant or analog thereof, (iii) a nucleotide base sequence corresponding to a sequence defining a structural gene for phytoene dehydrogenase-4H, its DNA variants and analogs, and (iv) a nucleotide base sequence corresponding to a sequence defining a structural gene for lycopene cyclase as previously described. The culture is maintained for a time period sufficient for the cells to express the products of the structural genes (i), (ii), (iii) and (iv) and form beta-carotene.

In particulary preferred practice, all of the recombinant DNA utilized in this invention is from Erwinia herbicola. Another preferred embodiment of this invention is a recombinant DNA molecule as described above, wherein the promoter is Rec 7 for E. coli, PGK, GAL 10 and GAL 1 for yeasts such as S. cerevisiae and CaMV 35S for higher plants.

Other preferred embodiments contemplate the methods of preparation described above, wherein the host transformed is either a prokaryote, such as E. coli, a eukaryote, for example yeast such as S. cerevisiae, or a higher plant, such as alfalfa or tobacco.

Also contemplated is a method for increasing the production of total carotenoids in higher plants. Here, a higher plant is transformed with a recombinant molecule that encodes a structural gene for the Erwinia herbicola enzyme lycopene cyclase, a DNA variant or analog thereof that encodes an enzyme exhibiting substantially the same biological activity. The transformed plant is maintained (e.g., grown) for a time period sufficient for the amount of lycopene cyclase to be increased above the amount present in a native (normal), non-transformed plant of the same type. The increase in lycopene cyclase production leads to an increase in total carotenoids in the transformed plant.

Preferably, an about 177 bp sequence that encodes a chloroplast transit peptide of the tobacco ribulose hisphosphate carboxylase-oxygenase gene is operatively linked in frame to the 5' end of the lycopene cyclase structural gene. This construct leads to increased production of total carotenoids in the chloroplast of the transformed plant as compared to a native, non-transformed plant of the Same type.

Still further embodiments and advantages of the invention will become apparent to those skilled in the art upon reading the entire disclosure contained herein.

BRIEF DESCRIPTION OF DRAWINGS

FIG. 2 in three sheets as FIG. 2-1, FIG. 2—2, and FIG. 2—3 illustrates the nucleotide base sequences of certain preferred DNA segments of the structural gene for geranylgeranyl pyrophosphate (GGPP) synthase (SEQ ID NO:1). The base sequences are shown conventionally from left to right and in the direction of 5' terminus to 3' terminus, using the single letter nucleotide base code.

The reading frame of the 5' end of the structural gene illustrated herein is indicated by placement of the deduced, amino acid residue sequence (SEQ ID NO:2) of the protein for which it codes below the nucleotide sequence, such that the triple letter code for each amino acid residue is located directly below the three-base codon for each amino acid residue. Numerals to the right of the DNA sequence indicate nucleotide base positions within the DNA sequence shown. All of the structural genes shown in the figures herein are similarly illustrated, with amino acid initiation position beginning here with the initial methionine residue (Met) at DNA position about 124 as shown.

Several restriction enzyme sites of importance are indicated above the DNA sequence. These represent points of manipulation in engineering the gene construct encoding the enzyme.

Figure 1:
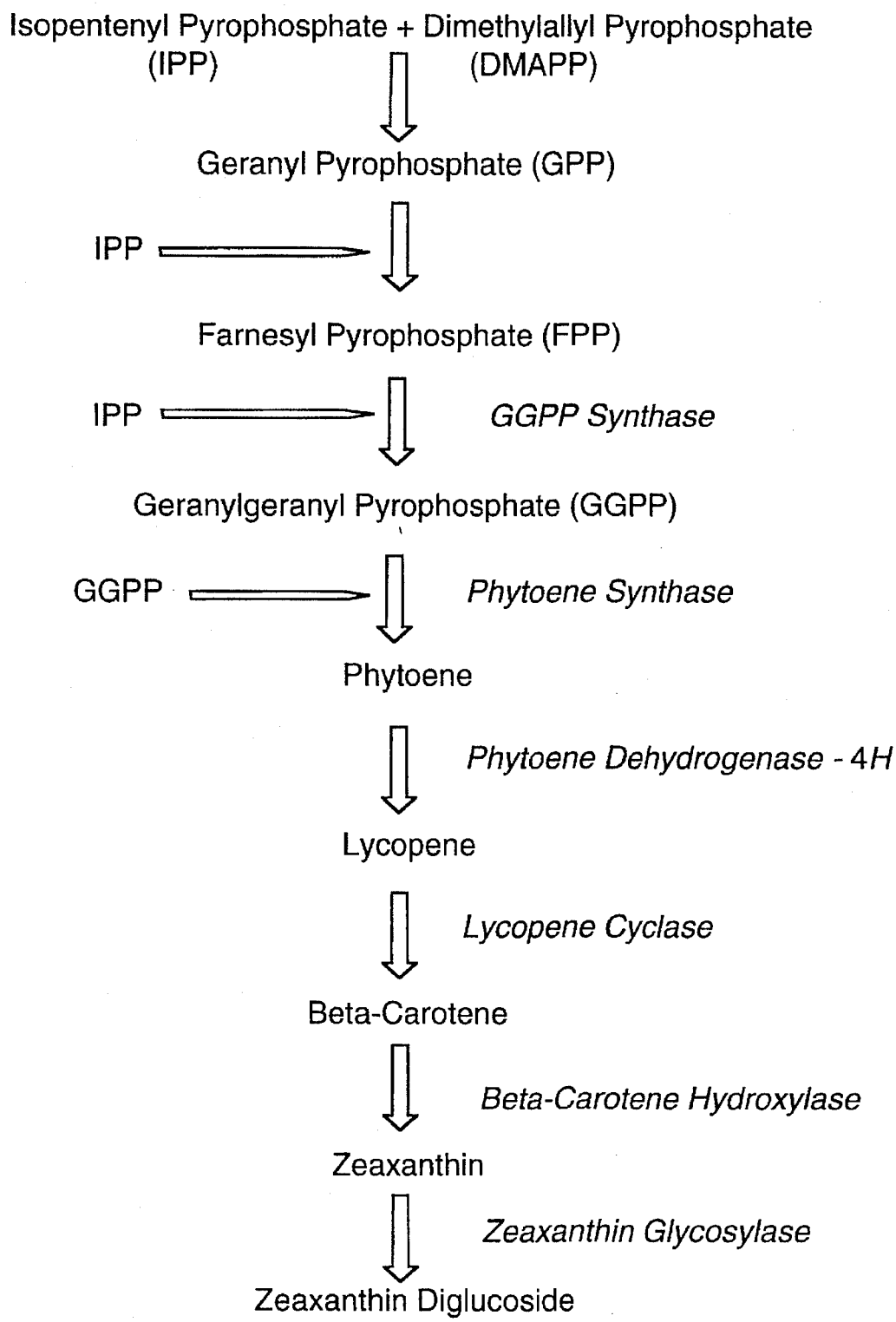
FIG. 1 is a flow diagram of the carotenoid synthesis scheme utilizing the Erwinia gene complement located in the plasmid pARC376.

FIG. 3 shown in three sheets as FIG. 3-1, FIG. 3-2 and FIG. 3-3 illustrates the DNA (SEQ ID NO: 3) and deduced amino acid residue (SEQ ID NO: 4) sequences of more preferred, heterologous structural genes of Erwinia herbicola GGPP synthase. Here, the expressed protein begins with the Met residue at about position 150 as shown and terminates within the Eco RV site (about 1153) in the DNA construct present in plasmid pARC489B, whereas the gene terminates at the Bal I site (about 1002) in the DNA construct present in plasmid pARC489D. The short aminoterminal sequence MetAlaGluPhe (about 150–161) is a heterologous sequence from plasmid pARC306A, and is substituted for the native sequence from DNA position 124 to 150 shown in FIG. 2.

FIG. 4 shown in three sheets as FIG. 4-1, FIG. 4-2 and FIG. 4-3 illustrates the nucleotide (SEQ ID NO: 5) and amino acid (SEQ ID NO: 6) sequences of the structural gene for phytoene synthase.

Figure 5:
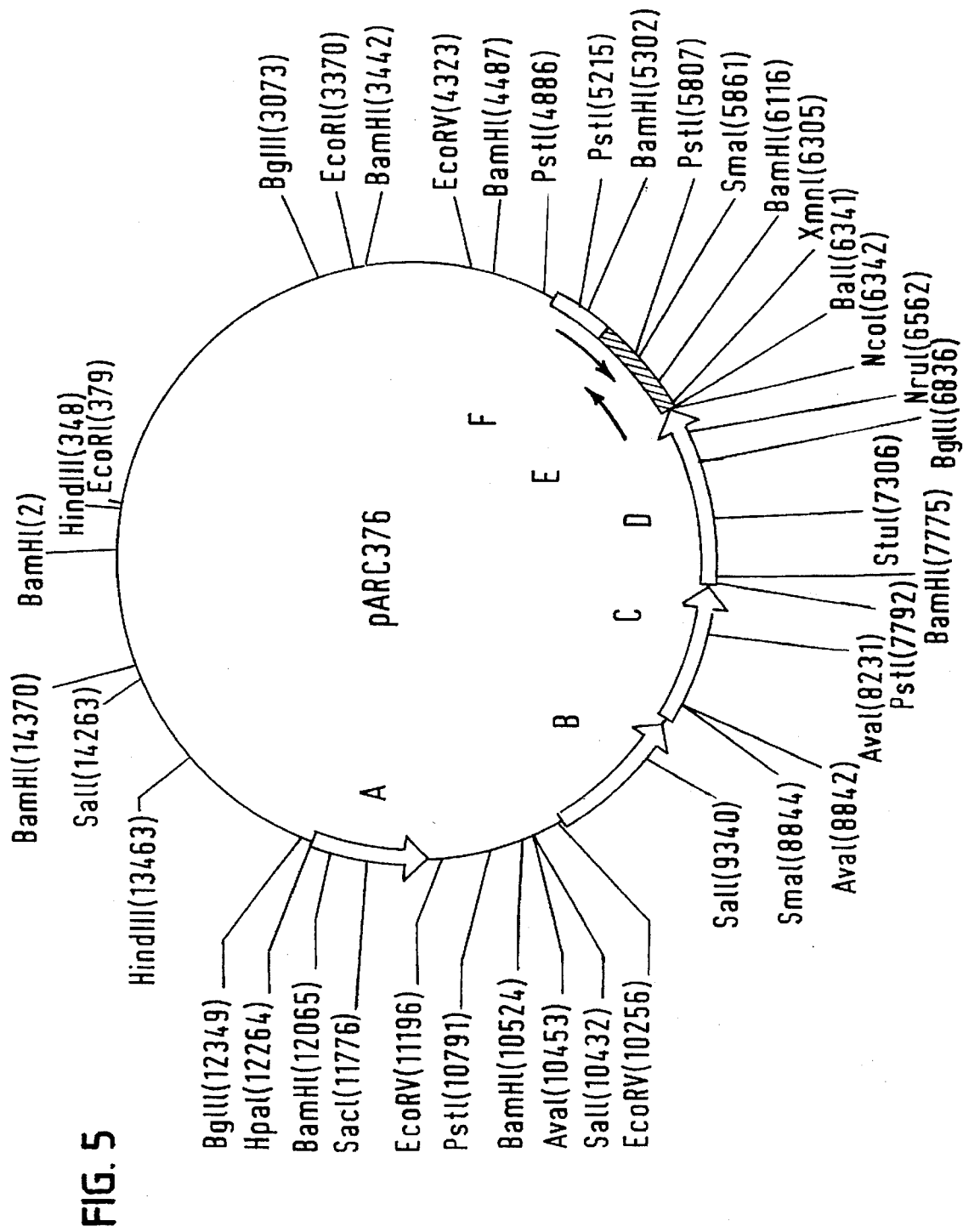

The Met initiation codon (about position 16 as shown) corresponds to about position 6383 on pARC376 in FIG. 5. The Bam HI restriction site at about 1093 in FIG. 4 corresponds to the Bam HI site at about position 5302 on pARC376 in FIG. 5. The illustrated Bgl II restriction site shown at about position 8 is not present in the native DNA sequence and was added as is discussed hereinafter.

FIG. 5 schematically shows the plasmid pARC376 containing the full complement of enzyme genes, represented by capital letters, required for the synthesis of carotenoids from farnesyl pyrophosphate, as indicated in the schematic of FIG. 1. The direction of transcription (arrows) is uniform for all enzyme structural genes except beta-carotene hydroxylase (F), which is transcribed in an opposite direction. Important restriction enzyme sites are also identified with parenthesized position numbers. The synthesis of phytoene is catalyzed by the enzymes GGPP synthase (A) and phytoene synthase (E). Genes labeled B, C, D and F encode the enzymes zeaxanthin glycosylase, lycopene cyclase, phytoene dehydrogenase-4H and beta-carotene hydroxylase, respectively. The overlap of genes E and F is shown by hatching.

Figure 6:
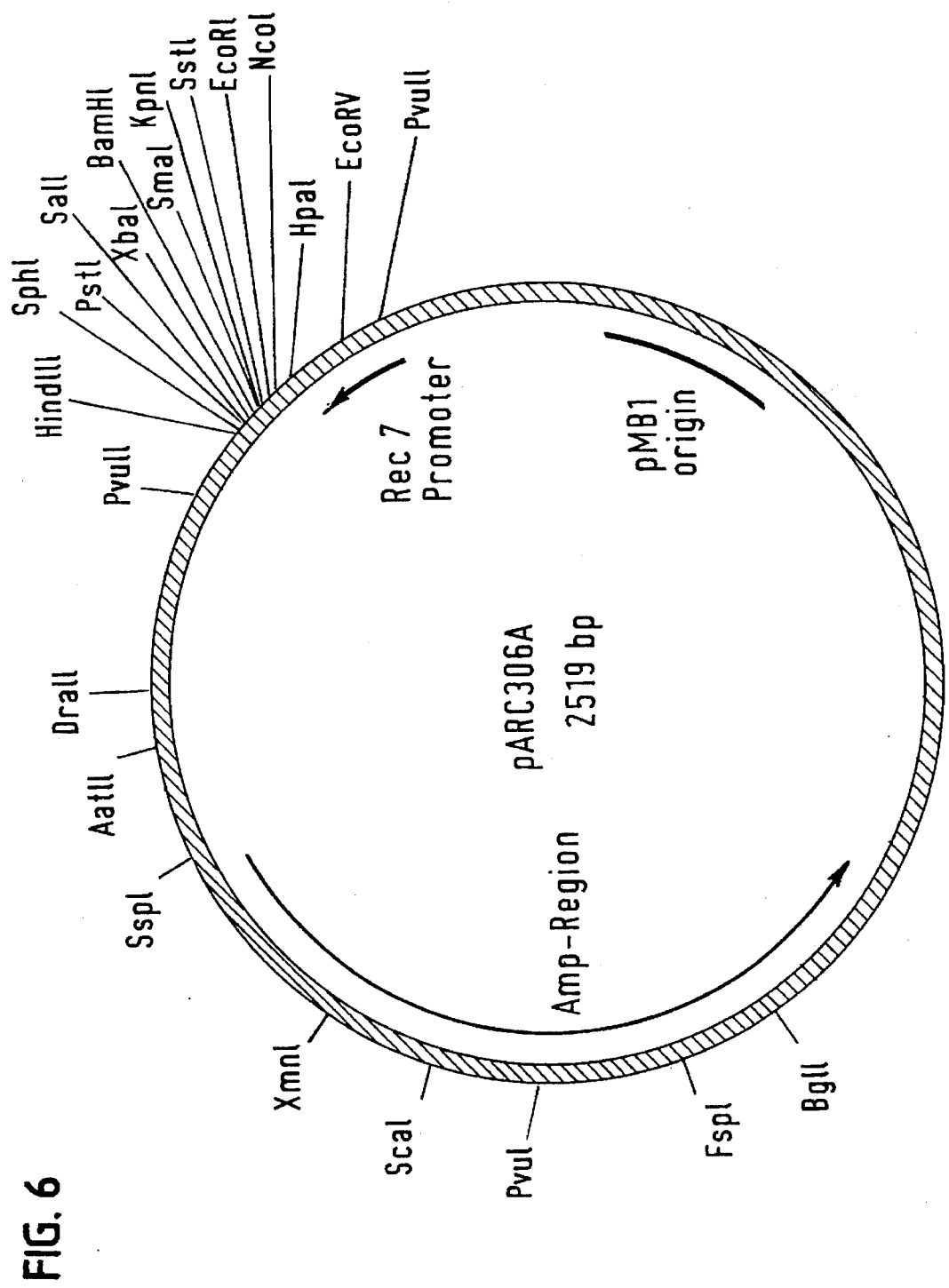

FIG. 6 is a schematic representation of the plasmid pARC306A, which contains the Rec 7 promoter. This plasmid also has multiple cloning sites adjacent to the Rec 7 promoter and 5' and 3' transcription termination loops. Approximate positions of restriction enzyme sites are shown.

Figure 7:
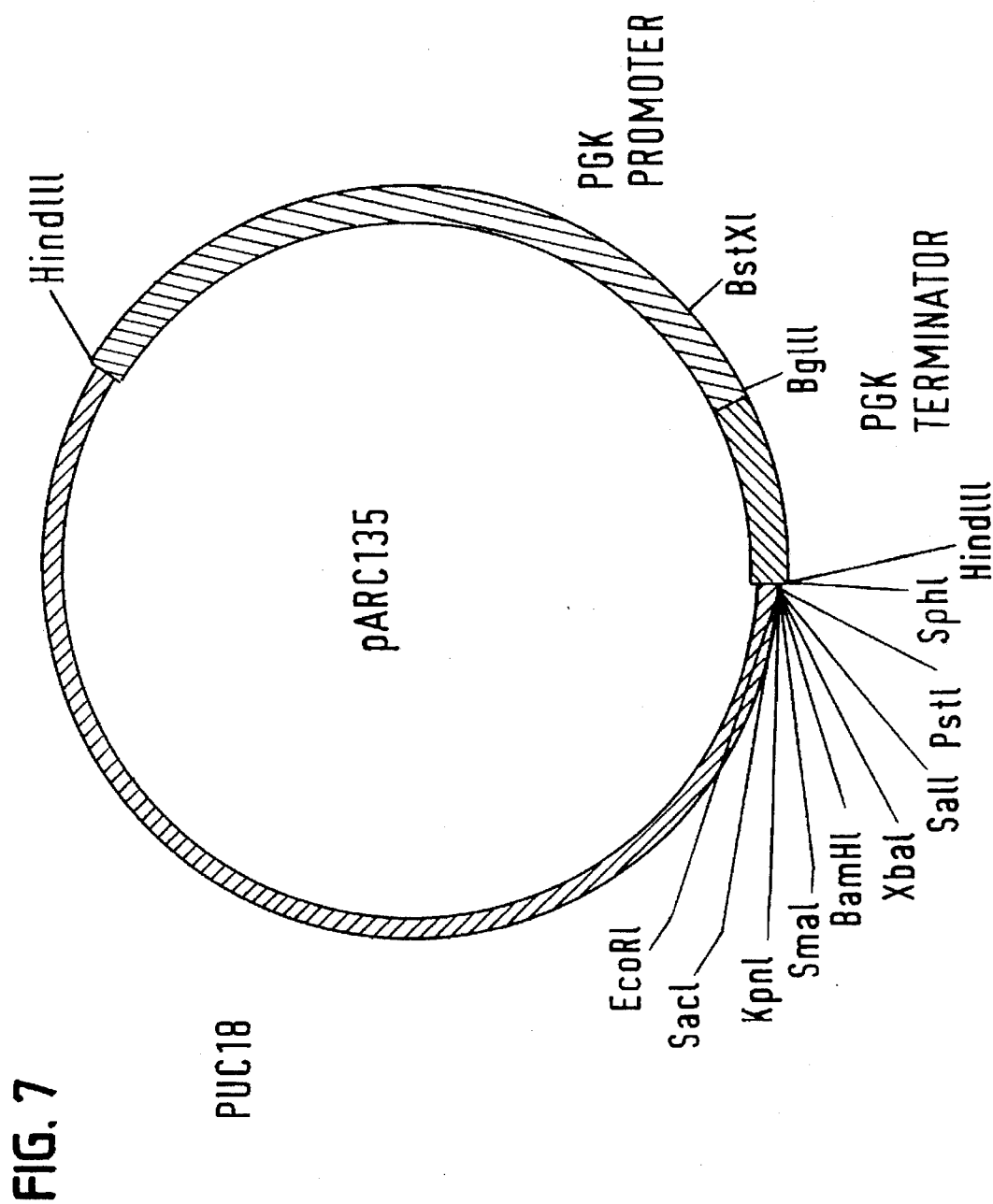

FIG. 7 illustrates schematically the plasmid pARC135, which contains the S. cerevisiae phosphoglyceric acid kinase (PGK) promoter operatively linked at the Bgl II site. Various additional features of the plasmid are also illustrated.

Figure 8:
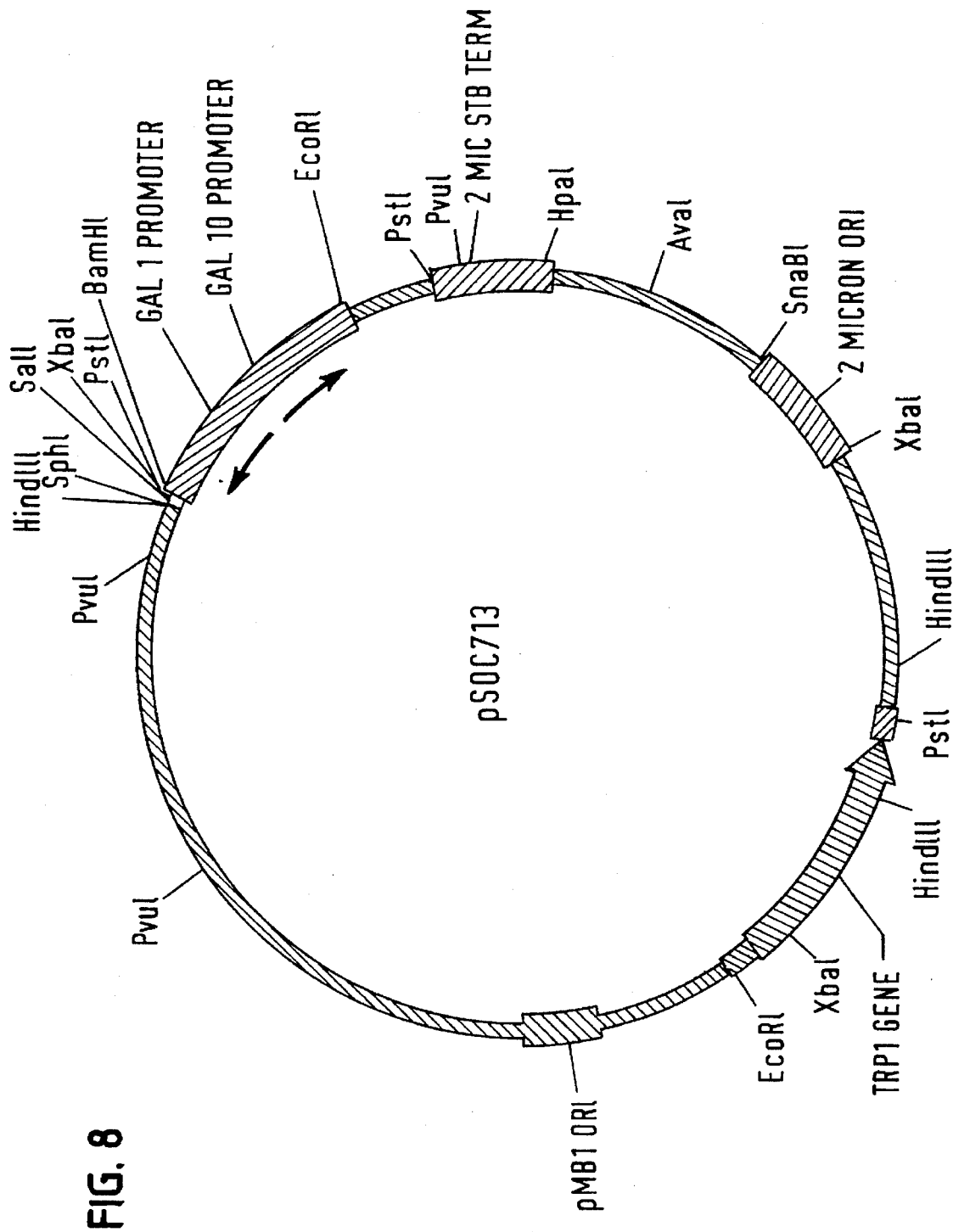

FIG. 8 shows a schematic representation of the vector pSOC713, including a partial restriction enzyme map.

Figure 9:
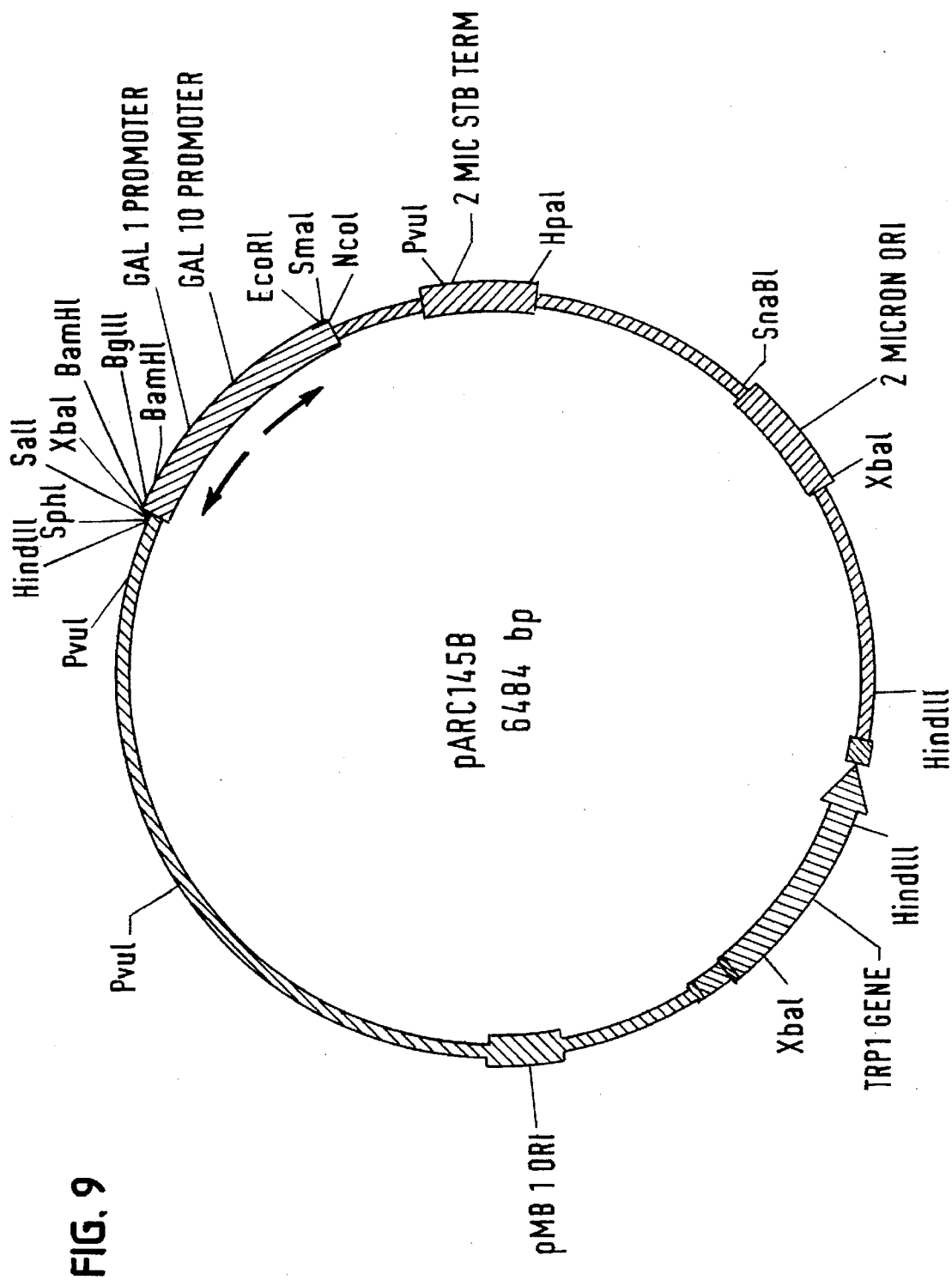

FIG. 9 is a schematic representation of plasmid pARC145B, which is a yeast/E. coli shuttle vector for expression of introduced genes in yeast, including a partial restriction enzyme map.

Figure 10:
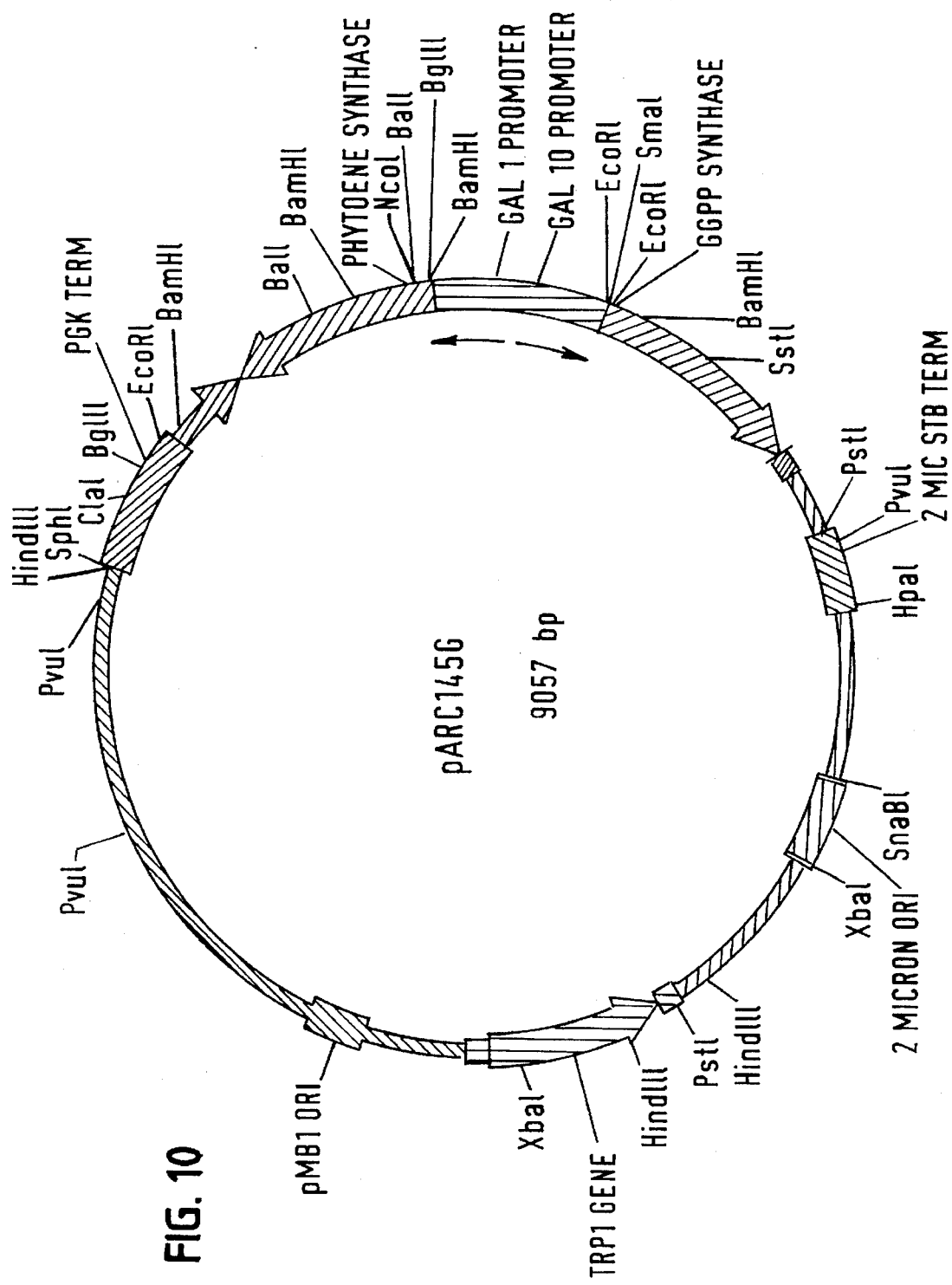

FIG. 10 is a schematic representation of the vector pARC145G, which is basically pARC145B above that contains the two preferred genes; i.e., GGPP synthase and phytoene synthase, each operatively linked at their 5' ends to the divergent promoters GAL 10 and GAL 1. Phytoene synthase also has a PGK terminator at the 3' end.

FIG. 11 shown in four panels as FIG. 11-1, FIG. 11-2, FIG. 11-3 and FIG. 11-4 illustrates the DNA (SEQ ID NO:7) and deduced amino acid residue (SEQ ID NO:8) sequences of the Erwinia herbicola structural gene for phytoene dehydrogenase-4H. The MET codon (shown at position 7) corresponds to position 7849 on plasmid pARC376 in FIG. 5.

Figure 12:
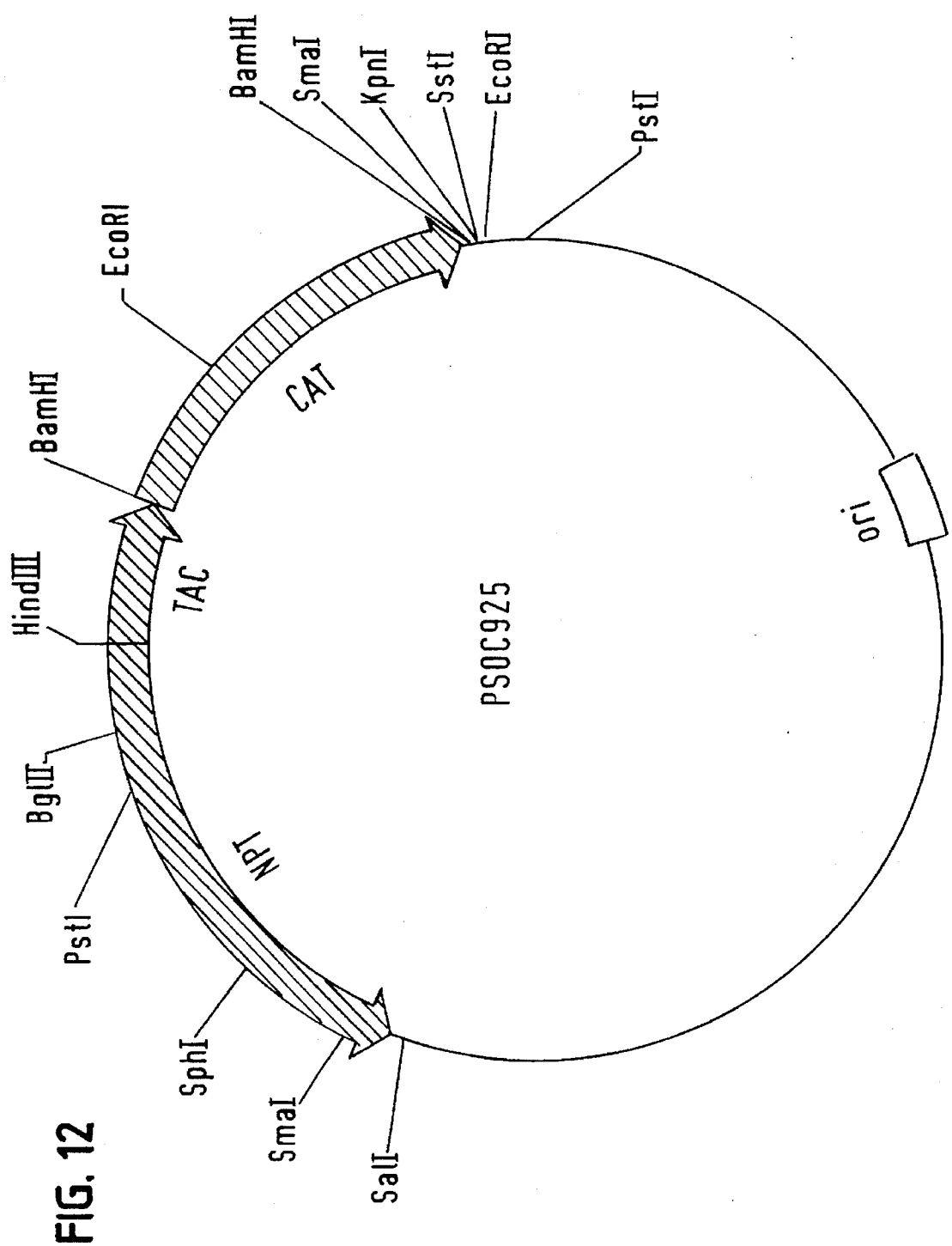

FIG. 12 is a schematic representation of the vector pSOC925, including a partial restriction enzyme map.

Figure 13:
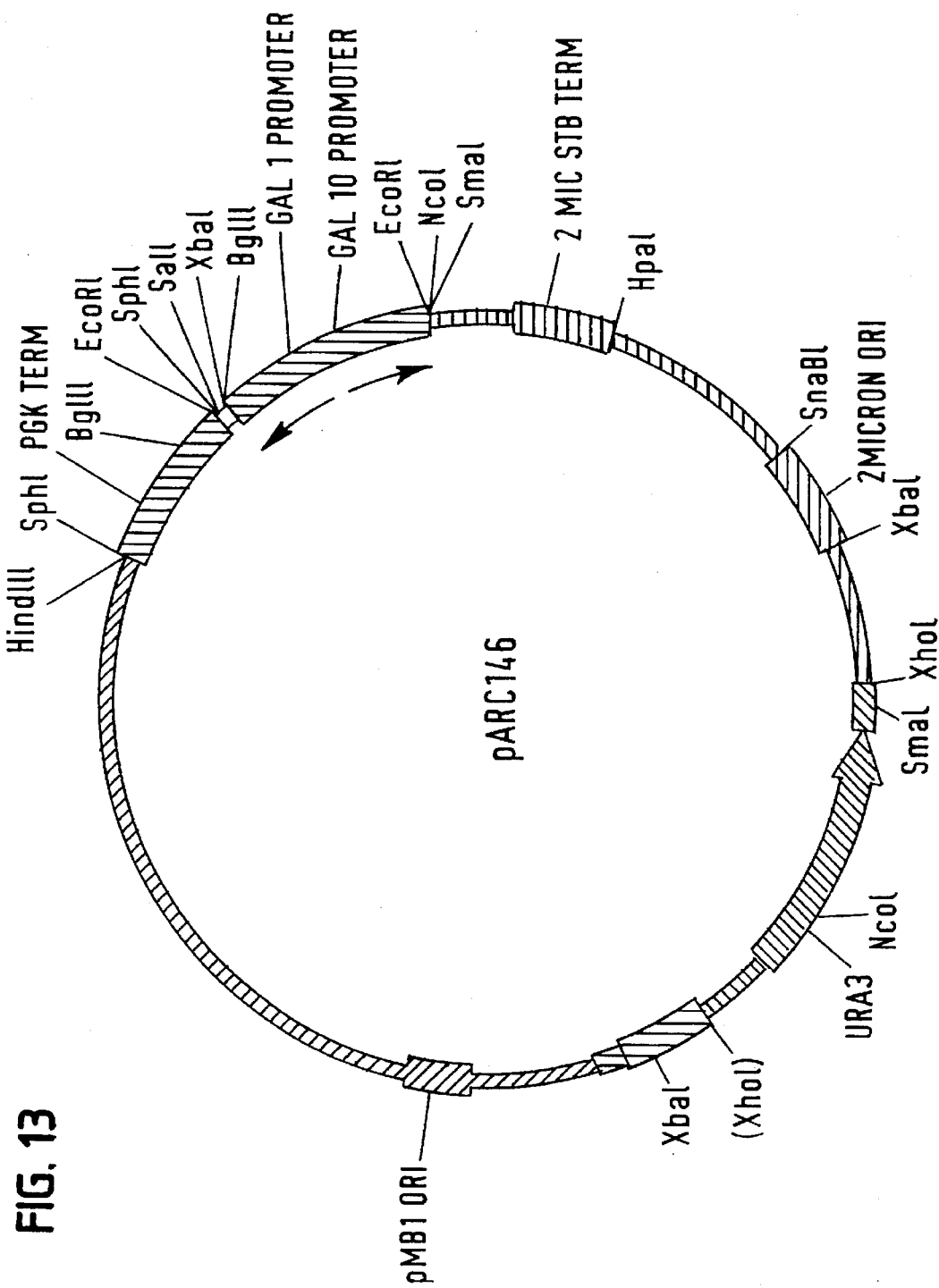

FIG. 13 is a schematic representation of plasmid pARC146, including a partial restriction enzyme map.

Figure 14:
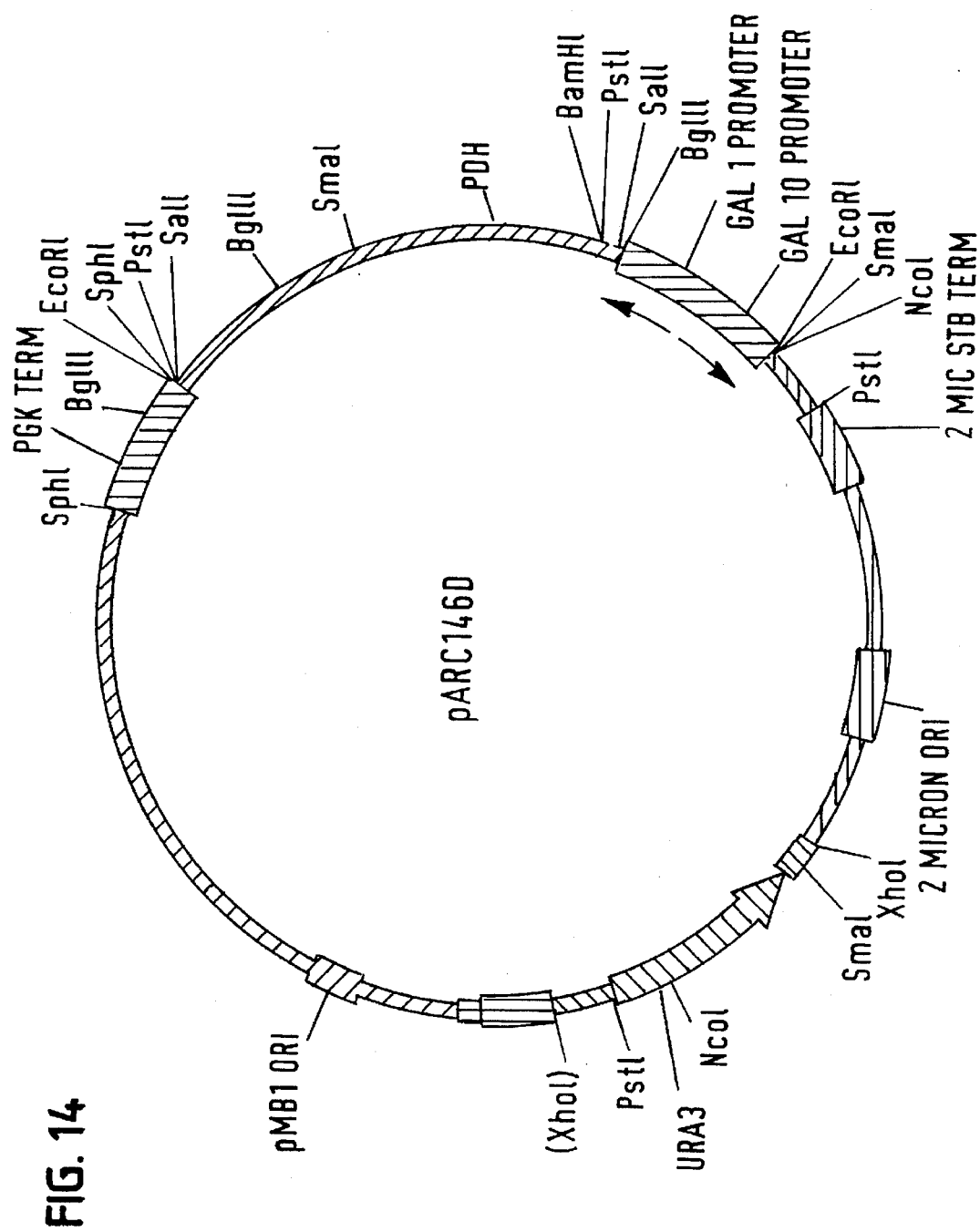

FIG. 14 shows the vector pARC146D, including a partial restriction enzyme map.

FIG. 15 shown in four panels as FIGS. 15-1, FIG. 15-2, FIG. 15-3 and FIG. 15-4 illustrates the DNA (SEQ ID NO:9) and deduced amino acid residue (SEQ ID NO:10) sequence of the Erwinia herbicola structural gene for phytoene dehydrogenase-4H present in plasmid pARC146D.

Figure 16:
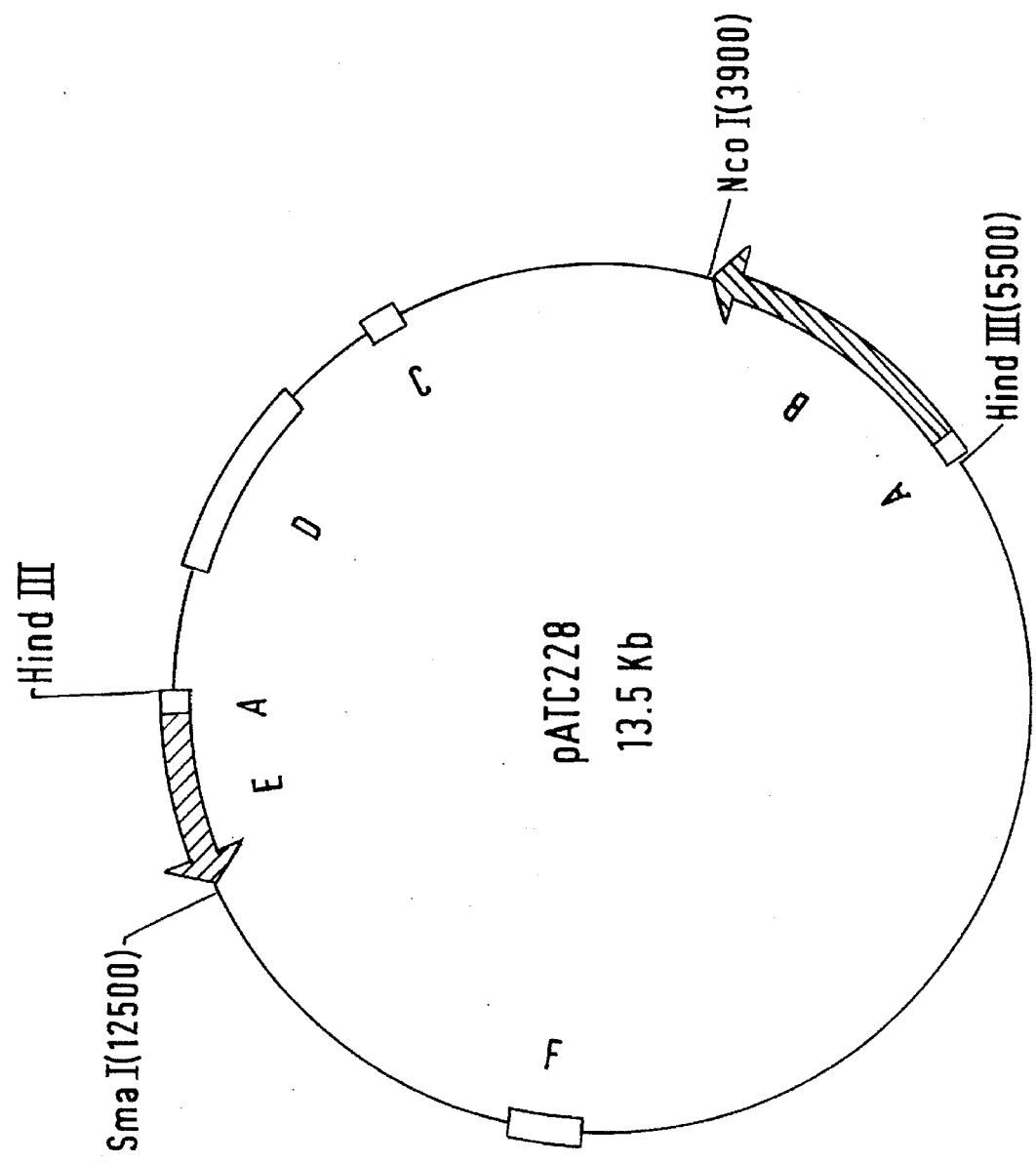

FIG. 16 is a schematic representation of plasmid pATC228, including a partial restriction enzyme map. In this figure, A–F are schematic representations of the following sequences: A=tac promoter, B=phytoene dehydrogenase-4H gene, C=pMB1 ori, D-ampicillin resistance gene, E=chloramphenicol resistance gene, and F=R1162 ori.

FIG 17 illustrates the encoded transit peptide (SEQ ID NO:11) and DNA coding sequence (SEQ ID NO:12) linked to the 5' end of the phytoene dehydrogenase-4H structural gene or other genes for transport of each expressed fused enzyme or a combination of expressed fused enzymes, into tobacco chloroplasts as well as other plant chloroplasts. Stars over nucleotide positions 69 and 72 in this sequence indicate G for T and G for A replacements utilized to introduce an Nar I site.

Figure 18:
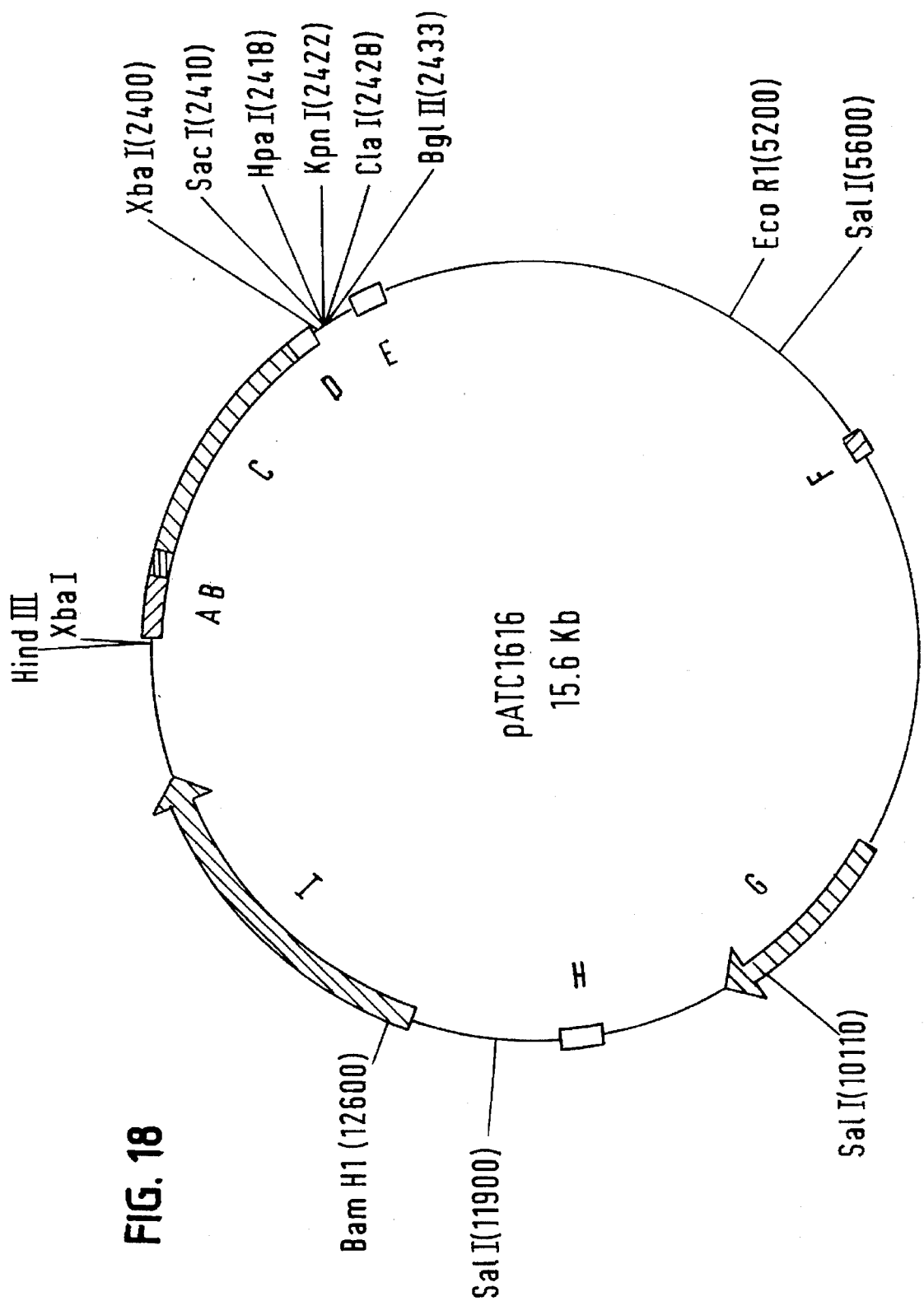

FIG. 18 is a schematic representation of the about 15.6 kb plasmid pATC1616, including a partial restriction enzyme map. In this figure, A–I are schematic representations of the following sequences: A=CaMV 35S promoter, B=transit peptide sequence, C=phytoene dehydrogenase-4H gene, D=NOS polyadenylation site, E=pBR322 ori, F=ori T, G=tetracyline resistance gene, H=ori V, and I=kanamycin resistance gene.

FIG. 19 shown in three panels as FIG. 19-1, FIG. 19-2 and FIG. 19-3 illustrates the DNA (SEQ ID NO:13) and a deduced amino acid residue (SEQ ID NO:14) sequences of the Erwinia herbicola structural gene for lycopene cyclase.

The Met codon (shown at position 19) corresponds to position 9002 on plasmid pARC376 in FIG. 5. The restriction sites Sph I and Bam HI were introduced at the 5' and 3' ends of the gene using PCR. The changes in the sequence for the genetically engineered version of the gene (SEQ ID NO:15) used for expression in yeast are shown in bold underneath the native sequence. At the 5' end of the gene, the native initiation GTG codon has been changed to an ATG codon. The second amino acid residue, Arg, was originally encoded by an AGG codon that was changed to a CGG codon, while retaining its coding for the Arg amino acid residue.

DETAILED DESCRIPTION OF THE INVENTION

A. Definition of Terms

Amino Acid

All amino acid residues identified herein are in the natural L-configuration. In keeping with standard polypeptide nomenclature, J. Biol. Chem., 243:3557-59, (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus.

Expression

The combination of intracellular processes, including transcription and translation undergone by a structural gene to produce a polypeptide.

Expression Vector

A DNA sequence that forms control elements that regulate expression of structural genes when operatively linked to those genes.

Operatively Linked or Inserted

A structural gene is covalently bonded in correct reading frame to another DNA (or RNA as appropriate) segment, such as to an expression vector so that the structural gene is under the control of the expression vector.

Promoter

A recognition site on a DNA sequence or group of DNA sequences that provide an expressions control element for a gene and to which RNA polymerase specifically binds and initiates RNA synthesis (transcription) of that gene.

Recombinant DNA Molecule

A hybrid DNA sequence comprising at least two nucleotide sequences not normally found together in nature.

Structural Gene

A DNA sequence that is expressed as a polypeptide, i.e., an amino acid residue sequence.

Vector

A DNA molecule capable of replication in a cell and/or to which another DNA segment can be operatively linked so as to bring about replication of the attached segment. A plasmid is an exemplary vector.

B. Introduction

Constituting the most widespread group of pigments, carotenoids are present in all photosynthetic organisms, where they are an essential part of the photosynthetic apparatus.

Mevalonic acid, the first specific precursor of all the terpenoids is formed from acetyl-CoA via HMG-CoA (3-hydroxy-3-methylglutaryl-CoA), and is itself converted to isopentenyl pyrophosphate (IPP), the universal isoprene unit. After isomerization of IPP to dimethylallyl pyrophosphate and a series of condensation reactions adding IPP, catalyzed by prenyltransferases, geranylgeranyl pyrophosphate (GGPP) is formed according to the scheme in FIG. 1. The formation of GGPP is the first step in carotenoid biosynthesis.

In the bacterium *Erwinia herbicola*, phytoene has now been found to be formed biosynthetically in a two-step progess as shown in FIG. 1. The initial step is the condensation of farnesyl pyrophosphate (FPP) and isopentenyl pyrophosphate (IPP) to form geranylgeranyl pyrophosphate (GGPP). This reaction is catalyzed by the enzyme geranylgeranyl pyrophosphate synthase (GGPP synthase). This first step is immediately followed by a tail to tail dimerization of GGPP, catalyzed by the enzyme phytoene synthase, to form phytoene. This pathway thus differs from the pathway reported in published European Application 0 393 690 wherein GGPP is said to form prephytoene pyrophosphate (a cyclopropylene-containing molecule) that thereafter is said to form phytoene.

Lycopene which has now been found to be the second carotenoid produced in *Erwinia herbicola* is produced from phytoene by the catalytic action of phytoene dehydrogenase-4H. Hence, the carotenoid-specific genes necessary for the synthesis of lycopene from farnesyl pyrophosphate include GGPP synthase, phytoene synthase, and phytoene dehydrogenase-4H.

The third carotenoid produced by *Erwinia herbicola* results from the cyclization of lycopene to form beta-carotene. Little is known about the reaction(s) involved in the cyclization of lycopene. Bramley et al, *Current Topics in Cellular Regulation* 29:291,297 (1988). In the system of the present invention, it is clear that only one enzyme is involved. This enzyme is lycopene cyclase. Thus, the genes required for beta-carotene production from farnesyl pyrophosphate include the above-named enzyme genes plus the gene for lycopene cyclase.

The present invention relates to these steps in the carotenoid pathway, the methods of isolating the *Erwinia herbicola* gene encoding lycopene cyclase and to the adaptation of this pathway by recombinant DNA technology to achieve heretofore unavailable methods and capabilities of beta-carotene production, particularly in host organisms that do not otherwise synthesize beta-carotene or that do synthesize beta-carotene, but in relatively small amounts or in specialized locations.

The disclosure below provides a detailed description of the isolation of carotenoid synthesis genes from *Erwinia herbicola*, modification of these genes by genetic engineering, and their insertion into compatible plasmids suitable for cloning and expression in *E. coli*, yeasts, fungi and higher plants. Also disclosed are methods for preparation of the appropriate enzymes and the methods for beta-carotene production in these various hosts.

Plasmid constructs are exemplified for several host systems. However, similar constructs utilizing the genes of this invention are available for virtually any host system as is well known in the art.

A structural gene or isolated purified DNA segment of this invention is often referred to as a restriction fragment bounded by two restriction endonuclease sites and containing a recited number of base pairs. A structural gene of this invention is also defined to include a sequence shown in a figure plus variants and analogs of such genes (described hereinafter), that hybridize non-randomly with a gene shown in the figure under normal stringency conditions described hereinafter. Each contemplated gene includes a recited non-randomly hybridizable variant or analog DNA sequence, encodes lycopene cyclase and also produces biologically active molecules of the encoded enzyme when suitably transfected into and expressed in an appropriate host.

Polynucleotide hybridization is a function of sequence identity (homology), G+C content of the sequence, buffer salt content, sequence length and duplex melt temperature ($T_m$) among other variables. See, Maniatis et al., *Molecular Cloning*, Cold Spring Harbor Laboratory, Cold Spring Harbor, N.Y. (1982), page 388.

With similar sequence lengths, the buffer salt concentration and temperature provide useful variables for assessing sequence identity (homology) by hybridization techniques. For example, where there is at least 90 percent homology, hybridization is carried out at 68° C. in a buffer salt such as 6XSCC diluted from 20XSSC [Maniatis et al., above, at page 447]. The buffer salt utilized for final Southern blot washes can be used at a low concentration, e.g., 0.1XSSC and at a relatively high temperature, e.g. 68° C., and two sequences will form a hybrid duplex (hybridize). Use of the above hybridization and washing conditions together are defined as conditions of high stringency or highly stringent conditions.

Moderately high stringency conditions can be utilized for hybridization where two sequences share at least about 80 percent homology. Here, hybridization is carried out using 6XSSC at a temperature of about 50°–55° C. A final wash salt concentration of about 1–3XSSC and at a temperature of about 60°–68° C. are used. These hybridization and washing conditions define moderately high stringency conditions.

Low stringency conditions can be utilized for hybridization where two sequences share at least 40 percent homology. Here, hybridization is carried out using 6XSSC at a temperature of about 40°–50° C., with a final wash buffer salt concentration of about 6XSSC at a temperature of about 40°–60° C. These hybridization and washing conditions define low stringency conditions.

An isolated DNA or RNA segment that contains a nucleotide sequence that is at least 80 percent, and more preferably at least 90 percent identical to a DNA sequence for lycopene cyclase shown in FIG. 19 (SEQ ID NO:13) is contemplated by this invention. Such a nucleotide sequence, when present in a host cell as part of a plasmid or integrated into the host genome as described herein, that also hybridizes non-randomly under at least moderately high stringency conditions and expresses biologically active lycopene cyclase is contemplated herein as a variant of an illustrated sequence that exhibits substantially the same biological activity.

In living organisms, the amino acid residue sequence of a protein or polypeptide is directly related via the genetic code to the deoxyribonucleic acid (DNA) sequence of the structural gene that codes for the protein. Thus, a structural gene can be defined in terms of the amino acid residue sequence; i.e., protein or polypeptide, for which it codes.

Thus, through the well-known redundancy of the genetic code, additional DNA and corresponding RNA sequences can be prepared that encode the same amino acid residue sequences, but are sufficiently different from a before-discussed gene sequence that the two sequences do not hybridize at high stringency, but do hybridize at moderately high stringency. Furthermore, allelic variants of a structural gene can exist in other *Erwinia herbicola* strains that are also useful, but form hybrid duplex molecules only at moderately high stringency.

A DNA or RNA sequence that (1) encodes an enzyme molecule exhibiting substantially the same biological activity as a lycopene cyclase molecule expressed by a DNA sequence of FIG. 19, (2) hybridizes with a DNA sequence of that figure at least at moderately high stringency and (3) shares at least 80 percent, and more preferably at least 90 percent, identity with a DNA sequence of that figure is defined as a DNA variant sequence.

Thus, a DNA variant or variant DNA is defined as including an RNA sequence.

Analog or analogous DNA and RNA sequences that encode the above enzyme proteins are also contemplated as part of this invention. A DNA and RNA sequence that encodes an amino acid residue sequence that is at least 40 percent, and more preferably at least 80 percent, and most preferably at least 90 percent, identical to that of an *Erwinia herbicola* lycopene cyclase shown in FIG. 19 that hybridizes with the structural gene illustrated in FIG. 19, herein under low stringency hybridization conditions but not at moderately high stringency are also contemplated, and are referred to herein as an "analog of" or "analogous to" a DNA sequence shown in a figure. A polynucleotide that encodes an analogous sequence must also produce functional or biologically active lycopene cyclase; i.e., an enzyme that converts lycopene to beta-carotene upon suitable transfection and expression. An analog or analogous DNA sequence is thus also defined as including an RNA sequence.

In comparing DNA sequences of *Erwinia herbicola* and *Erwinia uredovora*, the published European Application 0 393 690 reported no hybridization of DNA from *Erwinia uredovora* with DNA from *Erwinia herbicola* using highly stringent hybridization conditions. Present studies indicate a range of sequence identities of about 55 to about 70 percent between the sequences of that published European application and the sequences disclosed herein, with there being about a 59 percent identity between the two genes for lycopene cyclase. In spite of the 45 to 30 percent of mismatched base pairs, and the reported non-hybridization at high stringency of the *Erwinia herbicola* and *Erwinia uredovora* DNAs, the reported *Erwinia uredovora* DNA sequences and the *Erwinia herbicola* DNAs discussed herein, and particularly the DNA sequences encoding lycopene cyclase are DNA analogs of each other as the word "analog" is used herein.

Analogous DNA molecules that encode lycopene cyclase can be obtained from other organisms using hybridization and functionality selection criteria discussed herein.

For example, a microorganism, fungus, alga, or higher plant that is known or can be shown to produce beta-carotene is utilized as a DNA source. The total DNA of the selected organism is obtained and a genomic library is constructed in a λ phage such as λgt11 using the protocols discussed in Maniatis et al., *Molecular Cloning*, Cold Spring Harbor Laboratory, Cold Spring Harbor, N.Y. (1982) at pages 270–294.

The phage library is then screened under standard protocols using a radiolabeled, nick-translated DNA probe having a sequence of the *Erwinia herbicola* DNA of FIG. 19 and the before-discussed low stringency hybridization conditions. once the hybridization studies locate the appropriate structural gene, that structural gene DNA segment can be obtained, sequenced, engineered for expression in an appropriate recombinant molecule and shown to produce biologically active lycopene cyclase as is discussed elsewhere herein.

The above techniques and protocols are well known to workers skilled in molecular biology and need not be discussed further. It is noted, however, that the above procedure can also be used to obtain a variant DNA molecule that encodes lycopene cyclase inasmuch as DNA molecules that hybridize under conditions of low stringency also include those DNA molecules that hybridize under conditions of high and moderately high stringency.

That a DNA sequence variant or analog encodes a "biologically active" enzyme or an enzyme having "substantially the same biological activity" is determined by whether the variant or analog DNA sequence produces beta-carotenehydroxylase or zeaxanthin glycosylase as discussed herein. Thus, a DNA analog or variant sequence that expresses a lycopene cyclase molecule that converts provided lycopene into beta-carotene is defined as biologically active. Expression of biologically active lycopene cyclase from a variant or analog DNA sequence can be assayed by the production of beta-carotene.

An isolated DNA segment of the invention thus includes a DNA sequence that encodes *Erwinia herbicola* lycopene cyclase of a figure, a DNA variant or an analog thereof. In a preferred embodiment, that DNA segment includes a DNA sequence that encodes the lycopene cyclase in a DNA segment separate from any other carotenoid-forming enzyme encoding sequences. More preferably, a DNA segment contains the *Erwinia herbicola* lycopene cyclase structural gene, and is free from a functional gene whose expression product consumes beta-carotene production. A host transformed with such a DNA segment is also free from a functional gene whose product consumes beta-carotene or inhibits production of beta-carotene.

C. Genes Encoding Enzymes for Beta-Carotene Biosynthesis

1. Isolation of the carotenoid gene cluster

The plasmid pARC376 contains an approximately 13 kb chromosomal DNA fragment isolated by Perry et al. *J. Bacteriol.*, 168:607 (1986) from the bacterium *Erwinia herbicola* EHO-10 (*Escherichia vulneris*; ATCC 39368) that when transferred into the bacterium *E. coli* causes the *E. coli* cells to produce a yellow pigment. Plasmid pARC376 was referred to by those authors as plasmid pPL376. A restriction map of the pARC376 plasmid showing appropriate restriction sites is shown in FIG. 5.

The structural genes in the plasmid responsible for pigment production are present on a DNA fragment of about 7900 base pairs (bp) that is bounded by the restriction sites Pst I (at about position 4886) and Bgl II (at about position 12349) shown in FIG. 5. There are a total of six relevant genes in this approximately 7900 bp region that cause the *E. coli* cells to produce the carotenoid zeaxanthin diglucoside, which is the final product identified in the carotenoid pathway contained in plasmid pARC376 defined herein.

The biosynthetic pathway for the production of zeaxanthin diglucoside is shown in FIG. 1. *E. coli* cells, and all cells contemplated as hosts herein, naturally synthesize the isoprenoid intermediate farnesyl pyrophosphate (FPP). The genes for geranylgeranyl pyrophosphate (GGPP) synthase, phytoene synthase, phytoene dehydrogenase-4H, lycopene cyclase, beta-carotene hydroxylase, and zeaxanthin glycosylase are located in the approximately 7900 bp DNA fragment in pARC376. *E. coli* cells that are transformed with the plasmid pARC376 are able to convert some of the endogenous FPP into carotenoids by utilizing the enzymes encoded on the plasmid.

The following are descriptions of the individual structural genes, including the gene of this invention for lycopene cyclase, responsible for the synthesis of the carotenoid beta-carotene, and the recombinant DNA manipulations that have been performed to influence carotenoid biosynthesis in bacteria such as *E. coli*, yeast such as *S. cerevisiae* and higher plants.

2. GGPP Synthase Gene and Plasmid Constructs a. DNA segments

Participating in this invention in providing an intermediate, is an isolated, purified DNA segment comprising a nucleotide sequence of at least 850 base pairs that define a structural gene for the *Erwinia* enzyme GGPP synthase. A typical, useful DNA segment contains about 850 to about 1150 base pairs, whereas a more preferred DNA segment contains about 850 to about 1000 base pairs. The native sequence contains about 924 bp. Larger DNA segments are also contemplated and are discussed hereinafter.

An approximately 1153 bp fragment that extends from the Bgl II (about 12349) site to the Eco RV (about 11196) site of plasmid pARC376 is shown in FIG. 5. A preferred structural gene for GGPP synthase is within the about 1153 bp Bgl II to Eco RV restriction fragment shown in FIG. 5 and contains the previously mentioned native structural gene of about 924 bp. This structural gene is within the approximately 1029 bp Nco I-Eco RV restriction fragment of plasmid pARC417BH.

Surprisingly it has been found that a recombinant structural gene that encodes an amino-terminal truncated version of this enzyme in which the amino-terminal thirteen residues of the native enzyme were deleted and were replaced by four extraneous amino acid residues from the pARC306A vector was more active (about two times) than was a recombinantly produced enzyme having the encoded, native thirteen amino-terminal residues. This more active enzyme is encoded by the structural GGPP synthase gene containing about 1000 bp shown in FIG. 3, and is within the approximately 1150 bp segment Nco I-Pvu II restriction fragment of plasmid pARC489B.

Still more surprisingly, it has also been found that truncation of the carboxy-terminus of the GGPP synthase molecule made the enzyme still more active. Thus, use of a GGPP synthase structural gene of FIG. 3 from which the 3' Bal I-Eco RV fragment was removed provided the most active GGPP synthase found. This structural gene of about 850 bp is within the approximately 1000 bp Nco I-Pvu II restriction fragment of pARC489D. This GGPP synthase gene is most preferred herein. Details of the above work are described hereinafter.

The DNA sequence 1 from *Erwinia uredovora* in EP 0 393 690 is said there to encode the gene for converting prephytoene pyrophosphate to phytoene. The DNA sequence of that European application has about 59 percent identity with the GGPP synthase illustrated herein, and *Erwinia uredovora* DNA sequence 1, or any GGPP synhase gene can also be used herein for preparing GGPP.

b. Recombinant DNA Molecules

Also useful in this invention, are recombinant DNA molecules comprising a vector operatively linked to an exogenous DNA segment defining a structural gene capable of expressing the enzyme GGPP synthase, as described above, and a promoter suitable for driving the expression of the gene encoding the enzyme in a compatible host organism. The vector and promoter are as described elsewhere herein. Particularly preferred plasmid vectors include pARC417BH, pARC489B, pARC489D and pARC145G.

3. Phytoene Synthase Gene and Plasmid Construct a. DNA segments

An isolated, purified DNA segment comprising a nucleotide sequence of at least 927 base pairs that define a structural gene for the *Erwinia herbicola* enzyme phytoene synthase participates in this invention by providing phytoene (from GGPP) as an intermediate to production of β-carotene, as well as to production of the plant carotenoids lutein and neoxanthin. This structural gene typically contains about 927 bp of the native sequence, but can also contain a greater number as discussed hereinafter. The structural gene for phytoene synthase lies between positions 6383 and 5457 of plasmid pARC376 (FIG. 5).

A phytoene synthase gene useful herein at least includes a sequence shown in FIG. 4. In preferred practice, the structural gene also includes an upstream sequence shown in FIG. 4 from about position 8 (Bgl II site) to about position 15 (Nco I site).

A preferred phytoene synthase gene is within the about 1112 bp Nco I-Eco RI fragment of plasmid pARC285. Also included within that about 1112 bp segment is the approximately 1040 bp Nco I-Bam HI fragment that also encodes the desired structural gene.

The most preferred structural gene includes a nucleotide base sequence in FIG. 4 from about base 8 to about base 1040, and contains about 1030 bp. This most preferred gene is contained in the approximately 1176 base pair sequence of the Hpa I to Bam HI restriction sites and approximately 1238 bp Pvu II-Eco RI fragments present in the plasmid pARC140N, as well as in the approximately 1088 bp sequence of the Bgl II-Eco RI fragment of plasmid pARC140R.

A particularly preferred DNA segment is the approximately 2009 base pair Xba I-Xba I fragment present in plasmid pATC1615. This fragment contains an approximately 1242 base pair portion that encodes a chloroplast transit peptide of tobacco ribulose bis-phosphate carboxylase-oxygenase (hereinafter referred to as a chloroplast transit peptide) (about 177 bp) operatively linked in frame to the 5' end of the approximately 1065 bp Sph I-Sal I fragment, derived from plasmid pARC376 and modified as described in Example 9. That approximately 1242 bp fragment is flanked at its 5' end by an about 450 bp CaMV 35S promoter sequence and at its 3' end by an about 300 bp NOS polyadenylation sequence.

A further particularly preferred DNA segment is the approximately 3025 bp Hind III-Hind III fragment of plasmid pATC1620. This fragment contains an approximately 1242 bp portion that encodes the above chloroplast transit peptide operatively linked in frame to the 5' end of the approximately 1065 bp Sph I-Sal I fragment described in Example 9. That approximately 1242 bp fragment is flanked at its 5' end by an about 1483 bp NOS promoter sequence and at its 3' end by an about 300 bp NOS polyadenylation sequence.

The approximately 2009 bp Xba I-Xba I fragment present in plasmid pATC1615 and the approximately 3025 base pair Hind III-Hind III fragment present in plasmid pATC1620 can be used for expression of phytoene synthase in higher plants and transport of the expressed phytoene synthase into chloroplasts of higher plants such as tobacco. Infection of a higher plant such as tobacco with *A. tumefaciens* containing either plasmid pATC1615 or plasmid pATC1620 caused genomic incorporation of DNA for the. promoter, transit peptide-phytoene synthase and NOS polyadenylation sequence. Such incorporation enables the resulting plants to produce an increased amount of phytoene synthase and thereby phytoene, when the plants are maintained for a sufficient time period such as at least to the production of leaves. This maintenance period also permits enhanced lutein synthesis when compared to normal (native), non-transformed plants of the same type. The transformed plants also exhibit an increase in the amount of chlorophyll.

The approximately 2009 bp Xba I-Xba I fragment present in plasmid pATC1615 and the approximately 3025 bp Hind III-Hind III fragment present in plasmid pATC1620 can be further modified to remove the about 177 base pair chloroplast transit peptide. Transformation of higher plants with these modified gene segments incorporates DNA for the promoter, phytoene synthase and NOS polyadenylation sequence. Such incorporation enables the resulting plants to produce increased amounts of phytoene synthase and therefore phytoene in the plant cytoplasm, leading to an increase in the amount of lutein in these plants, when compared to normal (native), non-transformed plants of the same type.

The phrase "same type" is used herein to mean a plant of the same cross as or a clone of the transformed plant. Where alleic variations among siblings of a cross are small, as with extensively inbred plants, comparisons between siblings can be used or an average arrived at using several siblings. Otherwise, clones are preferred for the comparison.

EP 0 393 690 identifies its own *Erwinia uredovora* DNA sequence 5 as encoding an enzyme that converts GGPP into prephytoene pyrophosphate. Sequence 5 of that European application is about 64 percent identical to the before-discussed phytoene synthase gene, and that *Erwinia uredovora* gene or any phytoene synthase structural gene can be used herein for the synthesis of phytoene.

b. Recombinant DNA molecules

A recombinant DNA molecule, comprising a vector operatively linked to an exogenous DNA segment defining a structural gene capable of expressing the enzyme phytoene synthase, as discussed above, and a promoter suitable for driving the expression of the gene in a compatible host organism, is also useful in this invention. The vector and promoter of this recombinant molecule are also as are discussed herein. Particulary preferred plasmid vectors include pARC285, pARC140N and pARC145G.

4. Phytoene Dehydrogenase-4H Gene and Plasmid Construct a. DNA Segment

Contributing to this invention by providing the substrate is an isolated DNA segment comprising a nucleotide sequence that contains at least about 1470 base pairs (bp), including a sequence defining a structural gene capable of expressing the *Erwinia herbicola* enzyme phytoene dehydrogenase-4H. This phytoene dehydrogenase-4H enzyme has a molecular mass of about 51,000 daltons, which corresponds to a minimum size of about 1400 bp for the structural gene, presuming an average amino acid residue weight of about 109. The native phytoene dehydrogenase-4H structural gene contains about 1470 bp and is located between positions 7849 and 6380 of plasmid pARC376.

A typical, useful DNA segment contains about 1500 base pairs and lies within the approximately 1891 bp Ava I (8231) to Nco I (6342) DNA fragment from pARC376 illustrated in FIG. 5. Larger DNA segments are also contemplated, as discussed hereinafter.

A preferred DNA segment includes a nucleotide base sequence shown in FIG. 11 from about base 5 to about base 1470. Particularly preferred DNA segments include the bases between the engineered Nco I site at about position 7 of FIG. 11-1 (the initial Met residue) and about position 1470 of FIG. 11-4, and is present in the approximately 1505 bp Nco I-Nco I restriction fragment (Nco I fragment) of plasmid pARC496A, the approximately 1508 bp Sal I-Sal I restriction fragment (Sal I fragment) of plasmid pARC146D, and the approximately 1506 bp Sph I-Nco I fragment present in plasmid pATC228. The sequence of the about 1508 bp Sal I fragment is illustrated in FIG. 15.

A still further particularly preferred DNA segment is the approximately 2450 bp Xba I-Xba I fragment present in plasmid pATC1616. This fragment contains an approximately 1683 bp portion that encodes a chloroplast transit peptide of tobacco ribulose bis-phosphate carboxylase-oxygenase (hereinafter referred to as a chloroplast transit peptide) (about 177 bp) operatively linked in frame to the 5' end of the above Sph I-Nco I about 1506 bp phytoene dehydrogenase-4H gene. That approximately 1683 bp fragment is flanked at its 5' end by an about 450 bp CaMV 35S promoter sequence and at its 3' end by an about 300 bp NOS polyadenylation sequence.

This DNA segment can be used for expression of phytoene dehydrogenase-4H in higher plants and transport 6f the expressed phytoene dehydrogenase-4H into chloroplasts such as those of tobacco. Infection of a higher plant such as tobacco with *A. tumefaciens* containing plasmid pATC1616 caused genomic incorporation of DNA for the promoter, transit peptide-phytoene dehydrogenase-4H and NOS sequence, and makes the resultant plants resistant to the herbicide norflurazon.

It is noted that restriction fragments having the same restriction enzyme cleavage sequence at both the 5' and 3' ends are sometimes referred to herein by reference to a single restriction enzyme. Thus, the approximately 1505 bp Nco I-Nco I restriction fragment referred to above can also be referred to herein as an approximately 1505 bp Nco I fragment. Similarly, the approximately 1508 bp Sal I-Sal I fragment can be referred to as the approximately 1508 bp Sal I fragment, and the approximately 2450 bp Xba I-Xba I fragment can be referred to as the approximately 2450 bp Xba I fragment.

EP 0 393 690 identifies its own *Erwinia uredovora* DNA sequence 4 as encoding an enzyme that converts phytoene into lycopene. Sequence 4 of that European application is about 69 percent identical to the before-discussed phytoene dehydrogenase-4H gene, and that *Erwinia uredovora* gene or any phytoene dehydrogenase-4H structural gene can be used herein for the synthesis of lycopene.

b. Recombinant DNA Molecules

A recombinant DNA molecule comprising a vector operatively linked to an exogenous DNA segment defining a structural gene capable of expressing the enzyme phytoene dehydrogenase-4H and a promoter suitable for driving the expression of the enzyme in a compatible host organism is also contemplated by this invention. The structural gene has a nucleotide base sequence described above., Particularly preferred plasmids include pARC49A, pARC146D, pATC228 and pATC1616.

5. Lycopene Cyclase Gene and Plasmid Construct a. DNA Segment

Contemplated by this invention is an isolated DNA segment comprising a nucleotide sequence that contains at least about 1125 base pairs (bp), including a sequence defining a structural gene capable of expressing the *Erwinia herbicola* enzyme lycopene cyclase. This lycopene cyclase enzyme has a molecular mass of about 39,000 daltons, and converts lycopene to beta-carotene.

A typical, useful DNA segment contains about 1125 base pairs and preferably at least 1150 base pairs and lies within the approximately 1548 bp Sal I (9340) to Pst I (7792) DNA fragment from pARC376 illustrated in FIG. 5. The native *Erwinia herbicola* structural gene for lycopene cyclase contains about 1125 base pairs and is located between positions 9002 and 7878 of pARC376. Larger DNA segments are also contemplated, as discussed hereinafter.

A preferred DNA segment includes a nucleotide base sequence shown in FIG. 19, panels 1–3, from about base 19 to about base 1234. A preferred variant sequence of 1140 bp is present in the approximately 1142 bp Sph I-Bam HI restriction fragment of the plasmid pARC1509, shown in FIG. 19. A further preferred variant sequence is present in the approximately 1210 bp Nco I-Pst I restriction fragment of plasmid. pARC147. As is shown in the examples, biologically active lycopene cyclase was produced using the native DNA as well as two variant DNA sequences.

A particularly preferred DNA segment is an approximately 2069 bp Xba I-Xba I fragment present in plasmid pARC1512. This fragment contains an approximately 1319 bp portion that includes about 177 bp that encode a chloroplast transit peptide operatively linked in frame to the 5' end of the variant approximately 1142 bp Sph I-Bam HI fragment, derived from plasmid pARC1509 that encodes lycopene cyclase. That approximately 1319 bp fragment is flanked at its 5' end by an about 450 bp CaMV 35S promoter sequence and at its 3' end by an about 300 bp NOS polyadenylation sequence.

The approximately 2069 bp Xba I-Xba I fragment present in plasmid pARC1512 can be used for expression of lycopene cyclase in higher plants and transport of the expressed lycopene cyclase into chloroplasts of higher plants such as tobacco. Infection of a higher plant such as tobacco with *A. tumefaciens* containing plasmid pARC1512 caused genomic incorporation of DNA for the promoter, transit peptide-lycopene cyclase and NOS polyadenylation sequence. Such incorporation enabled the resulting plants to produce increased amounts of lycopene cyclase when the plants were maintained for a sufficient time period such as at least to the production of leaves. This maintenance period also permitted enhanced total carotenoid synthesis when compared to normal (native or wild type), non-transformed plants of the same type.

The approximately 2069 bp Xba I-Xba I fragment present in plasmid pARC1512 can be further modified to remove the about 177 bp chloroplast transit peptide. Transformation of higher plants with this modified gene segment incorporates DNA for the promoter, lycopene cylcase and NOS polyadenylation sequence. Such incorporation enables the resulting plants to produce increased amounts of lycopene cyclase in the plant cytoplasm leading to an increase in the amount of total carotenoids in these plants, when compared to normal (native or wild type), non-transformed plants of the same type.

The phrase "same type" is used to mean a plant of the same cross as or a clone of the transformed plant. Where allelic variations among siblings of a cross are small, as with extensively inbred plants, comparisons between siblings can be used or an average arrived at using several siblings. Otherwise, clones are preferred for the comparison.

EP 0 393 690 identifies its own *Erwinia uredovora* DNA sequence 3 as encoding an enzyme that covnerts lycopene into beta-carotene. Sequence 3 of that European application is about 59 percent identical to the before-discussed lycopene cylcase structural gene, and that *Erwinia uredovora* gene or any lycopene cylase structural gene can be used herein for the synthesis of beta-carotene.

b. Recombinant DNA Molecules

A recombinant DNA molecule comprising a vector operatively linked to an exogenous DNA segment defining a structural gene capable of expressing the *Erwinia* enzyme lycopene cyclase and a promoter suitable for driving the expression of that enzyme in a compatible host organism, is also contemplated by this invention. The structural gene has a nucleotide base sequence described above. Particularly preferred plasmid vectors include pARC1510, pARC1520 and pARC1509.

6. DNA Size

The previously described DNA segments are noted as having a minimal length, as well as total overall lengths. That minimal length defines the length of a DNA segment having a sequence that encodes a particular protein enzyme. Inasmuch as the coding sequences for each of the four genes disclosed herein are illustrated in the accompanying figures, isolated DNA segments, variants and analogs thereof can be prepared by in vitro mutagenesis, as described in the examples, that begin at the initial ATG codon for a gene and end at or just downstream of the stop codon for each gene. Thus, a desired restriction site can be engineered at or upstream of the initiation codon, and at or downstream of the stop codon so that shorter structural genes than most of those discussed above can be prepared, excised and isolated.

As is well known in the art, so long as the required DNA sequence is present, (including start and stop signals), additional base pairs can be present at either end of the segment and that segment can still be utilized to express the protein. This, of course, presumes the absence in the segment of an operatively linked DNA sequence that represses expression, expresses a further product that consumes the protein desired to be expressed, expresses a product that consumes a wanted reaction product produced by that desired protein, or otherwise interferes with the structural gene of the DNA segment.

Thus, so long as the DNA segment is free of such interfering DNA sequences, a DNA segment of the invention can be 2,000–15,000 base pairs in length. The maximum size of a recombinant DNA molecule, particularly an expression vector, is governed mostly by convenience and the vector size that can be accommodated by a host cell, once all of the minimal DNA sequences required for replication and expression, when desired, are present. Minimal vector sizes are well known. Such long DNA segments are not preferred, but can be used.

Example 5b illustrates that a DNA segment of several thousand base pairs that contains the structural genes for GGPP synthase and phytoene synthase can be used to produce phytoene. The same situation is true for phytoene dehydrogenase-4H production as is seen in Example 11b. The DNA segment used in Example 11b contains structural genes for GGPP synthase, phytoene synthase and phytoene dehydrogenase-4H, lycopene cyclase and the other structural genes for zeaxanthin preparation. However, the gene for lycopene cyclase, which utilizes lycopene, was impaired so that no functional lycopene cyclase was produced and lycopene accumulated. A similar situation is illustrated in Example 18b wherein the gene for β-carotene hydroxylase originally present in plasmid pARC376 was made inoperative and β-carotene was found to accumulate.

7. Construction of Plasmids a. DNA segments

DNA segments that encode the before-described enzyme proteins can be synthesized by chemical techniques, for example, the phosphotriester method of Matteucci et al., *J. Am. Chem. Soc.*, 103:3185 (1981). (The disclosures of the art cited herein are incorporated herein by reference.) Of course, by chemically synthesizing the coding sequence, any desired modifications can be made simply by substituting the appropriate bases for those encoding the native amino acid residue sequence. However, DNA segments including sequences discussed previously are preferred.

Furthermore, DNA segments containing structural genes encoding the enzyme proteins can be obtained from recombinant DNA molecules (plasmid vectors) containing those genes. For instance, the plasmid type recombinant DNA molecules pARC417BH, pARC489B, pARC489D, pARC285, and pARC140N each contain DNA sequences encoding different portions of the GGPP synthase and phytoene synthase proteins and together possess the entire sequence of DNA necessary for expression of either protein in biologically active form. Plasmid pARC145G contains DNA segments encoding both enzymes. In addition, the plasmid type recombinant DNA molecules pARC496A, pARC146D, pATC228 and pATC1616 each contain a DNA sequence encoding biologically active phytoene dehydrogenase proteins. Similarly, the plasmid type recombinant DNA molecules pARC1509, pARC1510, and pARC1520 each contain a DNA sequence encoding biologically active lycopene cyclase proteins.

Plasmids pARC417BH, pARC489B, pARC489D, pARC285, pARC140N and pARC145G have been deposited pursuant to Budapest Treaty requirements with the American Type Culture Collection (ATCC) 12301 Parklawn Drive, Rockville, Md. 20852 on February 26, 1990 and were assigned the following respective accession numbers 40755, 40758, 40757, 40756, 40759, and 40753. Plasmids pARC496A, pARC146D and pATC228 were deposited pursuant to Budapest Treaty requirements with the American Type Culture Collection, (ATCC) 12301 Parklawn Drive, Rockville, Md. 20852 on May 11, 1990 and were assigned the following respective accession numbers 40803, 40801 and 40802. Plasmid pATC1616 was similarly deposited on May 15, 1990 and was assigned accession No. 40806. Also, plasmids pARC1509, pARC1510, and pARC1520 were deposited pursuant to Budapest Treaty requirements with the American Type Culture Collection, (ATCC) 12301 Parklawn Driver Rockville, Md. 20852 on Jul. 27, 1990 and were assigned the following respective accession numbers 40850, 40851 and 40852.

A DNA segment that includes a DNA sequence encoding lycopene cyclase, phytoene dehydrogenase-4H, GGPP synthase, and phytoene synthase can be prepared by excising and operatively linking appropriate restriction fragments from each of the above deposited plasmids using well known methods. The DNA molecules of the present invention produced in this manner typically have cohesive termini, i.e., "overhanging" single-stranded portions that extend beyond the double-stranded portion of the molecule. The presence of cohesive termini on the DNA molecules of the present invention is preferred, although molecules having blunt termini are also contemplated.

Ribonucleic acid (RNA) equivalents of the above described DNA segments are also contemplated.

b. Recombinant DNA Molecules

A recombinant DNA molecule of the present invention can be produced by operatively linking a vector to a DNA segment of the present invention to form a plasmid such as those discussed and deposited herein. Particularly preferred recombinant DNA molecules are discussed in detail in the examples, hereafter. Vectors capable of directing the expression of GGPP synthase, phytoene synthase, phytoene dehydrogenase-4H and/or lycopene cyclase genes are referred to herein as "expression vectors".

The expression vectors described above contain expression control elements including the promoter. The polypeptide coding genes are operatively linked to the expression vector to allow the promoter sequence to direct RNA polymerase binding and expression of the desired polypeptide coding gene. Useful in expressing the polypeptide coding gene are promoters which are inducible, viral, synthetic, constitutive as described by Poszkowski et al., *EMBO J.*, 3:2719' (1989) and Odell et al., *Nature*, 313:810' (1985), and temporally regulated, spatially regulated, and spatiotemporally regulated as given in Chua et al., *Science*, 244:174–181 (1989).

The choice of which expression vector and ultimately to which promoter a polypeptide coding gene is operatively linked depends directly on the functional properties desired, e.g. the location and timing of protein expression, and the host cell to be transformed. These are well known limitations inherent in the art of constructing recombinant DNA molecules. However, a vector useful in practicing the present invention is capable of directing the replication, and preferably also the expression (for an expression vector) of the polypeptide coding gene included in the DNA segment to which it is operatively linked.

In one preferred embodiment, a vector includes a prokaryotic replicon; i.e., a DNA sequence having the ability to direct autonomous replication and maintenance of the recombinant DNA molecule extrachromosomally in a prokaryotic host cell transformed therewith. Such replicons are well known in the art.

Those vectors that include a prokaryotic replicon can also include a prokaryotic promoter region capable of directing the expression of the GGPP synthase, phytoene synthase, phytoene dehydrogenase-4H or lycopene cyclase genes in a host cell, such as *E. coli*, transformed therewith. Promoter sequences compatible with bacterial hosts are typically provided in plasmid vectors containing one or more convenient restriction sites for insertion of a DNA segment of the present invention. Typical of such vector plasmids are pUC8, pUC9, and pBR329 available from Biorad Laboratories, (Richmond, Calif.) and pPL and pKK223-3 available from Pharmacia, Piscataway, N.J. A particularly preferred promoter for use in prokaryotic cells such as *E. coli* is the Rec 7 promoter present in plasmid vectors pARC306A, pARC496A and pARC136, and inducible by exogenously supplied nalidixic acid.

Expression vectors compatible with eukaryotic cells, preferably those compatible with yeast cells or more preferably those compatible with cells of higher plants, are also contemplated herein. Such expression vectors can also be used to form the recombinant DNA molecules of the present invention. Vectors for use in yeasts such as *S. cerivisiae* can be episomal or integrating, as is well known. Eukaryotic cell expression vectors are well known in the art and are available from several commercial sources.

Normally, such vectors contain one or more convenient restriction sites for insertion of the desired DNA segment and promoter sequences. Exemplary promoters for use in *S. cerevisiae* include the *S. cerevisiae* phosphoglyceric acid kinase (PGK) promoter and the divergent promoters GAL 10 and GAL 1.

Typical vectors useful for expression of genes in higher plants are well known in the art and include vectors derived from the tumor-inducing (Ti) plasmid of *Agrobacterium tumefaciens* described by Rogers et al., *Meth. in Enzymol.*, 153:253–277 (1987). However, several other expression vector systems are known to function in plants including pCaMVCN transfer control vector described by Fromm et al., *Proc. Natl. Acad. Sci. USA*, .82:58-24 (1985). Plasmid pCaMVCN (available from Pharmacia, Piscataway, N.J.) includes the cauliflower mosaic virus CaMV 35S promoter. The introduction of genes into higher plants is discussed in greater detail hereinafter.

The use of retroviral expression vectors to form the recombinant DNAs of the present invention is also contemplated. As used herein, the term "retroviral expression vector" refers to a DNA molecule that includes a promoter sequence derived from the long terminal repeat (LTR) region of a retrovirus genome.

Since some of these carotenoid products are to be associated with food production and coloration, the retroviral expression vector is preferably replication-incompetent in eukaryotic cells. The construction and use of retroviral vectors has been described by Verma, PCT Publication No. WO87/00551, and Cocking et al, *Science*, 236:1259-62 (1987).

In preferred embodiments, the vector used to express the polypeptide coding gene includes a selection marker that is effective in a plant cell, preferably a drug resistance selection marker. One preferred drug resistance marker is the gene whose expression results in kanamycin resistance, i.e., the chimeric gene containing the nopaline synthase promoter, Tn5 neomycin phosphotransferase II and nopaline synthase 3' nontranslated region described by Rogers et al., in *Methods For Plant Molecular Biology*, A. Weissbach and H. Weissbach, eds., Academic Press Inc., San Diego, Cal. (1988). Another preferred marker is the assayable chloramphenicol acetyltransferase (CAT) gene from the transposon Tn9.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the expression vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase. Thus, the products of the reaction are DNA segments carrying synthetic linker sequences at their ends. These DNA segments are then cleaved with the appropriate restriction endonuclease and ligated into an expression vector that has been cleaved with an enzyme that produces termini compatible with those of the synthetic linker. Synthetic linkers containing a variety of restriction endonuclease sites are commercially available from a number of sources including New England BioLabs, Beverly, Mass.

Also contemplated by the present invention are RNA equivalents of the above described recombinant DNA molecules.

c. Introducing genes into higher plants

Methods for introducing polypeptide coding genes into higher, multicelled plants include Agrobacterium-mediated plant transformation, protoplast transformation, gene transfer into pollen, injection into reproductive organs and injection into immature embryos. Each of these methods has distinct advantages and disadvantages. Thus, one particular method of introducing genes into a particular plant species may not necessarily be the most effective for another plant species, but it is well known which methods are useful for a particular plant species.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated expression vectors to introduce DNA into plant cells is well known in the art. See, for example, the methods described by Fraley et al., *Biotechnology*, 3:629 (1985) and Rogers et al., *Methods in Enzymology*, 153:253–277 (1987). Further, the integration of the Ti-DNA is a relatively precise process resulting in few rearrangements. The region of DNA to be transferred is defined by the border sequences, and intervening DNA is usually inserted into the plant genome as described by Spielmann et al., *Mol. Gen. Genet.*, 205:34 (1986) and Jorgensen et al., *Mol. Gen. Genet.*, 207:471 (1987).

Modern *Agrobacterium* transformation vectors are capable of replication in *E. coli* as well as *Agrobacterium*, allowing for convenient manipulations as described by Klee et al., in *Plant DNA Infectious Agents*, T. Hohn and J. Schell, eds., Springer-Verlag, New York (1985) pp. 179–203.

Moreover, recent technological advances in vectors for *Agrobacterium*-mediated gene transfer have improved the arrangement of genes and restriction sites in the vectors to facilitate construction of vectors capable of expressing various polypeptide coding genes. The vectors described by Rogers et al., *Methods in Enzymology*, 153:253 (1987), have convenient multi-linker regions flanked by a promoter and a polyadenylation site for direct expression of inserted polypeptide coding genes and are suitable for present purposes.

In those plant species where *Agrobacterium*-mediated transformation is efficient, it is the method of choice because of the facile and defined nature of the gene transfer. However, few monocots appear to be natural hosts for *Agrobacterium*, although transgenic plants have been produced in asparagus using *Agrobacterium* vectors as described by Bytebier et al., *Proc. Natl. Acad. Sci. U.S.A.*, 84:5345 (1987). Therefore, commercially important cereal grains such as rice, corn, and wheat must be transformed using alternative methods.

Higher plants have the ability to produce carotenoids. The site of synthesis for all plant carotenoids is in the chloroplast. Carotenoid biosynthesis is highly regulated in plants. Masoner et al., *Planta* 105:267 (1972); Frosch et al., *Planta* 148:279 (1980); Mohr, *Photosynthesis V. Chloroplast Development*, pp. 869–883 (1981); Oelmueller et al., *Planta* 164:390 (1985); Harpster et al., *Physiol. Plant.* 64:147 (1985); Steinmueller et al., *Molecular Form and Function of the Plant Genome*, pp. 277–290 (1986). Therefore, the ability to use recombinant DNA technology to increase endogenous carotenoid biosynthesis is questionable unless a novel approach is used. However, using the genes for GGPP synthase, phytoene synthase, phytoene dehydrogenase-4H and lycopene cyclase to induce beta-carotene synthesis in the cytoplasm is a viable approach, even though carotenoids are not naturally produced in the cytoplasm.

*Agrobacterium*-mediated transformation of leaf disks and other tissues appears to be limited to plant species that *Agrobacterium* naturally infects. Thus, *Agrobacterium*-mediated transformation is most efficient in dicotyledonous plants. However, as mentioned above, the transformation of asparagus using *Agrobacterium* can also be achieved. See, for example, Bytebier, et al., *Proc. Natl. Acad. Sci.*, 84:5345 (1987).

Transformation of plant protoplasts can be achieved using methods based on calcium phosphate precipitation, polyethylene glycol treatment, electroporation, and combinations of these treatments. See, for example, Potrykus et al., *Mol. Gen. Genet.*, 199:183 (1985); Lorz et al., *Mol. Gen. Genet.*, 199:178 (1985); Fromm et al., *Nature*, 319:791 (1986); Uchimiya et al., *Mol. Gen. Genet.*, 204:204 (1986); Callis et al., *Genes and Development*, 1:1183 (1987); and Marcotte et al., *Nature*, 335:454 (1988).

Application of these systems to different plant species depends upon the ability to regenerate that particular plant species from protoplasts. Illustrative methods for the regeneration of cereals from protoplasts are described in Fujimura et al., *Plant Tissue Culture Letters*, 2:74 (1985); Toriyama et al., *Theor Appl. Genet.*, 73:16 (1986); Yamada et al., *Plant Cell Rep.*, 4:85 (1986); Abdullah et al., *Biotechnology*, 4:1087 (1986).

To transform plant species that cannot be successfully regenerated from protoplasts, other ways to introduce DNA into intact cells or tissues can be utilized. For example, regeneration of cereals from immature embryos or explants can be effected as described by Vasil, *Biotechnology*, 6:397 (1988). In addition, "particle gun" or high-velocity microprojectile technology can be utilized. Using such technology: DNA is carried through the cell wall and into the cytoplasm on the surface of small metal particles as described in Klein et al., *Nature*, 327:70 (1987); Klein et al., *proc. Natl. Acad. Sci. U.S.A.*, 85:8502 (1988); and McCabe et al., *Biotechnology*, 6:923 (1988). The metal particles penetrate through several layers of cells and thus allow the transformation of cells within tissue explants.

Metal particles have been used to successfully transform corn cells and to produce fertile, stably transformed tobacco and soybean plants. Transformation of tissue explants eliminates the need for passage through a protoplast stage and thus speeds the production of transgenic plants.

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol. Reporter*, 6:165 (1988). Expression of polypeptide coding genes can be obtained by injection of the DNA into reproductive organs of a plant as described by Pena et al., *Nature*, 325:274 (1987). DNA can also be injected directly into the cells of immature embryos and the rehydration of desiccated embryos as described by Neuhaus et al., *Theor. Apl. Genet.*, 75:30 (1987); and Benbrook et al., in *Proceedings Bio Expo* 1986, Butterworth, Stoneham, Mass., pp. 27–54 (1986).

The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process includes the steps I of selection of transformant cells and shoots, rooting the transformant shoots and growth of the plantlets in soil.

The regeneration of plants containing the foreign gene introduced by *Agrobacterium* from leaf explants can be achieved as described by Horsch et al., *Science*, 227:1229–1231 (1985). In this procedure, transformants are grown in the presence of a selection agent and in a medium that induces the regeneration of shoots in the plant species being transformed as described by Fraley et al., *Proc. Natl. Acad. Sci. U.S.A.*, 80:4803 (1983).

This procedure typically produces shoots within two to four weeks and these transformant shoots are then transferred to an appropriate root-inducing medium containing the selective agent and an antibiotic to prevent bacterial growth. Transformant shoots that rooted in the presence of the selective agent to form plantlets are then transplanted to soil or other media to allow the production of roots. These procedures vary depending upon the particular plant species employed, such variations being well known in the art.

A plant of the present invention containing the desired enzyme proteins comprised of a first enzyme, GGPP synthase, a second enzyme, phytoene synthase, a third enzyme, phytoene dehydrogenase-4H, and a fourth enzyme lycopene cyclase is cultivated using methods well known to one skilled in the art. Any of the transgenic plants of the present invention can be cultivated to isolate the desired carotenoid products they contain.

After cultivation, the transgenic plant is harvested to recover the carotenoid product. This harvesting step can consist of harvesting the entire plant, or only the leaves, or roots of the plant. This step can either kill the plant or if only a non-essential portion of the transgenic plant is harvested can permit the remainder of the plant to continue to grow.

In preferred embodiments this harvesting step further comprises the steps of:
(i) homogenizing at least a carotenoid-containing portion of the transgenic plant to produce a plant pulp and using the carotenoid-containing pulp directly, as in dried pellets or tablets as where an animal food is contemplated; or
(ii) extracting the carotenoid(s) from the plant pulp with an appropriate solvent such as an organic solvent or by supercritical extraction [Favati et al., *J. Food. Sci.*, 53:1532 (1988) and the citations therein] to produce a carotenoid-containing liquid solution or suspension; and
(iii) isolating the carotenoid(s) from the solution or suspension.

The carotenoid isolated in step (iii), above, is at least beta-carotene, although other carotenoids produced can also be isolated and separated as is discussed hereinafter.

At least a portion of the transgenic plant is homogenized to produce a plant pulp using methods well known to one skilled in the art. This homogenization can be done manually, by a machine, or by a chemical means as long as the transgenic plant portions are broken up into small pieces to produce a plant pulp. This plant pulp consists of a mixture of the carotenoid of interest (beta-carotene), residual amounts of precursors, cellular particles and cytosol contents. This pulp can be dried and compressed into pellets or tablets and eaten or otherwise used to derive the benefits, or the pulp can be subjected to extraction procedures.

The beta-carotene can be extracted from the plant pulp produced above to form a beta-carotene-containing solution or suspension. Such extraction processes are common and well known to one skilled in this art. For example, the extracting step can consist of soaking or immersing the plant pulp in a suitable solvent. This suitable solvent is capable of dissolving or suspending the beta-carotene present in the plant pulp to produce a beta-carotene-containing solution or suspension. Solvents useful for such an extraction process are well known to those skilled in the art and include water, several organic solvents and combinations thereof such as methanol, ethanol, isopropanol, acetone, acetonitrile, tetrahydrofuran (THF), hexane, and chloroform. A vegetable oil such as peanut, corn, soybean and similar oils can also be used for this extraction.

Isolation (harvesting) of carotenoids from bacteria, yeasts, fungi and other lower organisms is illustrated hereinafter using *A. tumefaciens* and *E. coli*. Broadly, cells transfected with structural genes for GGPP synthase, phytoene synthase, phytoene dehydrogenase-4H and lycopene cyclase are grown under suitable conditions for a period of time sufficient for beta-carotene to be synthesized. The beta-carotene-containing cells, preferably in dried form, are then lysed chemically or mechanically, and the beta-carotene is extracted from the lysed cells using a liquid organic solvent, as described before, to form a beta-carotene-containing liquid solution or suspension. The beta-carotene is thereafter isolated from the liquid solution or suspension by usual means such as chromatography.

The beta-carotene is isolated from the solution of suspension produced above using methods that are well known to those skilled in the art of carotenoid isblation. These methods include, but are not limited to, purification procedures based on solubility in various liquid media, chromatographic techniques such as column chromatography and the like.

D. Methods for Preparing Beta-Carotene Synthesis Enzymes

1. Introduction a. Transformed Cells and Cultures

The present invention also relates to host cells transformed with recombinant DNA molecules of the present invention, preferably recombinant DNA capable of expressing GGPP synthase and membrane-bound (or soluble) phytoene synthase, phytoene dehydrogenase-4H and lycopene cyclase enzymes. These four enzymes can be referred to as beta-carotene synthesis enzymes.

The host cells can be either prokaryotic or eukaryotic. Bacterial cells are preferred prokaryotic host cells and typically are a strain of *E. coli* such as, for example the *E. coli* strain HB101, available from BRL Life Technologies, Inc., Gaithersburg, Md. (BRL). Preferred eukaryotic host cells include yeast and plant cells or protoplasts, preferably cells from higher plants. Preferred eukaryotic host cells include *S. cerevisiae* cells such as YPH499 obtained from Dr. Phillip Hieter, Johns Hopkins University, Baltimore, Md., discussed in Example 6.

Transformation of appropriate cell hosts with a recombinant DNA molecule of the present invention is accomplished by well known methods that typically depend on the type of vector used. With regard to transformation of prokaryotic host cells, see, for example, Cohen et al., *Proc. Natl. Acad. Sci. USA*, 69:2110 (1972); and Maniatis et al., *Molecular Cloning, A Laboratory Manual*, Cold Spring Harbor Laboratory, Cold Spring Harbor, N.Y. (1982). With regard to transformation of plant cells with retroviral vectors containing recombinant DNAs, see, for example, Verma, PCT Publication No. WO 87/00551, 1987, who isolated protoplasts from plant tissue, and inserted the retroviral genome in proviral (double stranded) form into the genome of the protoplasts. The transformed protoplasts were developed into callus tissue and then regenerated into transgenic plants. Plants derived from the protoplasts and their progeny carry the genetic material of the recombinant retroviral vector in their genomes and express the protein product.

Successfully transformed cells, i.e., cells that contain a recombinant DNA molecule of the present invention, can be identified by well known techniques. For example, cells resulting from the introduction of a recombinant DNA of the present invention can be cloned to produce monoclonal colonies. Cells from those colonies can be harvested, lysed and their DNA content examined for the presence of the recombinant DNA using a method such as that described by Southern, *J. Mol. Biol.*, 98:503 (1975) or Berent et al., *Biotech.*, 3:208 (1985).

In addition to directly assaying for the presence of recombinant DNA, successful transformation can be confirmed by well known immunological methods when the recombinant DNA is capable of directing the expression of specific protein antigens. For example, cells successfully transformed with an expression vector may produce proteins displaying GGPP synthase, phytoene synthase, phytoene dehydrogenase-4H or lycopene cyclase antigenicity.

Identifying successful transformation of *E. coli* in this invention is relatively easy for carotenoids, except phytoene. Carotenoid-containing colonies formed are usually characterized by Colored pigment formation. For example, beta-carotene is yellow and lycopene is red.

b. Methods for Producing Enzymes

A method is contemplated by this invention for preparing the enzyme lycopene cyclase. This method comprises initiating a culture, in a nutrient medium, of transformed prokaryotic or eukaryotic host cells. The host cells are transformed with a recombinant DNA molecule Containing a compatible expression vector operatively linked to a before-described exogenous DNA segment that defines the structural gene for lycopene cyclase.

This invention further comprises cultures maintained for a time period sufficient for the host cells to express the lycopene cyclase protein molecules, which proteins can be recovered in purified form if desired. Nutrient media useful for culturing transformed host cells are well known in the art and can be obtained from several commercial sources.

A further aspect contemplated is a method for preparing lycopene cyclase in the presence of either or all of GGPP synthase, phytoene synthase and phytoene dehydrogenase-4H. This method is substantially identical to the before-described method except that the host cells are also transformed with a compatible expression vector operatively linked to a before-described exogenous DNA segment that defines any or all of the structural genes for GGPP synthase, phytoene synthase and phytoene dehydrogenase-4H.

The transformed host cell can contain a single expression vector that contains all four structural genes, including the structural gene for lycopene cyclase. The host can also be transformed with two expression vectors containing structural genes for the four enzymes, one for at least lycopene cyclase and another that contains the other three enzymes. Three expression vectors can also be used, one for at least lycopene cyclase, and two other that each contain at least one of the other three enzyme genes. A host cell can also be transformed with four vectors; i.e., one expression vector that contains the gene encoding each one of the four named enzymes.

E. Methods for Preparing Beta-Carotene

1. Introduction

Beta-carotene can be produced by a method that includes initiating a culture, in a nutrient medium, of prokaryotic or eukaryotic host cells that provide lycopene and are transformed with a recombinant DNA molecule containing a compatible expression vector operatively linked to a before-described exogenous DNA segment that defines the structural gene for lycopene cyclase. The cell culture is maintained for a time period sufficient for the transformed cells to produce (express) lycopene cyclase, and for that expressed enzyme to convert the provided lycopene into beta-carotene. The beta-carotene can thereafter be recovered as discussed herein. In higher plants, the nutrient medium (and in many cases the substrate) is supplied by the plant itself, and the initiated culture is the germinated seed, protoplast or even a grafted explant from a prior culture.

This recombinant DNA molecule preferably contains an expression system that comprises one or more expression vectors compatible with host cells, operatively linked to an exogenous DNA segment, comprising..(i) a nucleotide base sequence corresponding to a sequence defining a structural gene for GGPP synthase, and (ii) a nucleotide base sequence corresponding to a sequence defining a structural gene for phytoene synthase, (iii) a nucleotide base sequence corresponding to the sequence defining a structural gene for phytoene dehydrogenase-4H, and (iv) a nucleotide base sequence corresponding to the sequence defining a structural gene for lycopene cyclase. The culture is maintained for a time period sufficient for the cells to express the enzymes that are encoded by the exogenous structural genes, and for those enzymes to produce GGPP, phytoene, lycopene and beta-carotene. Thus, lycopene is provided to the host cells by the enzymes expressed by the expression system.

In one particularly preferred embodiment, the structural genes for GGPP synthase, phytoene synthase, phytoene dehydrogenase-4H and lycopene cyclase are contained operatively linked in a single expression vector, preferably under the control of the same promoter. The order of expression of the structural genes is not important so, for example, the structural gene for GGPP synthase can be located 5' (upstream) from the structural gene for phytoene synthase, or vice versa. In another preferred embodiment, two expression vectors are used, with the structural genes for GGPP synthase, phytoene synthase and phytoene dehydrogenase-4H on one vector and the structural gene for lycopene cyclase on the other vector. In yet another preferred embodiment, three expression vectors are used. Yeast and plants require a separate promoter for each gene, although the same promoter can be used for each gene.

Example 18 illustrates beta-carotene production in E. coli host cells using a single expression vector pARC376-Pst 102 containing all four genes. Similarly, the very active GGPP synthase gene contained in pARC489D, phytoene synthase gene contained in pARC140N and the phytoene dehydrogenase-4H structural gene found in pARC496A can be transformed separately or together with the lycopene cyclase structural gene found in pARC1510 to prepare transformed host E. coli cells that contain all four functional structural genes. Here, expression of plasmids pARC489D, pARC140N and pARC496A provides the enzymes needed to convert ubiquitous cellular precursors into the required phytoene that is converted into lycopene that is subsequently converted into beta-carotene by the action of the lycopene cyclase expressed by plasmid pARC1510. Likewise, Example 19 illustrates beta-carotene production in S. cerevisiae host cells transformed with plasmid pARC145G, whose expression products provide phytoene to the cells, and plasmid pARC1520 that expresses both phytoene dehydrogenase-4H that converts the provided phytoene into lycopene, and lycopene cyclase that converts lycopene into beta-carotene.

This method also contemplates use of transformed host cells containing only a lycopene cyclase-containing expression vector. Here, the nutrient medium supplies the lycopene to the host cells so that those host cells can provide lycopene as the precursor for the expressed lycopene cyclase. The nutrient medium can contain the requisite amount of lycopene in micelles or vesicles, as are well known, which are taken up by the host cells.

Another aspect of this method contemplates host cells transformed with one, two or three expression vectors for the production of phytoene synthase, phytoene dehydrogenase-4H, and lycopene cyclase. Here, GGPP is provided to the transformed host cells via the nutrient medium as above, and the transformed host cells convert the GGPP to the necessary phytoene and then to lycopene using the transformed structural genes.

In higher plants, the transformed elements are so manipulated as to permit them to mature into soil-or otherwise-cultivated plants, such as plants that are cultivated hydroponically or in other soil-free media such as lava rock, crushed coral, sphagnum moss and the like.

Methods not utilizing tissue culture procedures are also contemplated, for example, using Agrobacterium-mediated vectors to produce transgenic plants from seeds.

F. Examples

The following examples are intended to illustrate, but not limit, the scope of the invention. Studies related to carotenoid biosynthesis generally, GGPP synthase and phytoene synthase are discussed in Examples 1–9, studies related to lycopene are discussed in Examples 10–16, and studies related to beta-carotene are discussed in Examples 17 through 22.

All recombinant DNA techniques were performed according to standard protocols as described in Maniatis et al., *Molecular Cloning, A Laboratory Manual*, Cold Spring Harbor Laboratory, Cold Spring Harbor, N.Y. (1982), except where noted. All restriction enzymes and other enzymes were used according to the supplier's instructions. DNA sequencing was performed on M13 single-stranded DNA using a modification of the basic dideoxy method of Sanger et al, *Proc. Natl. Acad. Sci. U.S.A.* 74:5463-7 (1977). A sequencing kit from BRL Life Technologies, Inc., Gaithersburg, M.D. was used. The DNA sequence was analyzed on the IG Suite from Intelligenetics Corp.

Enzyme assays for enzymes engineered in E. coli or Saccharomyces cerevisiae were performed according to the protocols provided in Example 2j for GGPP synthase and phytoene synthase, in Example 10g for phytoene dehydrogenase-4H, and in Example 17f for lycopene cyclase.

Carotenoids were extracted and analyzed by high performance liquid chromatography (HPLC) from both *E. coli* or *S. cerevisiae* according to the protocol provided in Example 5. The identity of zeaxanthin diglucoside was confirmed by mass spectroscopy performed according to the protocol provided in Example 5. The identity of zeaxanthin was confirmed by mass spectroscopy. The identification of the other carotenoids was confirmed by elution from HPLC, UV-Visible spectral analysis, and comparison with known standards of phytoene, lycopene, and beta-carotene.

The method for production in *E. coli* of the proteins in *E. coli* encoded by the different genes, using the inducible Rec 7 promoter system in the plasmid pARC306A, is described in Example 2i. These proteins were used in the enzyme assays described. This protocol was also used to produce sufficient amounts of the proteins from which the N-terminus of the protein was determined.

Two different approaches for inducing beta-carotene production in *E. coli* are described illustratively in Example 18. In the first, plasmids are constructed that contain collectively the GGPP synthase gene, the phytoene synthase gene, the phytoene dehydrogenase-4H gene and the lycopene cyclase gene. Under the control of proper transcription and translation regulatory sequences, these genes produce active enzymes. In this method, the genes for GGPP synthase, phytoene synthase, phytoene dehydrogenase-4H, and lycopene cyclase need to be identified, engineered to place the transcription and translation regulatory sequences adjacent to the genes, and then introduced into a plasmid sequence.

In the second approach, beta-carotene is produced in cells transformed with the pARC376 plasmid where the gene for beta-carotene hydroxylase, which catalyzes the conversion of beta-carotene to zeaxanthin, is mutated, deleted, or in any other way made non-functional. This approach utilizes an altered pARC376 plasmid so that the transformed cells accumulate beta-carotene.

Example 1. Confirmation of the presence of the carotenoid biosynthesis pathway genes in *Erwinia herbicola* plasmid pARC376 a. *E. coli*

*E. coli* cells, which by themselves are not capable of pigment formation, become intensely yellow in color when transformed with plasmid pARC376 (FIG. 5). The pigments responsible for the observed yellow color were extracted from the cells and shown to be zeaxanthin and zeaxanthin diglucosides from UV-VIS spectral and mass spectral data.

In the presence of diphenylamine in the growth medium, pigment formation is strongly inhibited resulting in colorless cells, which have been found to accumulate trace amounts of phytoene. Diphenylamine is known to inhibit the phytoene dehydrogenase-4H reaction. This was the first indication that the carotenoid pathway is functional in these transformed cells. Harvesting mid-log phase cells and extracting carotenoids from those cells indicated the presence of phytoene, phytofluene, and zeta-carotene, further confirming the presence of functional carotenoid pathway syntheses in the cells.

b. *A. tumefaciens*

Carotenoid production in *A. tumefaciens* containing the *Erwinia herbicola* carotenoid DNA was investigated. Three plasmids containing various portions of plasmid pARC376 were transformed into *A. tumefaciens* strain LBA4404. Four different carotenoids were produced, i.e., phytoene, lycopene, beta-carotene, and zeaxanthin.

The three plasmids used in this study were:

1. Plasmid pARC803 (about 17 kb), which contained the R1162 ori, the kanamycin resistance gene (NPTII) and the *Erwinia herbicola* DNA of plasmid pARC376-Ava 103 fragment (derived by deleting 2 Ava I restriction fragments, at about 8231-8842-10453, and cloning the Hind III (about 13463) to Eco RI (about 3370 FIG. 5) fragment into plasmid pSOC925 (FIG. 12);

2. Plasmid pARC274 (about 17 kb), which contained the R1162 ori, the kanamycin resistance gene, and the *Erwinia herbicola* DNA of plasmid pARC376-Bam 100 fragment (derived by deleting 2 Bam HI restriction fragments, at about 3442-4487-5302 and cloning the Hind III (about 13463) to Eco RI (about 3370, FIG. 5) fragment into plasmid pSOC925;

3. Plasmid pARC288 (about 18 kb) which contained the R1162 ori, the kanamycin resistance gene, the *Erwinia herbicola* DNA of plasmid pARC376-Sal 8 (Example 2a) and the GGPP synthase gene fragment from Hind III (about 13463) to Eco RV (about 11196, FIG. 5).

These plasmids were transformed into competent cells of *Agrobacterium* according to the protocol below.

1. An Agrobacterium colony was grown overnight (about 15 hours) in 2 to 3 ml YP medium (10 g/l Bactopeptone, 10 g/l yeast extracts, and 5 g/l NaCl, pH 7).
2. The overnight culture was transferred into 50 ml fresh YP medium in 250 ml flask at 250 rpm and 28° C., and grown until the culture reached 0.5 to 1.0 OD ($A_{600}$).
3. The culture was chilled on ice for 5 minutes, then the cells were harvested by centrifugation.
4. The cells were resuspended in 1 ml of 20 mM calcium chloride.
5. About 1 μg of plasmid DNA was added into 0.1 ml of the cell suspension and mixture was incubated on ice for 30 minutes.
6. The reaction mixture was frozen in liquid nitrogen for 1 to 2 minutes and then incubated at 37° C. for 5 minutes.
7. One ml of YP medium was added and the mixture was incubated at 28° C. for 2 to 4 hours.
8. The cells were plated in LB medium (5 g/l yeast extracts, 10 g/l tryptone, 5 g/l NaCl, and 2 g/l glucose, pH 7) containing 50 μg/ml kanamycin.

The transformed cells were selected on LB plates containing 50 μg/ml of kanamycin at 28° C. (LB plates=10 g/l tryptone, 5 g/l yeast extracts, 5 g/l NaCl, 2 g/l glucose, and 15 g/l Bactoagar). The transformed cells were cultivated on the same rich medium for two days, harvested and dried for carotenoid extraction. For carotenoid extraction, 0.5 ml of water, 2.5 ml of acetone, and 2.5 ml of methanol were added to the dried cells. After 1 hour incubation with mixing at room temperature, the solvent containing carotenoids was filtered, and carotenoids isolated were analyzed by HPLC.

The carotenoids produced by both *E. coli* and *Agrobacterium* are listed in Table 1. The amounts of carotenoids produced by *Agrobacterium* were about 5 to 10 times lower than by *E. coli* cells carrying the same plasmids (by gross estimation).

TABLE 1

Carotenoids Produced by A. tumefaciens LBA4404

| Plasmids | Major Carotenoids | |
|---|---|---|
| | E. coli | Agrobacterium |
| pARC803 | Lycopene | Lycopene, Phytoene |
| pARC274 | β-Carotene | β-Carotene, (Phytoene)* |
| pARC288 | Zeaxanthin | Zeaxanthin |

*Minor component.

The origin of replication from plasmid R1162, described by Meyer, R. et al., J. Bacteriol. 152:140 (1982), was introduced into plasmid pARC376, to construct a broad host-range plasmid capable of replication in other bacteria. The resulting plasmid was used to introduce Erwinia herbicola carotenoid DNA into Rhodobacter sphaeroides and its carotenoid mutants. The results demonstrated that the Erwinia herbicola carotenoid DNA was not expressed in Rhodobacter cells, presumably because there was no complementation of the Rhodobacter phytoene synthase, phytoene dehydrogenase-4H and neurosporene dehydrogenase mutants. A further study, described hereinafter, indicated that phytoene dehydrogenase-4H could be expressed in Rhodobacter cells as hosts.

Example 2. GGPP Synthase Gene

The GGPP synthase gene was obtained from the pARC376 plasmid utilizing the following methods.

a. Digestion of Plasmid pARC376 with Sal I

The plasmid pARC376-Sal 8 is a derivative of plasmid pARC376 from which two Sal I fragments were removed. One of those fragments is the approximately 1092 bp fragment bounded by the Sal I restriction sites at about 9340 and about 10432 shown in FIG. 5, whereas the other is the 3831 bp (approximate size) fragment bounded by the Sal I restriction sites at about 10432 and about 14263 also in FIG. 5. This was accomplished as follows.

Plasmid pARC376 DNA was prepared using the alkaline lysis method. 5 Micrograms of plasmid DNA were digested with Sal I (BRL) in a high salt buffer provided by the supplier and additionally containing 150 mM NaCl, for 1 hour at 37° C. and purified on a 0.8 percent agarose gel. The remaining plasmid, about 10.2 kilobases in length, was electroeluted from the gel, phenol extracted and ethanol precipitated. After elimination of the above Sal I fragments from about positions 9340 to 14263, the remaining DNA was religated to itself to form plasmid pARC376-Sal 8.

b. Construction of Plasmid pARC808

To determine if the gene for GGPP synthase was present on the deleted Erwinia herbicola DNA, plasmid pARC376-Sal 8 was cloned into plasmid pSOC925, an E. coli plasmid R1162 derivative, to generate plasmid pARC808. The plasmid pSOC925 contains the origin of replication from the R1162 plasmid, the NPT II gene from Tn5 that confers resistance to kanamycin, and unique Hind III and Eco RI restriction sites.

Briefly, the plasmid pSOC925 expression DNA vector was prepared for cloning by admixing 5 µg of plasmid DNA to a solution containing 5 units of each of the restriction endonucleases Hind III and Eco RI and the Medium Salt Buffer from Maniatis. This solution was maintained at 37° C. for 2 hours. The solution was heated at 65° C. to inactivate the restriction endonucleases. The DNA was purified by extracting the solution with a mixture of phenol and chloroform followed by ethanol precipitation.

Plasmid pARC376-Sal 8 was digested with Hind III and Eco RI in a similar way. The Erwinia herbicola DNA in plasmid pARC376-Sal 8 from the Hind III site at about position 348 to the Eco RI site at about position 3370 (FIG. 5) was then ligated into the plasmid vector pSOC925 that had already been digested with Hind III and Eco RI.

The ligation reaction contained about 0.1 µg of the plasmid pSOC925 and about 0.2 µg of the Erwinia herbicola Hind III to Eco RI fragment from plasmid pARC376-Sal 8 in a volume of 18 µl. Two µl of 10 X ligation buffer (IBI, Corp.) and 2 units of T4 ligase were added. The ligation reaction was incubated at 4° C. overnight (about 15 hours). The ligated DNA was transformed into E. coli HB 101 according to standard procedures (Maniatis). This generated the plasmid pARC808, which also codes for kanamycin resistance. The excised DNA fragment from plasmid pARC376-Sal 8 contains an endogenous promoter sequence upstream from the GGPP synthase gene.

Positive clones with inserts were identified by growing prospective positive clones, isolating plasmid DNA by the alkali lysis method (Maniatis), and performing restriction enzyme analysis on the isolated plasmid DNA's. E. coli cells transformed with this plasmid DNA did not produce colored carotenoids, as determined by visual inspection and HPLC and TLC analysis. Other studies discussed hereinafter demonstrated that plasmid pARC808 expresses Erwinia herbicola enzymes that can convert phytoene into colored carotenoid pigments.

c. Construction of Plasmid pARC282

A second plasmid was constructed by inserting a restriction fragment containing the approximately 1153 bp Bgl II (about position 12349, FIG. 5). to Eco RV (about position 11196, FIG. 5) fragment from plasmid pARC376 into the Bam HI and Hind III sites of plasmid pBR322 to produce plasmid pARC282. Briefly, the plasmid pARC273 contains the Erwinia herbicola DNA from the Bgl II site (at about position 12349) to the Eco RV site (at about position 11196).

About 100 non-coding bp downstream from the Eco RV site in plasmid pARC273 is a Hind III restriction site, which is a part of the plasmid pARC273 vector. Here, about 5 µg of the plasmid pARC273 were incubated with 5 units of each of the restriction enzymes Bgl II and Hind III in the Medium Salt Buffer (Maniatis) for 2 hours at 37° C. Five µg of the vector pBR322 were incubated with 5 units of each of the restriction enzymes Bam HI and Hind III in the Medium Salt Buffer (Maniatis) for 2 hours at 37° C.

The Erwinia herbicola Bgl II to Hind III DNA fragment (about 0.2 mg) from plasmid pARC273 was admixed with the Bam HI and Hind III digested plasmid pBR322 vector (about 0.1 µg). in 18 µl total volume. Two µl of 10X Ligation Buffer (IBI, Corp.) and 2 units of T4 Ligase were added, the reaction was incubated overnight (about 15 hours) at 4° C., and the ligated DNA was transformed into, competent E. coli HB101 cells according to procedures in Maniatis. Positive clones were identified by growing the prospective transformants, isolating plasmid DNA by the alkali lysis method (Maniatis), and performing restriction enzyme analysis on the plasmid DNA.

This plasmid, pARC282, encodes ampicillin resistance in E. coli and includes a native Erwinia herbicola promoter between the Bgl II site and the initial Met codon of the GGPP synthase gene, but does not cause any carotenoids to be produced. However, when this plasmid was transferred into *E. coli* cells containing the plasmid pARC808, and the *E. coli* cells were grown in the presence of both kanamycin and ampicillin, carotenoids were synthesized as evidenced by production of the yellow pigment zeaxanthin. Thus, plasmid pARC282 contained the essential gene that was deleted from the pARC376-Sal 8 plasmid, and the presence of this gene in combination with other *Erwinia berbicola* carotenoid genes could restore carotenoid production in *E. coli*.

d. Other Plasmid Constructs

Enzyme assays were performed on similar plasmid constructs, including plasmid pARC491 which was constructed by cloning the approximately 1068 bp fragment from Hpa I (at about position 12264 of plasmid pARC376 or about position 84 of FIG. 2) to Eco RV (at about position 11196, FIG. 5) into a plasmid denominated pARC306A. Plasmid pARC306A, whose restriction map is illustrated in FIG. 6 contains approximately 2519 base pairs. This plasmid contains the polylinker region from pUC1S, a unique Nco I site, the ampicillin selectable marker, the pMB1 origin of replication and the Rec 7 promoter. Cells containing this plasmid construct had a level of 7.91 nmol/min/mg protein activity of GGPP synthase.

e. DNA sequencing

The accuracy of some of the cloning steps was confirmed by sequencing the insert using the dideoxy method described by Sanger et al., *Proc. Natl. Acad. Sci. USA*, 74:5463–5467, (1977) and following the manufacturer's instructions included in a sequencing kit from BRL.

The DNA sequence was determined for the approximately 1153 base pair restriction fragment from the region between the Bgl II site at about 12349 of FIG. 5 and the Eco RV site at about 11196 of FIG. 5. The obtained DNA sequence and deduced partial amino acid residue sequences are shown in FIG. 2. The direction of transcription of the gene for GGPP synthase in pARC376 (FIG. 5) is counterclockwise and proceeds in the direction from the Bgl II site toward the Eco RV site.

f. In Vitro Mutagenesis

The initiation codon for GGPP synthase begins at about nucleotide position 12226 of plasmid pARC376 with the ATG codon for methionine (about position 124 of FIG. 2). A Nco I restriction site was introduced at this position of the GGPP synthase gene using in vitro mutagenesis following the techniques described in *Current Protocols In Molecular Biology*, Ausabel et al. eds., John Wiley & Sons, New York, (1987) p. 8.1.1–8.1.6, with the exception that *E. coli* CJ 236 was grown (in step 3 at page 8.1.1) in further presence of 20 μg/μl chloramphenicol. The primer used was:

```
5'                                              3'
TCA GCG GGT AAC CTT GCC ATG GGG AGT GGC AGT AAA GCG
              Nco I site        (SEQ ID NO:16)
```

The mutations were confirmed either by DNA sequencing or by the presence of the newly introduced Nco I site. This manipulation changed the natural sequence TTG CAATGG TGA (SEQ ID NO:17) to
TTG CCATGG GGA (SEQ ID NO:18), wherein a bold-faced letter above and in the following examples indicates an altered base.

This modified version of the GGPP synthase gene from the newly introduced Nco I site to the Eco RV site (about 1029 bp) was then inserted into the plasmid pARC306A to generate plasmid pARC417BH. This plasmid, pARC417BH, contains the *E. coli* promoter Rec 7 adjacent to a multiple cloning site. Structural genes lacking a promoter region, when introduced adjacent to the Rec 7 promoter, are expressed in *E. coli*.

When plasmid pARC417BH was introduced into *E. coli* cells, GGPP synthase enzyme activity (measured as GGOH) was found at the level of 6.35 nmol/min/mg protein. In addition, when plasmid pARC417BH was introduced into *E. coli* cells containing plasmid pARC808, carotenoids were produced. This demonstrated that the gene for GGPP synthase had been identified and genetically engineered.

g. Fine tuning the GGPP synthase gene

Several constructs designed to express the GGPP synthase gene were made to optimize the expression of an active GGPP synthase enzyme. Again using in vitro mutagenesis according to methods previously cited, a Nco I site was introduced at about position 12264 of plasmid pARC376 17 amino acids downstream from the initiation codon for the GGPP synthase gene that is located at about position 124 in FIG. 2. The primer used was:

```
5'                                              3'
CAT GGC GAA ATA GAA GCC ATG GGA CAA TCC ATT GAC GAT
                    Nco I site        (SEQ ID NO:19)
```

That site was thus placed at the upstream side of the Met whose ATG codon begins at about position 175 of the sequence of FIG. 2. The natural DNA sequence AAG TAATGA GAC (SEQ ID NO:20) was changed to
AAG CCATGG GAC (SEQ ID NO:21).

This modified GGPP synthase gene coding for seventeen fewer amino-terminal amino acid residues was inserted into plasmid pARC306A at the Nco I site of that plasmid to generate plasmid pARC418BH.

When GGPP synthase assays were performed on cells transformed with plasmid pARC418BH, no enzyme activity was detected. In addition, when this modified GGPP synthase was added to *E. coli* cells containing the plasmid having the rest of the genes for the enzymes required for carotenoid synthesis, plasmid pARC808 described above, no carotenoids were synthesized. This demonstrated that deletion of the 17N-terminal amino acids of the GGPP synthase resulted in a non-functional enzyme.

Plasmid pARC306A was digested with Eco RI. The Eco RI ends were converted to blunt ends using the Klenow fragment of DNA Pol I according to the usual techniques described by Maniatis. The GGPP synthase gene was cleaved with Nru I and Sac I to provide a Nru I-Sac I restriction fragment that extended from about position 12187 to about position 11776 of FIG. 5. After further digestion of the cleaved, blunt-ended plasmid pARC306A with Sac I, the Nru I-Sac I fragment was ligated therein to form plasmid pARC488A.

Plasmid pARC282 was digested with Sac I and Hind III, and the Sac I-Hind III fragment was isolated. Plasmid pARC488A was digested with Sac I and Hind III, and the Sac I-Hind III fragment from pARC282 was ligated therein to form plasmid pARC489B. The above digestions and blunt end formation removed the polylinker region shown in FIG. 6 from the Eco RI site to the Hind III site.

Positive clones were identified by plasmid DNA isolation (Maniatis), and by restriction enzyme analysis on the plasmid DNA.

In plasmid pARC489B, DNA coding for the first 13 amino acid residues of the GGPP gene was deleted. The first four amino acid residues encoded downstream from the Rec 7 promoter in plasmid pARC306A and the newly generated Eco RI blunt end were placed upstream from the former Nru I site of GGPP synthase. This altered the N-terminal amino acid sequence of GGPP synthase in the following manner. The difference in amino acid sequence became:

Original Amino Acid Sequence of Native *Erwinia Herbicola* GGPP Synthase.

MET VAL SER GLY SER LYS ALA GLY VAL SER PRO HIS ARG
GLU ILE ...
(SEQ ID NO:22)

Amino Acid Sequence of modified GGPP Synthase Gene in plasmid pARC489B

MET ALA GLU PHE GLU ILE ...
(SEQ ID NO:23)

in which altered bases are shown in bold face. The DNA sequence for this heterologous gene is illustrated in FIG. 3, with the coding region beginning at about position 150 and extending through to about position 1153.

*E. coli* cells transformed with the plasmid pARC489B were assayed for GGPP' synthase activity. The level of activity was found to be 12.15 nmol/min/mg protein.

When the plasmid pARC489B was transferred to *E. coli* cells that contained a plasmid containing the rest of the genes coding for enzymes required for carotenoid production, plasmid pARC808, the cells produced carotenoids. Therefore, this construction coded for an active enzyme even though the heterologous gene portion from plasmid pARC306A encoded the first four amino acid residues, and the first 13 amino acid residues encoded by the gene for GGPP synthase were deleted.

The above described DNA segment of plasmid pARC489B overlaps bases encoding four amino acids adjacent to the Rec 7 promoter at its 5' end and extends to the blunted, former Eco RI site in the polylinker region of the plasmid. This DNA segment can be excised by reaction with Nco I at its 5' end and the Hind III or Pvu II sites as are illustrated for plasmid pARC306A in FIG. 6.

The desired GGPP synthase gene does not contain a Pvu II or a Hind III restriction site. The region between the Hind III and Pvu II sites of plasmid pARC489B contains stop codons in all three reading frames. It is preferred to utilize the Pvu II site for cleavage of the 3' end of the DNA. Thus, the desired GGPP synthase DNA segment can be referred to as lying within the approximately 1150 bp sequence between the Nco I and Pvu II restriction sites of plasmid pARC489B.

Next, the 3' end of the gene for GGPP synthase was modified. This construction was made in the following manner.

Plasmid pARC489B was digested with Bal I and Hind III. (This Bal I site is at about position 11347 of FIG. 5.) The Hind III' site of the resulting large restriction fragment was filled in using the Klenow fragment of DNA polymerase 1. The resulting double blunt ended fragment was religated together to form plasmid pARC489D.

The GGPP synthase gene-containing portion of the resulting plasmid pARC489D has the same 5' end as does plasmid pARC489B, but the 3' end is about 151 bp shorter than the GGPP synthase gene in plasmid pARC489B. The sequence of the heterologous GGPP synthase structural gene of plasmid pARC489D is illustrated in FIG. 3 from about position 150 to about position 1002, with the 5' end of this DNA being the same as that of the GGPP synthase gene present in plasmid pARC489B.

Downstream about 70 bp from the Hind III site of the multiple cloning region in plasmid pARC306A is a Pvu II site. There are no Pvu II sites in the GGPP synthase gene. Therefore, the GGPP synthase structural gene can be transferred from a pARC306A-derived plasmid such as plasmid pARC489D to other plasmids as an approximately 1000 bp Nco I-Pvu II fragment.

Plasmid pARC489D was transformed into *E. coli*. Very surprisingly, this construction gave the highest enzyme activity of all the different versions of the GGPP synthase gene. This activity was an unexpectedly high 23.28 nmol/min/mg protein.

When the plasmid pARC489D was introduced into *E. coli* cells containing the plasmid pARC808, carotenoids were synthesized.

A comparison of the activities of several of the previously described GGPP synthase gene constructs is shown in Table 2 below, including the activity of a related gene present inherently in *R. sphaeroides* 2.4.1. Those results indicate an enhancement of about 35 to about 130 times the activity of the original plasmid pARC376.

TABLE 2

GGPP Synthase Activity of Various Gene Constructs As Compared to *R. sphaeroides*

| Constructs | Activity (nmol/min/mg protein) |
| --- | --- |
| *R. sphaeroides* 2.4.1 | 0.20 |
| pARC376 | 0.18 |
| pARC491 | 7.91 |
| pARC417BH | 6.35 |
| pARC418BH | 0 |
| pARC489B | 12.15 |
| pARC489D | 23.28 | h. GGPP synthase characterization

The plasmids pARC489B and pARC489D were introduced into the *E. coli* strain JM101 (BRL). These cells were treated with nalidixic acid to induce the Rec 7 promoter, which caused production of large amounts of the GGPP synthase enzyme. The protein extract from these cells was separated on SDS-polyacrylamide gel electrophoresis (PAGE). Because of the very large amount of GGPP synthase produced under these conditions, it is readily identifiable by staining with Coomassie Brilliant Blue on the SDS-PAGE system. The isolated and substantially purified GGPP synthase can then be recovered from the gels by standard procedures.

The *Erwinia herbicola* GGPP synthase that was produced in cells containing plasmid pARC489B was a protein of the size of about 35 kilodaltons, and is thought to be the complete, native molecule, whereas the GGPP synthase that was produced in cells with plasmid pARC489D was about 33 kilodaltons. Thus, the 5' deletion of thirteen amino acid residues and then replacement with non-*Erwinia herbicola* sequence of four residues, coupled with the 3' deletion of the approximately 151 bp between the Bal I site and the Eco RV site produced a protein that was about 2 kilodaltons smaller, but far more active than the native molecule. The GGPP synthase structural gene present in plasmid pARC489D is the gene most preferably used for GGPP synthase in *E. coli*, *S. cerevisiae*, and higher plants.

i. Induction of Rec 7 driven protein production

The previously discussed production of GGPP synthase in *E. coli* using plasmids pARC417BH, pARC489B and pARC489D was carried out using the Rec 7 promoter. Phytoene synthase production in *E. coli* using the plasmid pARC140N discussed below was also carried out using the Rec 7 promoter. Culture conditions for growth of the transformed *E. coli* cells are as follows.

A single colony from a plate containing freshly (<2 days old) transformed cells was picked, grown overnight (e.g. about 15–18 hours) in M9+CAGM medium (see Table 3B hereinafter for media formulations) +50 µg/ml ampicillin at 30° C. Cultures of cells were grown at various temperatures from 27°–37° C. by diluting the cells 1:100 into fresh M9+CAGM medium and maintaining the culture at the desired temperature. Each culture was grown until it was roughly one-half of the final desired density (150–180 Klett units in a shaken culture). The culture was then induced by addition of nalidixic acid to a final concentration of 50 µg/ml. Five µl of a stock solution of freshly prepared 10 mg/ml nalidixic acid in 0.1N NaOH per ml of culture to be induced was used. Induction was permitted to proceed for 2–4 hours after addition of nalidixic acid.

TABLE 3

A. M9 + CAGM MEDIUM COMPOSITION

| Component | grams/liter |
|---|---|
| $Na_2HPO_4 \cdot 7H_2O$ | 13.2 |
| $KH_2PO_4$ | 3.0 |
| NaCl | 0.5 |
| $KH_4Cl$ | 1.0 |
| Casamino Acids (Difco) | 10.0 |
| $MgSO_4$ | 0.3 |
| $CaCl_2 \cdot 2H_2O$ | 0.004 |
| Glucose (Shake Flask) | 3.0 |
| Thiamine-HCl | 0.025 |
| $FeCl_3$ | 0.0054 |
| $ZnSO_4$ | 0.0004 |
| $CoCl_2$ | 0.0007 |
| $Na_2MoO_4$ | 0.0007 |
| $CuSO_4$ | 0.0008 |
| $H_3BO_3$ | 0.0002 |
| $MnSO_4$ | 0.0005 |

B. MEDIUM FORMULATIONS
M9 + CAGM Medium for Shake Flasks (1 Liter)

| | | |
|---|---|---|
| 900 ml | distilled $H_2O$ | Autoclaved |
| 40 ml | 25X M9 Salts | Autoclaved |
| 50 ml | 20% (w/v) Casamino Acids | Filtered |
| 6.4 ml | 40% (w/v) Glucose | Autoclaved |
| 1.2 ml | 1M $MgSO_4$ | Autoclaved |
| 0.25 ml | 0.1M $CaCl_2$ | Autoclaved |
| 0.25 ml | 0.1% (w/v) Thiamine-HCl | Filtered |
| 0.1 ml | 10,000X Trace Minerals | Filtered |
| 0.1 ml | 10,000X Iron Supplement | Filtered |

All components should be sterilized separately, cooled to room temperature and then combined.

TABLE 3-continued

C. 25X M9 Salts (1 liter)

| Component | grams |
|---|---|
| $Na_2HPO_4 \cdot 7H_2O$ | 330 |
| $KH_2PO_4$ | 75 |
| $NH_4Cl$ | 25 | distilled $H_2O$ to 1 Liter

D. 10,000X Trace Minerals (200 ml)

| Component | grams |
|---|---|
| $ZnSO_4$ | 0.8 |
| $CoCl_2$ | 1.4 |
| $Na_2MoO_4$ | 1.4 |
| $CuSO_4$ | 1.6 |
| $H_3BO_3$ | 0.4 |
| $MnSO_4$ | 1.0 |

Dissolve in 200 ml of $H_2O$, add 1 drop HCl (fuming), filter sterilize.

E. 10,000X Iron Supplement (200 ml)

| Component | grams |
|---|---|
| $FeCl_3$ | 10.8 |

Dissolve in 200 ml of $H_2O$, add 1 drop HCl (fuming), filter sterilize.

Each culture was highly aerated at all times. Fifteen ml in a 250 ml sidearm flask for analytical runs were routinely used, and 330 ml in a Fernbach (2.8 l) flask for semi-preparative runs were routinely used.

Production of all proteins examined so far has been quite dependent on strong aeration during the induction period.

j. Enzyme assay

GGPP synthase was prepared in the cell cytosol as described below.

(1) Cytosol preparation

The growing cells were centrifuged to form a cell pellet. The cell pellet was resuspended in 50 mM potassium phosphate buffer, pH 7.0, containing 10 percent glycerol, 0.1 mM EDTA in a 15 ml plastic conical tube and vortexed with acid washed glass beads (425–600 micron for yeast cells and 75–150 micron for bacteria are typically used) for 1 minute and allowed to cool in ice for 1 minute. This was repeated three times after which the homogenate was transferred to another tube and centrifuged at 17,000 x g for 60 minutes at 4° C. The supernatant was next centrifuged at 150,000 x g for 60 minutes at 4° C. The supernatant thus obtained was the cell cytosol.

(2) Assay for GGPP synthase

Cell cytosol was preincubated for 20 minutes at 4° C. with 10 µM epoxy-isopentenyl pyrophosphate (IPP) in order to inhibit IPP-isomerase activity. The assay mixture, containing 40 µM farnesyl pyrophosphate (FPP) and 40 µM 14C-IPP (250,000 dpm) in 10 mM Hepes buffer (pH 7.0, 1 mM $MgCl_2$, 1 mM DTT) in a 1 ml total volume of preincubated cytosol, was incubated at 37° C. for 30 minutes.

The reaction was terminated by transferring the assay mixture to a pre-cooled (in dry ice) tube and lyophilizing for 8 hours. The dry residue was resuspended in 0.5 ml of 0.1M glycine buffer (pH 10.4, 1 mM $MgCl_2$, 1 mM $ZnCl_2$) and treated with 25 units of alkaline phosphatase for 3 hours at 37° C. The alkaline phosphatase reaction converted the pyrophosphates to their corresponding alcohols, which were extracted with hexane, evaporated to dryness under a stream of nitrogen and redissolved in 150 µl of methanol.

Seventy-five μl of this methanol solution were injected into an HPLC connected with a C-18econosphere Altech analytical column (4.6×250 mm, 5 micron particle'size) equilibrated with 85 percent methanol:water (4:1) and 15 percent THF:CH$_3$CN (1:1). A linear gradient to 80 percent methanol:water (4:1) and 20 percent THF:CH$_3$CN (1:1) in 20 minutes at 1.5 ml/min resolved the alcohols. The HPLC was connected in series with a Radiomatic flow detector, which integrated the radioactive peaks, e.g. geranylgeraniol (GGOH) peak. Specific activity was expressed in nmol GGOH formed/min/mg of protein under the given assay conditions. Protein was determined by the Bradford method using BSA as the standard.

Example 3. GGPP Synthase Production in Higher Plants a. Construction of the plasmid pARC498

The most active form of the GGPP synthase gene is found on plasmid pARC489D, described above. The GGPP synthase structural gene of this plasmid was modified to introduce the restriction site Sph I at the initiation methionine codon and another Sph I site at the 3' end of the gene following the stop codons present in plasmid pARC489D.

To accomplish these modifications, an about 1,100 bp Hpa I to Pvu II fragment was excised from plasmid pARC489D. This fragment was isolated on agarose gel electrophoresis and used as the template for polymerase chain reaction (PCR). The following oligonucleotide probe was used to create the Sph I site at the ATG start codon of the GGPP synthase gene:

5' TAA <u>GCA TGC</u> TCG AAT TCG AAA TAG AAG TAA TG 3'
       Sph I                                 (SEQ ID NO:24)

in which bold-faced letters indicate altered bases.

This PCR technique changed the second residue of GGPP synthase from an alanine to a leucine.

The following oligonucleotide probe was used to create the Sph I site after the stop codon in the plasmid pARC489D following the GGPP synthase gene:

5'CCG CGC ATG <u>CGA</u> CCC TTG TGT ATC AAA CAA G 3'
        Sph I                                (SEQ ID NO:25)

The probes were resuspended in a volume of sterile water such that final concentration of each probe was 10 pmoles/μl.

The introduction of an Sph I site at the 3' end of the GGPP synthase gene changed the DNA sequence as indicated below:

Original Sequence:
5' CTT GTT TGA TAC ACA AGG GTC GCA TCT CGC G 3'
                                  (SEQ ID NO:26)

New Sequence:
5' CTT GTT TGA TAC ACA AGG GTC <u>GCA TGC</u> CGC G 3'
                                  (SEQ ID NO:27)

in which a bold-faced letter in the new sequence indicates an altered base.

b. PCR Reaction

The GeneAmp DNA Amplification Reagent Kit (Perkin Elmer Cetus) was used to perform the reaction. The following components were mixed in the quantity and order specified according to the manufacturers instructions.

| Component | Order of Addition | Volume | Final Concentration |
|---|---|---|---|
| Sterile Water | 1 | 43.5 μl | |
| 10 X Rxn. Buffer | 2 | 10 μl | 1 X |
| 1.25 mM dNTP Mix | 3 | 16 μl | 200 μM each |
| Primer 1 (10 pMole/μl) | 4 | 10 μl | 1 μM |
| Primer 2 (10 pMole/μl) | 5 | 10 μl | 1 μM |
| Template DNA | 6 | 10 μl | 100 ng |
| Taq Polymerase | 7 | 0.5 μl | 2.5 Units |

Mineral oil (100 μl) was layered on top of the reaction mixture, and the reaction was performed using the Perkin Elmer Cetus DNA Thermal Cycler (Perkin Elmer, Prairie Cloud, Minn.). The method consisted of 25 cycles of amplification. One cycle included the following:
1) 1 minute denaturation at 92° C.;
2) 2 minute template priming at 37° C.;
3) 3 minute polymerization at 72° C.;

At the end of 25 cycles, one final 7 minute polymerization at 72° C. was carried out.

After the reaction was completed the mineral oil was removed, the reaction mixture was extracted twice with ether, and the DNA was precipitated with ethanol.

c. Cloning of the PCR produced DMA fragment.

The DNA produced by the PCR reaction was digested with Sph I. This about 936 bp Sph I PCR-generated fragment was isolated and recovered from an agarose gel, and cloned into the unique Sph I site of plasmid pUC18 (Pharmacia Piscataway, N.J.). This resulting plasmid was named pARC498.

d. Proof of Functional Genetically Engineered GGPP Synthase Gene

The proper functioning of the GGPP synthase gene of plasmid pARC498 was tested by cloning the PCR modified gene into an E. Coli expression vector. This was done by first digesting plasmid pARC498 with Hind III and Sma I, these sites being on either side of the Sph I site. The resulting Hind III-Sma I fragment was isolated and recovered from an agarose gel, and treated with the Klenow fragment of DNA Polymerase I to create blunt ends. This blunt ended fragment was then cloned into plasmid pKK223-3 (Pharmacia, Piscataway, N.J.), as follows.

Plasmid pKK223-3 contains the TAC promoter active in E. coli. Plasmid pKK223-3 was digested with Hind III and similarly treated with the Klenow fragment to form blunt ends. The Hind III-Sma I blunt ended fragment, excised from plasmid pARC498, was ligated to the blunt ended plasmid pKK223-3. The resulting plasmid was named pARC1504.

When plasmid pARC1504 was introduced into E. coli cells containing plasmid pARC808, carotenoids were produced. This demonstrated that the modified GGPP synthase gene encoded a functional GGPP synthase enzyme.

e. Construction of plasmid pATC225

The PCR modified GGPP synthase structural gene was removed as an Sph I fragment from plasmid pARC498. This Sph I fragment was cloned into the Sph I site of plasmid pATC212, which construction is discussed below. The resulting plasmid was named pATC216. This plasmid contains a GGPP synthase gene construct with a CaMV 35S plant promoter and transit peptide sequence at the 5' end of the gene, and a NOS polyadenylatien sequence at the 3' end.

This GGPP synthase gene construct was inserted into the plasmid pGA482 (Pharmacia) in convenient restriction sites within the multiple cloning linker region to form plasmid pATC225. The relevant features of plasmid pGA482 include (i) an origin of replication that permits maintenance of the plasmid in *Agrobacterium tumefaciens*, (ii) the left and right border sequences from the T-DNA region that direct the integration of the DNA segment between the borders into the plant genome, and (iii) the NOS promoter adjacent to the kanamycin resistance gene that permits plant cells to survive in the presence of kanamycin.

This GGPP synthase gene construct was transformed into *Agrobacterium tumefaciens* LBA4404 (Clontech, Inc.) according to standard protocols. *Agrobacterium* cells containing the plasmid with the GGPP synthase gene construct were transferred by infection of tobacco leaf discs using the method of Horsch et al., *Science*, 227:1229–1231 (1985). During the infection process, the entire DNA segment between the left and right borders of the pGA482 plasmid is transfected into the plant cells. Transfected plant cells are selected for kanamycin resistance.

Western blots of extracts from transfected plant chloroplasts showed the presence of GGPP synthase. No enhancement of carotenoid production was observed.

The specific DNA segments, recombinant molecules and techniques utilized in the preparation of the above tobacco plants are discussed below.

i. Transit Peptide

The sequence of the transit peptide DNA is basically that of Mazur et al., *Nucl. Acids Res.*, 13:2343–2386 (1985) for the ribulose bis-phosphate carboxylase-oxygenase signal peptide of *Nicotiana tabacum*. Two changes were made to the disclosed 177 bp sequence.

In the first change, two cytidine residues were added at the 5' end to create a Nco I restriction site. The second change introduced an Nar I site that cleaves between bases at positive 73 and 74. This change was a G for T replacement at position 69 and a G for A replacement at position 72, both of which changes left the encoded amino acid residue sequence unchanged. The final two residues at the 3' end were deleted to provide the natural Sph I restriction site sticky end.

The synthetic transit peptide-encoding DNA also therefore contained 177 bp. The complete double stranded sequence, showing the 5' Nco I and 3' Sph I sticky ends, is illustrated in FIG. 17.

The DNA encoding the transit peptide was synthesized synthetically from eight fragments that were annealed together in pairs by heating at 90 degrees C. for five minutes and then slowly cooling to room temperature. Fifty picomoles of each fragment were utilized.

Those eight fragments were:

```
1.  5'  CAT GGC TTC CTC AGT TCT TTC CTC TGC AGC AGT
            TGC C 3'                    (SEQ ID NO:28)

2.  5'  GGG TGG CAA CTG CTG CAG AGG AAA GAA CTG AGG
            AAG C 3'                    (SEQ ID NO:29)

3.  5'  ACC CGC AGC AAT GTT GCT CAA GCT AAC ATG
            GTG G 3'                    (SEQ ID NO:30)

4.  5'  CGC CAC CAT GTT AGC TTG AGC AAC ATT GCT GC  3'
                                        (SEQ ID NO:31)

5.  5'  CGC CTT TCA CTG GCC TTA AGT CAG CTG CCT CAT
            TCC CTG TTT CAA GGA AG 3'   (SEQ ID NO:32)

6.  5'  TTT GCT TCC TTG AAA CAG GGA ATG AGG CAG CGA
            ATG AGG CAG CTG ACT TAA GGC CAG TCA AAG G 3'
                                        (SEQ ID NO:33)

7.  5'  CAA AAC CTT GAC ATC ACT TCC ATT GCC AGC AAC
            GGC GGA AGA GTG CAA TGC ATG 3'.
                                        (SEQ ID NO:34)

8.  5'  CAT TGC ACT CTT CCG CCG TTG CTG GCA ATG GAA
            GTG ATC TCA AGG T 3'        (SEQ ID NO:35)
```

The pairs utilized for annealing were 1 and 2, 3 and 4, 5 and 6, and 7 and 8 to form sticky ended annealed pairs 1–2, 3–4, 5–6 and 7–8 that are shown below.

```
1-2                                            (SEQ ID NO:28)
5'  CATGGCTTCCTCAGTTCTTTCCTCTGCAGCAGTTGCC  3'
         3' CGAAGGAGTCAAGAAAGGAGACGTCGTCAACGGTGGG 5'
                                               (SEQ ID NO:29)

3-4                                            (SEQ ID NO:30)
5'  ACCCGCAGCAATGTTGCTCAAGCTAACATGGTGG 3'
         3' CGTCGTTACAACGAGTTCGATTGTACCACCGC 5'
                                               (SEQ ID NO:31)
```

5-6
```
5'  CGCCTTTCACTGGCCTTAAGTCAGCTGCCTCATTCCCTGTTTCA
   3'  GGAAAGTGACCGGAATTCAGTCGACGGAGTAAGGGACAAAGT

AGGAAG    3'      (SEQ ID NO:32)
       TCCTTCGTTT 5'     (SEQ ID NO:33)
```

7-8
```
5'  CAAAACCTTGACATCACTTCCATTGCCAGCAACGGCGGAAGAGT
      3'  TGGAACTGTAGTGAAGGTAACGGTCGTTGCCGCCTTCTCA

GCAATGCATG 3'     (SEQ ID NO:34)
       CGTTAC     5'     (SEQ ID NO:35)
```

Fragment 1-2 was ligated with fragment 3-4 to form fragment 1-4 whose sequence is shown below.

```
5'  CATGGCTTCCTCAGTTCTTTCCTCTGCAGCAGTTGCCACCCGCAGCAA
      3'  CGAAGGAGTCAAGAAGGAGACGTCGTCAACGGTGGGCGTCGTT

TGTTGCTCAAGCTAACATGGTGG 3'   (SEQ ID NO:36)
       ACAACGAGTTCGATTGTACCACCGC 5' (SEQ ID NO:37)
```

Fragment 5-6 was ligated with fragment 7-8 to form fragment 5-8 whose sequence is shown below.

```
5'  CGCCTTTCACTGGCCTTAAGTCAGCTGCCTCATTCCCTGTTTCAAGGA
      3'  GGAAAGTGACCGGAATTCAGTCGACGGAGTAAGGGACAAAGTTCCT

AGCAAAACCTTGACATCACTTCCATTGCCAGCAACGGCGGAAG
       TCGTTTTGGAACTGTAGTGAAGGTAACGGTCGTTGCCGCCTTC

AGTGCAATGCATG    3'     (SEQ ID NO:38)
       5'TCACGTTAC             (SEQ ID NO:39)
```

The 1-2 and 3-4 pairs (fragments 1-4) were ligated together over a two hour time period, as were pairs 5-6 and 7-8 to form two double-stranded sequences. The ligation product of fragments 1-4 was digested with Nco I and Nar I, whereas the product of fragments 5-8 was digested with Nar I and Sph I. These digestions separated any concatamers formed during ligation and provided the necessary sticky ends for further ligation.

The digested mixes were run on 6 percent acrylamide gels. The bands of correct size were excised from the gels, and the DNA was eluted from the gel matrix.

The DNA fragments of (1-4) and (5-6) were ligated together to form a 177 base pair molecule. As above, the ligation was digested with restriction enzymes to create the necessary ends for subsequent cloning of the molecule. In this case, the ligation of fragments (1-4) and (5-8) was digested with Nco I and Sph I. The digested ligation product DNA segment was run on a 6 percent polyacrylamide gel. The band of 177 base pairs was excised and eluted from the gel.

The 177 base pair fragment was cloned into plasmid pARC466. Plasmid pARC466 is a plasmid identical to M13mp19 except that an Nco I site has replaced the native Hind III site. This plasmid contains a polylinker region including a Sma I site that is downstream from the Sph I site.

The Nco I site in plasmid pARC466 was created by replacing the originally present Hind III site using in vitro mutagenesis as discussed previously. The primer used was:

```
                              Nco I
5'  CCT GCA GGC ATC CAA CCA TGG CGT
                                      (SEQ ID NO:40)
                AAT CAT GGT CAT 3'
```

Plasmid pARC466 was digested with Nco I and Sph I. The 177 bp transit peptide DNA fragment ends were designed to clone into these sites. The ligation of the 177 base pair fragment into plasmid pARC466 resulted in plasmid pARC480. Plasmid pARC480 was sequenced by M13 protocol to check the sequence of the designed peptide, which sequence was found to be correct.

ii. Plasmid pATe212

The transit peptide was moved into a plasmid that contained a plant promoter and termination sequence. pCaMVCN is a plasmid supplied by Pharmacia that contains the cauliflower mosaic virus 35S promoter and a NOS polyadenylation sequence. The transit peptide was cloned next to the 35S promoter as follows:

a) Plasmid pCaMVCN was digested with the restriction enzyme Sal I. Linker #1104 from New England Biolabs d(TCGACCCGGG) was digested with Sal I and then ligated with the digested pCaMVCN to create plasmid pATC209.

b) Plasmid pATC209 was digested with Sma I. Plasmid pARC480 was digested with Nco I and Sma I to remove the transit peptide. The Nco I site of the transit peptide DNA was treated with the Klenow fragment of E. coli DNA polymerase to create a blunt end to make that fragment compatible with the Sma I site of plasmid pATC209. The double blunt-ended fragment was cloned into the Sma I-digested plasmid pATC209 to create Plasmid pATC212.

iii. Plasmid pATC255

Plasmid pATC255 is a derivative of plasmid pGA482 that contains the gene for GGPP synthase with the transit peptide sequence in frame with the coding sequence of the GGPP synthase gene. This gene construct is driven by the CaMV 35S promoter and contains the NOS polyadenylation site downstream of the structural gene. The plasmid was made in the following way.

The plasmid pARC498 contains a version of the GGPP synthase gene with a Sph I site at the initiation. methionine codon and a Sph I site after the stop codon following the GGPP synthase structural gene sequence. Plasmid pARC498 was digested with Sph I.

Plasmid pATC212 was also digested with Sph I. The Sph I site is at the 3' end of the transit peptide sequence. The above Sph I GGPP synthase gene fragment was cloned into the Sph I site of the pATC212 plasmid, resulting in plasmid pATC216.

Plasmid pATC216 contains the CaMV 35S promoter, the transit peptide sequence, the GGPP synthase structural gene, and the NOS polyadenylation sequence. This whole region of plasmid pATC216 can be moved as a Hind III-Bgl II fragment, since there is a Hind III site upstream from the CaMV 35S promoter and a Bgl II site downstream from the NOS polyadenylation sequence.

Plasmid pATC216 was digested with Hind III and Bgl II and the Hind III-Bgl II fragment was cloned into the Hind III and Bgl II sites of plasmid pGA225. The resulting plasmid is pATC255.

f. Production in the Plant Cytoplasm

To prepare GGPP synthase in the cytoplasm, the carotenoid genes described before are introduced into appropriate vector(s), as also described above for chloroplasts, using identical techniques, except that the transit peptide is eliminated. Because they are not targeted to the chloroplast, the enzymes remain in the cytoplasm, and can be isolated from the cytosol.

Example 4. Phytoene Synthase Gene a. Digestion of pARC376 with Pst I

The plasmid pARC376-Pst 122 was created by deletion of an approximately 592 bp Pst I *Erwinia herbicola* DNA fragment from Pst I sites at about 5807 to about 5215 of plasmid pARC376 (FIG. 5), followed by religation of the larger of the two fragments. The Eco RI (about 3370) to Hind III (about 13463) fragment from plasmid pARC376-Pst 122, which contains the desired *Erwinia herbicola* DNA fragment, was cloned into the plasmid pARC305A, resulting in plasmid pARC139.

The plasmid pARC305A contains the polycloning linker from pUC18, the chloramphenicol acetyltransferase gene (CAT) that confers chloramphenicol resistance in *E. coli* and the pMB1 origin of replication. The plasmid pARC305A is an analogous plasmid to plasmid pUC18 except plasmid pARC305A contains the CAT selectable marker whereas pUC18 contains the ampicillin selectable marker.

When the resulting *Erwinia herbicola* DNA was inserted into the plasmid pARC305A to create the plasmid pARC139 and introduced into *E. coli* cells, no carotenoids were made, as expected.

An impairment of the gene for phytoene synthase would cause the *E. coli* cells not to produce any colored carotenoids. Therefore, the deletion of this 592 bp region could have deleted part of the gene for phytoene synthase.

b. Construction of Plasmid pARC285

The construction of plasmid pARC285 used the approximately 1112 bp Nco I to Eco RI fragment from the plasmid pARC376-Bam 100. The plasmid pARC376-Bam 100 is a derivative of the pARC376 plasmid in which the approximately 1045 bp Bam HI fragment from about position 3442 to about position 4487 (FIG. 5) and the approximately 815 bp Bam HI fragment from about position 4487 to about 5302 (FIG. 5) were deleted. A total of about 1860 nucleotides was deleted from the pARC376 plasmid. As a result of the deletions of the Bam HI fragments from plasmid pARC376, the Bam HI site at about 5302 at the 3' end was brought within about 72 nucleotides of the Eco RI site originally at about position 3370 of plasmid pARC376. The resulting restriction fragment therefore contained about 1112 bp and was bounded by Nco I and Eco RI restriction sites at its 5' and 3' ends, respectively.

The phytoene synthase gene is contained on an approximately 1040 bp Nco I to Bam HI restriction fragment (corresponding approximately to positions 6342 and 5302 of FIG. 5, respectively), but it can be cloned into other plasmids as an approximately 1112 bp Nco I to Eco RI fragment. The approximately 1112 bp Nco I to Eco RI fragment was excised from the plasmid pARC376-Bam 100 and cloned into the Nco I to Eco RI sites of plasmid pARC306A to generate plasmid pARC285. The relevant portion of the phytoene synthase gene can thus be excised from plasmid pARC285 as an approximately 1112 bp Nco I to Eco RI fragment.

c. Construction of Plasmid pARC140N.

Analysis of the region surrounding the Nco I (about position 6342) site revealed that the methionine codon internal to the Nco I site was in an open reading frame that had another methionine codon 13 amino acid residues upstream. Immediately upstream from this methionine codon, was a consensus sequence for the ribosome binding site (AGGA) that is often found in prokaryotic organisms upstream from the initiation codon of a gene.

To determine if the upstream methionine was in fact the initiation codon, a Bgl II site was introduced immediately upstream from the methionine codon of the Nco I site, using in vitro mutagenesis, as described before. Two complementary polynucleotide sequences were made that contained a Nco I overhang on one end and on the other end a Bgl II overhang. The sequences were as follows:

```
Bgl II                                                    Nco I
5'                                                              3'
   GATCT AAAATGAGCC AACCGCCGCT GCTTGACCACGCC ACGC AGAC
                                                (SEQ ID NO:41)
         ATTTT ACTCGGTTGGCGGCGACGAACTGGTGCGGTGCGTCTGGTAC
   3'                                                           5'
                                                (SEQ ID NO:42)
```

The two complementary single stranded polynucleotide sequences were hybridized together, ligated to an approximately 1112 bp Nco I-Eco RI fragment from plasmid pARC285 containing the approximately 1040 bp Nco I to Bam MI phytoene synthase gene region and cloned into plasmid pARC135.

The plasmid pARC135 (shown in FIG. 7) is composed of the pUC18 vector containing the yeast pGK promoter and terminator sequences separated by a unique Bgl II site.

First, the approximately 3.1 kb Hind III fragment of yeast (S. cerevisiae) containing the pGK gene was cloned into the Mind III site of pUC18 to create plasmid pSOC117 (also referred to herein as plasmid pARC117). Next, a Bgl II site was introduced by oligonucleotide mutagenesis upstream of the initiating ATG codon of the pGK gene contained within a mp19M13 clone, producing the change shown below in bold.

```
Native P G K Sequence:                          Met  Ser  Leu
     . . . A C A A C A A A A T A T A A A A A C A  ATG  TCT  TTA
                                                (SEQ ID NO:43)

New P G K Sequence:
     . . . A C A A C A A G A T C T A A A A A C A  ATG  TCT  TTA
               Bgl    II    Site                (SEQ ID NO:44)
```

Then, an approximately 1.1 kb Bst XI fragment, carrying the introduced Bgl II PGK site, was excised from the mp19 clone and used to replace the homologous Bst XI fragment within plasmid pSOC117. Finally, the Bgl II fragment, containing the majority of the PGK structural gene, was removed by Bgl II digestion, and the plasmid was religated to yield plasmid pARC135. Plasmid pARC135 was digested with Nco I and Eco RI, the resulting gene was thereafter manipulated, as discussed below, to generate the plasmid pARC140R, which contains the S. cerevisiae phosphoglyceric acid kinase (PGK) promoter at the Bgl II site.

The experimental protocol for the construction of pARC140R is described below.

A. Hybridization/Annealing of the two oligonucleotide probes (oligonucleotide probes were not phosphorylated at the 5' end).

1) The two complementary oligonucleotide probes were annealed in 25 µl of solution containing:
   10 µl of oligonucleotide #1 (about 1 µg)
   10 µl of oligonucleotide #2 (about 1 µg)
   1.65 µl of 1M Tris-Cl$_2$ (pH 8.0)
   2.5 µl of 100 mM MgCl$_2$
   0.45 µl water 2) The probe solution was incubated at 65° C. for 10 minutes. Then it was cooled according to the following regime:
   20 minutes at 55° C.
   20 minutes at 42° C.
   20 minutes at 37° C.
   30 minutes at room temperature (24° C.)

B. An approximately 1112 bp fragment from Nco I to Eco RI in plasmid pARC285, Containing an approximately 1040 bp (Nco I to Bam HI) sequence was excised and isolated from the gel. This approximately 1112 bp fragment contained the shortened version of the gene for phytoene synthase.

C. The annealed oligonucleotide probes were ligated overnight (15 hours at 15° C.) to the approximately 2 bp (Nco I to Eco RI) fragment according to the following protocol:

| | |
|---|---|
| Annealed oligos | 25 µl |
| Nco I-Eco RI fragment | 20 µl (about 1 µg) |
| 10 X Ligation Buffer | 5 µl (IBI, Corp.) |
| T4 Ligase (Boerhinger-Mannheim) | |

The result from the ligation was the following:

```
Bgl II      Nco I              Bam HI        Eco RI
I--------·I------------------·I-------------·I
```

D. The mixture was subsequently phenol extracted, chloroform: isoamyl alcohol (24:1) extracted and then ethanol precipitated. The DNA pellet was resuspended in 27 µl water.

E. The DNA pellet was then digested for 30 minutes at 37° C. with Eco RI to remove any dimers that may have formed during the ligations.

| | |
|---|---|
| DNA fragment | 27 µl |
| Eco RI digestion buffer (BRL) | 3 µl |
| Eco RI enzyme (BRL) | 3 µl (30 U) |

F. The products of the Eco RI digestion were separated by electrophoresis on a 0.7 percent agarose gel. The fragment (about 1158 bp) was isolated from the gel.

G. This Bgl II to Eco RI fragment was cloned into the Bgl II and Eco RI sites of the plasmid pARC135 as follows. About 5 µg of plasmid pARC135 was digested with Bgl II and Eco RI and then separated on a 0.7 percent agarose gel. A DNA fragment (about 4 kb) was isolated. The approximately 1158 bp Bgl II to Eco RI fragment containing the full length phytoene synthase gene was cloned into the approximately 4 kb vector in the Bgl II and Eco RI sites according to the following protocol:

| | |
|---|---|
| pARC135 Bgl II/Eco RI digested | 10 µl (about 0.2 µg) |
| Bgl II to Eco RI fragment | 20 µl (about 0.5 µg) |
| 10 X ligation buffer | 3 µl |
| T4 ligase | 2 µl (4 Units) |

The reaction was incubated overnight (about 15–18 hours) at 15° C.

H. The ligated DNA was cloned into DH5-alpha E. coli cells obtained from BRL.

I. Transformants were grown in the presence of 100 µg/ml of ampicillin. Colonies containing the cloned DNA fragment were identified by growing prospective clones in the presence of ampicillin, isolating plasmid DNA by the alkali lysis procedure and performing restriction enzyme analysis on the clones. The result of this cloning procedure was a plasmid named pARC140R that contained the desired genes.

Upstream from the ATG methionine codon, three adenine residues were introduced. Presence of adenine residues adjacent to the initiation codon has been correlated with genes that are highly expressed in S. cerevisiae. These residues had been inserted in the sequence to cause high level expression of a gene in S. cerevisiae (Hamilton et al., Nucleic Acids Research, 15:3581 1987). The plasmid pARC140R contains the S. cerevisiae promoter from the gene for phosphoglyceric acid kinase (PGK) adjacent to the gene for phytoene synthase.

The modified phytoene synthase structural gene was excised from plasmid pARC140R as an approximately 1158 bp Bgl II-Eco RI fragment, engineered and cloned into plasmid pARC306N to generate plasmid pARC140N. The plasmid pARC306N is similar to plasmid pARC306A except that instead of an Nco I site adjacent to the E. coli Rec 7 promoter, there is an Nde I site.

More specifically, plasmid pARC306N was digested with Nde I and then digested with S1 nuclease to blunt the ends of the former Nde I sites. The plasmid was thereafter digested with Eco RI to remove one of the blunt ends and provide an Eco RI sticky end.

Plasmid pARC140R was digested with Bgl II and then with S1 nuclease to blunt the resulting ends. The digested and blunt-ended plasmid was then further digested with Eco RI to remove one of the blunt ends and provide an Eco RI sticky end for the DNA containing the phytoene synthase structural gene. That structural gene was therefore in a fragment of about 1164 bp with a blunt end at one end and an Eco RI site at the other end.

The above phytoene synthase structural gene-containing DNA segment was ligated into the blunt end and to Eco RI portions of the above-digested plasmid pARC306N to operatively link the two DNA segments together and form plasmid pARC140N. The phytoene synthase structural gene-containing DNA segment can be excised from plasmid pARC140N as an approximately 1176 bp Hpa I-Eco RI fragment, an approximately 1238 bp Pvu II-Eco RI fragment or as a still larger fragment using one of the restriction sites in the polylinker region downstream from the Eco RI site (see, FIG. 6).

The plasmid pARC140N, was transferred into E. coli cells that contained the plasmid pARC139, in which part of the gene for phytoene synthase was deleted and, those E. coli cells were therefore incapable of producing any colored carotenoids. When plasmid pARC140N was added to those E. coli cells containing plasmid pARC139, the cells produced colored carotenoids. This demonstrated that the modified gene for phytoene synthase coded for a functional enzyme.

E. coli cells containing plasmid pARC140N were induced with nalidixic acid to produce large amounts of the phytoene synthase protein according to the protocol discussed hereinbefore. The protein fraction was isolated and analyzed by SDS-PAGE and revealed that the size of phytoene synthase protein is 38 kilodaltons.

Example 5. Phytoene Production in E. coli a. Method One—Plasmid containing the engineered genes for GGPP synthase and phytoene synthase A plasmid containing genes for both GGPP synthase and phytoene synthase, as well as an associated promoter regulatory region adjacent to a structural gene causes E. coli cells containing this plasmid to produce phytoene. An example of such a plasmid construct is the use of the Structural gene for GGPP synthase from the plasmid pARC489D with a promoter that functions in E. coli adjacent to the 5' end of the structural gene for GGPP synthase. This construct is introduced into a common cloning vector such as pUC18. Where the structural genes are linked together, a single promoter can function in E. coli to express both gene products.

A before-described structural gene for phytoene synthase excised from the plasmid pARC140R is cloned adjacent to a promoter that functions in E. coli, such as Rec 7. This Rec 7 promoter-phytoene synthase heterologous gene is then introduced into a plasmid containing the gene for GGPP synthase. The plasmid containing both of these genes directs phytoene synthesis in E. coli. The two genes can also be placed end-to-end in E. coli under the control of a single promoter.

b. Method Two—Plasmid pARC376 with a defective gene for phytoene dehydrogenase-4H Phytoene production can occur with the native pARC376 plasmid in which the genes for GGPP synthase and phytoene synthase are functional and produce functional proteins, but in which the gene for phytoene dehydrogenase-4H is impaired, thereby impairing the production of lycopene from phytoene. A plasmid pARC376 derivative in which the gene for phytoene dehydrogenase-4H is deleted or in some other way impaired could not further metabolize the phytoene being produced in the E. coli cells due to the action of the genes for GGPP synthase and phytoene synthase. Under this condition, phytoene accumulates. The gene for phytoene dehydrogenase-4H is located approximately between the positions 7849 to 6380 of plasmid pARC376 as shown in FIG. 5.

By example, two different pARC376 derivative plasmids that contain deletions at the beginning of the gene for phytoene dehydrogenase-4H have been made as described before. One plasmid is pARC376-Bam 127, in which the approximately 2749 bp Bam HI fragment from about position 7775 to about 10524 (FIG. 5) was deleted. The other was plasmid pARC376-Pst 110 missing a Pst fragment at 7792–10791 (FIG. 5). These plasmids were constructed by partially digesting plasmid pARC376 with either Bam HI or Pst I, and ligating the respective DNA fragments together.

These deletions caused the gene for phytoene dehydrogenase-4H to be non-functional, since the beginning part of the gene was deleted. E. coli cells that contained either plasmid pARC376-Bam 127 or plasmid pARC376-Pst 110 produce phytoene. Phytoene is colorless and cells that produce phytoene have the same colorless character as normal E. coli cells. The ligation mixture was transformed into E. coli and any resulting colorless colonies were analyzed for the presence of phytoene. The presence of phytoene was confirmed by growing E. coli cells containing the plasmid, performing an extraction according to the following protocol, and identifying phytoene by HPLC analysis in the extract.

c. Identification of Phytoene Produced by Transformed E. coli i. Extraction from cells One hundred to 500 mg of lyophilized E. coli cells containing an above-described plasmid were resuspended in 3 ml of 7:2 acetone:methanol in 15 ml conical glass tube with teflon seal cap. 450–600 Micron glass beads (1:1 ratio with the cells) were added to the tube, which was covered with foil and vortexed for 2 minutes. After 5 minutes, the tube was spun in a table top centrifuge and the supernatant transferred to a foil covered glass vial. This extraction was repeated multiple times.

The entire pool of the extract was filtered through a 0.2 micron Acrodisc CR filter in a glass syringe, and the filtrate was dried under nitrogen. Utmost care was taken to protect the carotenoids/xanthophylls from light and heat.

ii. Identification

The presence of phytoene was monitored by thin layer chromatography (TLC) analysis in three different solvent systems using authentic phytoene as a reference.

The carotenoids/xanthophylls were separated by high pressure liquid chromatography (HPLC) with the aid of a Hewlett Packard C-18 Vydac analytical column (4.6×250 mm, 5 micron particle size). A linear gradient from 30 percent isopropanol and 70 percent acetonitrile:water (9:1) to 55 percent isopropanol and 45 percent acetonitrile:water (9:1) in 30 minutes (min) at 1 ml/min resolved most of the compounds of interest with the following retention times—zeaxanthin 8.7 min, lycopene 16.2 min, beta-carotene 18.1 min, phytofluene 19.9 min, phytoene 21.8 min, and the zeaxanthin diglucosides were clustered between 6 and 8 min.

The amount of phytoene produced in these cells averaged about 0.01 percent (dry weight).

Example 6. Phytoene Production in S. cerevisiae

S. cerevisiae does not normally produce carotenoids since it does not have the necessary functional genes for phytoene production. S. cerevisiae does, however, produce farnesyl pyrophosphate (FPP). For phytoene-production to occur in S. cerevisiae, the genes for GGPP synthase and phytoene synthase need to be transferred into the S. cerevisiae cells in the proper orientation to permit the expression of functional enzymes.

Promoter sequences that function in S. cerevisiae need to be placed adjacent to the 5' end of the structural genes for GGPP synthase and phytoene synthase and termination sequences can also be placed at the 3' ends of the genes. The genes for GGPP synthase and phytoene synthase that contain the proper regulatory sequences for expression in S. cerevisiae then are transferred to the S. cerevisiae cells.

a. Construction of Plasmid pARC145B

The vector pSOC713 (FIG. 8), was made by first using Klenow polymerase to make blunt ends on the Eco RI fragment of the yeast B-form 2-micron circle that contains the 2-micron origin of replication. Thus, the blunt-ended fragment was cloned into the Sma I site of pUC8. The 2-micron fragment was removed from the pUC8 construct by cleavage with Eco RI and Bam HI. This Eco RI-Bam HI fragment was ligated to the Eco RI-Bgl II fragment of yeast DNA which contains the TRP 1 gene. The DNA containing the fused TRP i to 2-micron fragment was ligated as an Eco RI fragment into the Eco RI site of pUC18. Finally, a region of the yeast genome, containing the divergently-facing GAL 10 and GAL 1 promoters was ligated as an Eco RI to Bam HI fragment into the above TRP ½-micron/pUC18 plasmid, which had been cleaved with Eco RI and Bam HI. The restriction map of plasmid pSOC713 is shown in FIG. 8.

Three modifications were made to plasmid pSOC713 to yield plasmid pARC145B (FIG. 9). First, plasmid pSOC713 was partially digested with Eco RI and the ends were made blunt with Klenow polymerase and self-ligated. The resultant plasmid contained a unique Eco RI site adjacent to the GAL 1 promoter region. This plasmid was cleaved with Eco RI and the synthetic oligonucleotide shown below, 5' AATTCCCGGGCCATGGC 3'    (SEQ ID NO:45)
3'     GGGCCCGGTACCGTTAA 5' (SEQ ID NO:46)

was ligated into the Eco RI site. This regenerated one Eco RI site followed by Sma I and Nco I sites. Finally, the single Bam HI site was cut, filled in with Klenow polymerase, and the Bgl II synthetic linker oligonucleotide

CAGATCTG
GTCTACTG was ligated, cut with Bgl II, and then self-ligated to make a Bgl II site flanked by two Bam HI sites. The restriction map of plasmid pARC145B is shown in FIG. 9.

b. Construction of Plasmid pARC145G

The engineered gene for GGPP synthase contained in plasmid pARC489D, which encoded the most active version of the enzyme in E. coli above, was transferred to the S. cerevisiae vector pARC145B to generate plasmid pARC145F. This was accomplished by digestion of plasmid pARC489D with Nco I and Pvu II to obtain the approximately 1000 bp Nco I-Pvu II restriction fragment that contained the GGPP synthase structural gene. An Nco I linker was added to the Pvu II site of the restriction fragment to make that fragment an Nco I-Nco I fragment containing about 1010 bp. The GGPP synthase gene was cloned adjacent to the S. cerevisiae divergent promoter region GAL 10 and GAL 1 so that the GGPP synthase gene would be expressed in S. cerevisiae using the GAL 10 promoter.

The gene for phytoene synthase from plasmid pARC140R (Example 2) was excised and placed adjacent to the other side of the GAL 1 promoter of plasmid pARC145F so that the phytoene synthase gene would also be expressed using the GAL 1 promoter. Thus, the transcription termination sequence from the S. cerevisiae gene PGK was cloned at the 3' end of the gene for phytoene synthase.

More specifically, plasmid pARC145F was digested with Bgl II and Sph I, whose restriction sites are illustrated in FIG. 9 for precursor plasmid pARC145B. The phytoene synthase structural gene was excised from plasmid pARC140R as an approximately 1158 Bgl II-Eco RI fragment; the same structural gene is present in the approximately 1176 bp Hpa I-Eco RI fragment of plasmid pARC140N. The approximately 500 bp pGK termination sequence from another plasmid, pARC117, was excised as an Eco RI-Sph I fragment such as the same fragment shown in plasmid pARC135 of FIG. 7. The Bgl II-Sph I digested plasmid pARC145F, the Bgl II-Eco RI about 1158 bp plasmid pARC140R fragment and the about 500 bp Eco RI-Sph I PGK termination sequence were triligated to operatively link the three sequences together.

This ligation placed the phytoene synthase structural gene adjacent to and under the control of the GAL 1 promoter at the 5' end of the structural gene. The PGK termination sequence was placed at the 3' end of the phytoene synthase structural gene. The resulting plasmid, now containing both of the genes required for phytoene production under control of the GAL 10 and GAL 1 divergent promoters, was named plasmid pARC145G, and is shown in FIG. 10. Other relevant features of plasmid pARC145G include the 2 micron origin of replication of S. cerevisiae and the TRP 1 gene of S. cerevisiae as a selectable marker.

The plasmid pARC145G was transferred into the S. cerevisiae strain YPH499 (provided by Dr. Phillip Heiter, johns Hopkins University) that lacked a functional TRP 1 gene. This strain was able to utilize galactose as a carbon source. Transformants were isolated,.and the cells were grown in the presence of galactose to induce the GAL 10 and GAL 1 promoters to express the genes for phytoene production.

The S. cerevisiae cells were grown on the media described below to produce phytoene. YPH499 is a strain of yeast that contains an impaired TRP 1 gene and an impaired URA 3 gene, and is able to utilize galactose as carbon and energy sources. This strain requires tryptophan and uracil in the growth medium in order to grow. Alternatively, these strains can be grown if they are transformed with a plasmid (or plasmids) containing a normal copy of either the TRP 1 gene, but not a normal copy of the URA 3 gene, in which case the cells require uracil to be added to the growth medium, or the URA 3 gene, but not a normal copy of the TRP 1 gene, in which case the cells need to have tryptophan added to the growth medium.

There are four different media used to grow this strain of Saccharomyces:

Medium 1 is used if the cells contain no further URA 3 or TRP 1 genes.

Medium 2 is used if the cells contain a plasmid(s) with only the TRP 1 gene.

Medium 3 is used if the cells contain a plasmid(s) with only the URA 3 gene.

Medium 4 is used if the cells contain a plasmid(s) with both the TRP 1 and the URA 3 genes.

The media constituents are as follows:

Basic Constituents:
0.67% Yeast Nitrogen Base without Amino Acids (Source Difco, #0919-15);
2% Galactose; and
720 mg/l Dropout Mixture*
For Medium 1 (Complete)

| Constituent | Amount (mg) |
| --- | --- |
| adenine | 400 |
| uracil | 400 |
| tryptophan | 400 |
| histidine | 400 |
| arginine | 400 |
| methionine | 400 |
| tyrosine | 600 |

Basic Constituents:
0.67% Yeast Nitrogen Base without Amino Acids (Source Difco, #0919-15);
2% Galactose; and
720 mg/l Dropout Mixture*
For Medium 1 (Complete)

| Constituent | Amount (mg) |
| --- | --- |
| leucine | 1200 |
| lysine | 600 |
| phenylalanine | 1000 |
| threonine | 4000 |
| aspartic acid | 2000 |
| For Medium 2, without the tryptophan. | |
| For Medium 3, without the uracil. | |
| For Medium 4, without both tryptophan and uracil. | |

*Dropout Mixtures

To prepare a dropout mixture all of the desired constituents were added to a mortar and ground thoroughly with a pestle. The constituents were thoroughly mixed and 720 mg of the dropout mixture were added for each liter of medium.

The plasmid pARC145G contains both the GGPP synthase and phytoene synthase genes and a normal copy of the TRP 1 gene. Saccharomyces cells containing plasmid pARC145G were grown in Medium 2 with 2 percent galactose.

The S. cerevisiae cells were analyzed for the presence of phytoene. A total of 0.12 percent (dry weight) phytoene and related compounds having superimposable UV-Vis spectra as phytoene was found in the cells.

EXAMPLE 7

Phytoene Production in *Pichia pastoris*

The above method is also extendable to other yeasts. One yeast system that serves as an example is the methylotrophic yeast, *Pichia pastoris*.

To produce phytoene in *P. pastoris*, structural genes for both GGPP synthase and phytoene synthase are placed under the control of regulatory sequences that direct expression of structural genes in Pichia. The resultant expression-competent forms of those genes are introduced into Pichia cells.

For example, the transformation and expression system described by Cregg et al., *Biotechnology* 5:479–485 (1987); *Molecular and Cellular Biology* 12:3376–3385 (1987) can be used. A structural gene for GGPP synthase such as that from plasmid p489D is placed downstream from the alcohol oxidase gene (AOX1) promoter and upstream from the transcription terminator sequence of the same AOX1 gene. Similarly, a structural gene for phytoene synthase such as that from plasmid 140N is placed between an AOX1 promoter and terminator. Both of these genes and their flanking regulatory regions are then introduced into a plasmid that carries both the *P. pastoris* HIS4 gene and a *P. pastoris* ARS sequence (Autonomously Replicating Sequence), which permit plasmid replication within *P. pastoris* cells [Cregg et al., *Molecular and Cellular Biology*, 12:3376–3385 (1987)].

The vector also contains appropriate portions of a plasmid such as pBR322 to permit growth of the plasmid in *E. coli* cells. The final resultant plasmid carrying GGPP synthase and phytoene synthase genes, as well as the various additional elements described above, is illustratively transformed into a his4 mutant of *P. pastoris*, i.e. cells of a strain lacking a functional histidinol dehydrogenase gene.

After selecting transformant colonies on media lacking histidine, cells are grown on media lacking histidine, but containing methanol as described Cregg et al., *Molecular and Cellular Biology*, 12:3376–3385 (1987), to induce the AOX1 promoters. The induced AOX1 promoters cause expression of the enzymes GGPP synthase and phytoene synthase and the production of phytoene in *P. pastoris*.

Both GGPP synthase and phytoene synthase genes can also be introduced by integrative transformation, which does not require the use of an ARS sequence, as described by Cregg et al., *Molecular and Cellular Biology*, 12:3376–3385 (1987).

EXAMPLE 8

Phytoene Production in *A. nidulans*

The genes encoding GGPP synthase and phytoene synthase as discussed before can be used to synthesize and accumulate phytoene in fungi such as *Aspergillus nidulans*. Genes are transferred to Aspergillus by integration.

For example, the structural gene for GGPP synthase is introduced into the *E. coli* plasmid pBR322. The promoter from a cloned Aspergillus gene such as argB [Upshall et al., *Mol. Gen. Genet.* 204:349–354 (1986)] is placed into the plasmid adjacent to the GGPP synthase structural gene. Thus, the GGPP synthase gene is now under the control of the Aspergillus argB promoter.

Next, the entire cloned amds gene [Corrick et al., *Gene* 53:63–71 (1987)] is introduced into the plasmid. The presence of the amds gene permits acetamide to be used as a sole carbon or nitrogen source, thus providing a means for selecting those Aspergillus cells that have become stably transformed with the amds-containing plasmid.

Thus, the plasmid so prepared contains the Aspergillus argB promoter fused to the GGPP synthase gene and the amds gene present for selection of Aspergillus transformants. Aspergillus is then transformed with this plasmid according to the method of Ballance et al., *Biochem. Biophys. Res. Commun.* 112:284–289 (1983).

The phytoene synthase structural gene is similarly introduced into the *E. coli* plasmid pBR322. The promoter for the cloned Aspergillus argB gene [Upshall et al., *Mol. Gen. Genet*, 204:349–354 (1986)] is placed immediately adjacent to the phytoene synthase structural gene. Thus, the phytoene synthase structural gene is controlled by the Aspergillus argB promoter.

The entire, cloned Aspergillus trpC gene [Hamer and Timberlake, *Mol. Cell. Biol.*, 7:2352–2359 (1987)] is introduced into the plasmid. The trpC gene permits selection of the integrated plasmid by virtue of permitting transformed trpC mutant Aspergillus cells to now grow in the absence of tryptophan. The Aspergillus strain, already transformed with the plasmid containing the GGPP synthase gene, is now capable of synthesizing phytoene.

EXAMPLE 9

Phytoene Synthase Production in Higher Plants a. Construction of the plasmid pATC1615.

Plasmid pARC283 was first constructed in order to provide an appropriate template for the polymerass chain reaction (PCR), below. The construction of plasmid pARC283 used the approximately 1534 bp Bgl II to Bam HI fragment of plasmid pARC376 (from about position 6836 to about position 5302 of FIG. 5). Polylinker fragments, which contain multiple unique restriction sites, were ligated to the ends of this Bgl II-Bam HI fragment. The resulting fragment was digested with Eco RI and cloned into the Eco RI site of plasmid pBR322. The resulting plasmid was named pARC283.

The phytoene synthase structural gene of this plasmid was modified to introduce the restriction site Sph I at the initiation methionine codon and a Sal I restriction site at the 3' end of the gene. To accomplish these modifications, the Eco RI-Eco RI fragment was excised from plasmid pARC283. This fragment was isolated on agarose gel electrophoresis and used as the template for PCR. The following oligonucleotide probe was used to create the Sph I site at the ATG start codon of the phytoene synthase gene:

5' TCG CAT GCG CCA ACG CCG CTG CTT GAC CAC GC 3'
       Sph I      (SEQ. ID. NO:47)

in which bold letters indicate changed nucleotides. This modification changed the second residue from the serine shown in FIG. 4 to an arginine. The following oligonucleotide probe was used to create the Sal I site at the 3' end of the gene:

5' CTG TCG ACG GCT ACT GAG CGG CTC TAC GTC 3'
      Sal I      (SEQ. ID. NO:48)

The introduction of a Sal I site at the 3' end of the phytoene synthase gene changed the DNA sequence as indicated below:

Original Sequence:
5' GAC GTA GAG CCG CTT CAG GTA GCC CCG GCG 3'
                   (SEQ ID NO:49)

New Sequence:
5' CAC GTA GAG CCG CTC AGT AGC CGT CGA CAG 3'
                   (SEQ ID NO:50), in a which bold-faced letter in the new sequence indicates an altered base.

Although there are only 15 nucleotides of the PCR probe that hybridize exactly to the original 3' sequence, the hybridization conditions under which the PCR was performed makes this amount of hybridization sufficient for the PCR to function appropriately to introduce the alterations noted in the sequence.

The probes were resuspended in a volume of sterile water such that the final concentration of each probe was 10 pmoles/µl. The PCR reaction was conducted as described in Example 3, part b.

b. Cloning of the PCR Produced DNA Fragment

The DNA produced by the PCR reaction was digested with Sph I and Sal I. This about 1065 bp Sph I-Sal I PCR generated fragment was isolated and recovered from an agarose gel. Plasmid pUC18 (Pharmacia) was likewise digested with Sph I and Sal I. The Sph I-Sal I PCR fragment was cloned into the Sph I-Sal I sites of plasmid pUC18. The resulting plasmid was named pATC1611.

c. Proof of Functional Genetically Engineered Phytoene Synthase Gene

The proper functioning of the phytoene synthase gene of plasmid pATC1611 was assayed by cloning the PCR modified gene into an *E. coli* expression vector. This was done by first digesting plasmid pATC1611 with Hind III and Eco-RI.

The resulting Hind III-Eco RI fragment was isolated and recovered from an agarose gel, and treated with the Klenow fragment of DNA polymerase I to fill in the fragment termini to create blunt ends.

This blunt ended fragment was then cloned into plasmid pDR540 (Pharmacia), A plasmid that contains the TAC promoter active in *E. coli*. Thus, plasmid pDR540 was cut with Bam HI and the Klenow fragment was used to fill in the ends, as above. The now blunt ended originally Hind III-Eco RI fragment containing the phytoene synthase gene was ligated to the blunt ended Bam HI-treated pDR540. This plasmid construct was cut with Hind III to provide a Hind III-Hind III fragment that contained the phytoene synthase gene and the TAC promoter. That Hind III-Hind III fragment was then ligated into the Hind III site of plasmid pARC139.

Plasmid pARC139, discussed in Example 3, carries a deletion in the phytoene synthase gene. Addition of a functional copy of the phytoene synthase gene to plasmid pARC139 restores the ability of *E. coli* cells transformed with such a construct to produce colored carotenoids. The PCR modified phytoene synthase gene led to the production of colored carotenoids in *E. coli*, indicating that the modifications introduced into the gene via the PCR process did not affect the production of phytoene synthase from the modified gene.

d. Construction of Plasmid pATC1615

Plasmid pATC1611 was digested with Sph I and Hinc II. The resulting Sph I-Hind II fragment was cloned into the Sph I and Hinc II sites of plasmid pATC212, discussed in Example 3, to produce plasmid pATC1614.

Plasmid pATC1614 was digested with Xba I, generating a Xba I fragment which contained the 35S promoter, the transit peptide sequence, the phytoene synthase gene, and the NOS polyadenylation sequence. This Xba I fragment was cloned into the Xba I site of plasmid pGA482 (Pharmacia). The resulting plasmid was named pATC1615.

e. Construction of Plasmid pATC1620

Plasmid pATC1614, described above, was digested with Sal I. This generated a Sal I fragment containing the transit peptide sequence fused to the 5' end of the phytoene synthase gene. This Sal I fragment was treated with the Klenow fragment of DNA polymerase I to generate blunt ends.

Likewise, plasmid pNCN (Pharmacia) was digested with Bam HI and Sal I and treated with the Klenow fragment. The blunt ended Sal I fragment was ligated to the blunt ended plasmid pNCN to create plasmid pATC1618. This plasmid contains the NOS promoter sequence of *Agrobacterium tumefaciens* fused to the 5' end of the transit peptide sequence-phytoene synthase construct, and the NOS polyadenylation sequence fused to the 3' end of the gene.

This entire gene construct, namely, the NOS promoter sequence, the transit peptide sequence, the phytoene synthase structural gene, and the NOS polyadenylation sequence was removed from plasmid pATC1618 as a Hind III fragment. This Hind III fragment was cloned into the Hind III site of plasmid pGA482, to generate the plasmid pATC1620.

f. Production of Lutein in Plants

Plasmids pATC1615 and pATC1620 were transformed into Agrobacterium tumefaciens LBA4404 (Clontech, Inc.) according to standard protocols. Agrobacterium cells containing the plasmids with the phytoene synthase gene constructs were transferred by infection of tobacco leaf discs using the method of Horsch et al., *Science*, 227:1229–1231 (1985). During the infection process, the entire DNA segment between the left and right borders of the pGA482 plasmid is transfected into the plant cells. Transfected plant cells are selected for kanamycin resistance.

Western blot analyses of transformed tobacco plant chloroplasts indicated the presence of enhanced amounts of phytoene synthase.

The level of lutein in these transgenic plants was examined. Lutein, or xanthophyll, is one of the most widespread carotenoids in nature. Lutein is usually isolated by chromatography from nettles, algae, and the petals of many yellow flowers. Wildtype, untransformed tobacco plants average 0.13% of dry weight lutein. Viable transgenic tobacco plants transformed with plasmid pATC1615 contained an average of 0.16 percent of dryweight lutein, whereas tobacco plants transformed with pATC1620 contained an average of 0.21 percent of dryweight lutein, an average of over 1.6 times the wildtype levels. Some transformed tobacco plants had lutein levels 2 to 3 times higher than wildtype plants, with the highest level being 0.37% of dryweight lutein. These transgenic tobacco plants provide a new high level source of lutein. Several of the transgenic plants had orange patches or were themselves orange and were not viable.

Unexpectedly, transformed tobacco plants that exhibited high levels of lutein also exhibited high levels of chlorophyll that were on the order of 2 to 3 times higher than untransformed tobacco plants. The reason for the elevated chlorophyll levels is unclear, but it appears that an increase in the levels of the phytoene leads to an increase in the carotenoid and chlorophyll contents in the transformed plants.

g. Production in the Plant Cytoplasm

To prepare phytoene synthase in the cytoplasm, the carotenoid genes described before are introduced into appropriate vector(s), as also described above for chloroplasts, using identical techniques,.except that the transit peptide is eliminated. Because they are not targeted to the chloroplast, the enzymes remain in the cytoplasm, and can be isolated from the cytosol.

EXAMPLE 10

Phytoene Dehydrogenase-4H Gene a. Localization

The gene for phytoene dehydrogenase-4H is found on the plasmid pARC376. The general region of its location on this plasmid was shown by deleting specific regions of the pARC376 plasmid and analyzing the carotenoids produced. When an altered or mutated phytoene dehydrogenase-4H gene is generated, the phytoene that is produced by the presence of the two enzymes GGPP synthase and phytoene synthase would accumulate.

The pARC376 plasmid (FIG. 5) was partially digested with either Bam HI or Pst I restriction enzymes, and the free ends were ligated together. This DNA was transformed into *E. coli* HB101, and colorless colonies were picked and analyzed for the presence of phytoene. Two different plasmid deletions caused the *E. coli* cells to accumulate phytoene, including plasmid pARC376-Bam 127, which had a 2749 bp Bam HI fragment (7775–10524) deletion and plasmid pARC376-Pst 110, which had a 2999 bp Pst I fragment (7792–10791) deletion.

The plasmid pARC376-Pst 110 was constructed as follows. Plasmid pARC376 was partially digested with Pst I, the DNA was ligated, the ligation mixture was transformed into E. coli HB101, and the cells were grown in Luria-Broth supplemented with 100 μg/ml ampicillin. The transformants were screened by isolating plasmid DNA and performing restriction enzyme analysis. A plasmid with only the 2999 bp Pst I segment deleted, was identified and named pARC376-Pst 110. This deletion involves the beginning sequence of the gene for phytoene dehydrogenase-4H.

In E. coli cells containing either of the above two plasmids, phytoene accumulated to about 0.02 percent dry weight. This indicated that the gene for phytoene dehydrogenase-4H was present somewhere in the deleted region.

b. Construction of the plasmid pARC136

An about 12,000 bp Eco RI fragment from plasmid pARC376 was obtained by removal of the segment from about position 3370 to about position 379 (FIG. 5). The resulting large fragment containing all of the Erwinia herbicola carotenoid genes, was inserted into the Eco RI site of the pBluescript SK+plasmid (Stratagene, Inc., San Diego) resulting in plasmid pARC176B. Adjacent to the Eco RI site on the pBluescript plasmid is a Hind III site. There is another Hind III site in the insert from plasmid pARC376 (position 13463).

The plasmid pARC176B was digested with Hind III, releasing an about 10,200 bp fragment that contains all of the carotenoid genes. This fragment was cloned into the Hind III site of the plasmid pARC306A (described before and shown in FIG. 6). The resulting plasmid was named pARC137B.

There are two Sac I sites in the plasmid pARC137B; one in the polylinker from plasmid pARC306A, the other in the GGPP synthase structural gene at about position 11776 (FIG. 5). Diagrammatically, the orientation is as follows:

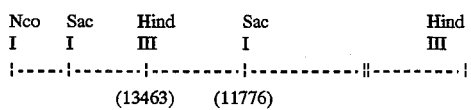

The plasmid pARC137B was digested with Sac I, deleting a 1700 bp Sac I fragment from the Sac I site in the polylinker to the Sac I site at position 11776. The remaining large DNA fragment was ligated together, forming plasmid pARC136, which was transformed into E. coli HB101, and grown in Luria-Broth supplemented with 100 μg/ml of ampicillin.

E. coli cells containing pARC136 were treated with nalidixic acid to induce the Rec 7 promoter (as described before). One of the proteins produced was a 51 kilodalton protein, which upon examination by polyacrylamide gel electrophoresis (PAGE) was determined to be the phytoene dehydrogenase-4H enzyme.

This protein was electroeluted and subjected to N-terminal amino acid sequencing. The sequence of the first 30 amino acids was determined. Comparison of the determined amino acid sequence of this 51 kilodalton protein with the DNA sequence of plasmid pARC376 indicated that the initiation site of the phytoene dehydrogenase-4H structural gene is located at about position 7849 of pARC376 (FIG. 5).

The 3' end of the phytoene dehydrogenase-4H gene extends beyond the Bgl II site at position 6836 (FIG. 5). The Bgl II site of the insert to plasmid pARC136 was digested and the ends were polished with the Klenow fragment of DNA Polymerase I, religated and transformed into E. coli cells. These manipulations caused an inhibition of phytoene dehydrogenase-4H and caused the E. coli cells to accumulate phytoene, indicating that the 3' end of the phytoene dehydrogenase-4H structural gene is downstream from the Bgl II site.

c. Construction of the Plasmid pARC496A

The plasmid pARC376 was digested with Sal I restriction enzyme to excise two adjacent DNA segments; an about 1092 bp Sal I segment (positions 9340–10432 of FIG. 5), and an about 3831 bp Sal I segment (positions 10432–14263 of FIG. 5). The free ends of the remaining DNA fragment were religated to form the plasmid, pARC271D.

To introduce a Nco I site at the initiation methionine of the structural gene for phytoene dehydrogenase-4H, an about 3035 bp Sal I (9340) to Xmn I (6305 of FIG. 5) fragment was excised from plasmid pARC271D. This fragment was isolated on agarose gel electrophoresis and used as the template for polymerase chain reaction (PCR). The following oligonucleotide probe was used:

```
            Nco I
5' AAA  CCA TGG  AAA AAA CCG TTG TGA TTG GC 3'
                                    (SEQ ID NO:51)
```

For the PCR to run properly, the 3' end must also be amplified in order to make the proper strands of the DNA fragment desired. The 3' end of the second strand oligonucleotide probe retaining the native DNA sequence was:

```
        Nco I        (Nco I site at position 6342 of FIG. 5)
5' GG  C CAT GG T CTG CGT GGC GTG 3'   (SEQ ID NO:52)
``` d. PCR Reaction:

The PCR reaction was performed as described in Example 3.

e. Cloning of the PCR Produced DNA Fragment

1) The DNA produced by the PCR reaction was digested with Nco I. This produced a DNA fragment of about 1505 bp, which was isolated and recovered from an agarose gel.

2) About 5 μg of the plasmid pARC306A was digested with Nco I.

3) About 100 ng of the Nco I-digested plasmid pARC306A was admixed With about 200 ng of the Nco I fragment produced by the PCR reaction. The fragments were inserted using ligation buffer (2 μl) (IBI Corp.) and 1 Unit of T4 ligase in a total volume of 20 μl. The ligation reaction was incubated at 4° C. for about 15 hours.

4) The ligation mixture was transformed into E. coli HB101. Transformants were selected on Luria-Broth with 100 μg/ml ampicillin. DNA was isolated from prospective clones and the clone carrying the phytoene dehydrogenase-4H gene insert was identified by restriction enzyme analysis. This plasmid was named pARC496A.

The DNA sequence for the phytoene dehydrogenase-4H gene was determined as described before and is shown in FIG. 11, along with some of the restriction sites. The approximately 1505 bp Nco I-Nco I fragment (Nco I fragment) present in plasmid pARC496A is a particularly preferred DNA segment herein.

f. Proof of a Functional Genetically Engineered Phytoene Dehydrogenase-4H Gene The proper functioning of the gone for phytoene dehydrogenase-4H in plasmid pARC496A was established by complementation of the plasmid pARC275 (described in Example 11). This plasmid has three relevant features: i) it is a derivative of plasmid pARC376 in which part of the gene for phytoene dehydrogenase-4H has been deleted, therefore, the plasmid causes the accumulation of phytoene in *E. coli*; ii) it contains the R1162 origin of replication; and iii) it contains a kanamycin resistance gene from Tn5, and therefore, *E. coli* cells that contain plasmid pARC275 are able to grow in the presence of 25 μg/ml kanamycin.

*E. coli* cells containing plasmid pARC275 were transformed with the plasmid pARC496A to form doubly transformed host cells. These host cells were grown in medium supplemented with 25 μg/ml kanamycin and 100 μg/ml of ampicillin. The cells produced lycopene at a level of about 0.01 percent dry weight.

This result demonstrated that the gene for phytoene dehydrogenase-4H had been successfully engineered. In addition, this result showed that the approximately 1505 bp Nco I-Nco I DNA segment present in plasmid pARC496A contained the entire DNA sequence required to produce a functional phytoene dehydrogenase-4H enzyme.

Because of the introduction of a Nco I site at the initiation methionine of the gene, the nucleotide sequence was slightly changed:

Original sequence:
5' TAA AGG ATG AAA AAA ACC GTT GTG ATT GGC 3'
(SEQ ID NO:53)
MET Lys Lys Thr Val Val Ile Gly
(SEQ ID NO:54)

New Genetically Engineered Sequence:
    Nco I
5' TAA ACC ATG GAA AAA ACC GTT GTG ATT GGC 3'
(SEQ ID NO:55)
MET Glu Lys Thr Val Val Ile Gly
(SEQ ID NO:56)

The sequence at the 3' end of the gene was not changed as a result of the PCR reaction.

g. Phytoene Dehydrogenase-4H Assay

The assay for phytoene dehydrogenase-4H was developed using two R- sphaeroides mutants, I-3 and E-7. I-3, a mutant strain that has a mutation in the gene for phytoene dehydrogenase-3H, was provided by Dr. Samuel Kaplan, University of Texas Medical Center, Houston, Tex. This mutant, which accumulates phytoene, was used as a source of the substrate for phytoene dehydrogenase-3H and phytoene dehydrogenase-4H.

*R. sphaeroides* E-7 is a strain that cannot make any carotenoids, and was developed at the Amoco Research Center, Naperville, Ill. This mutant, which has an intact gene for a different, but similar phytoene dehydrogenase-3H, provided a source of the similar enzyme to determine the proper assay conditions.

The membrane fraction from the Rhodobacter I-3 mutant was isolated by growing I-3 cells until mid to late log phase, pelleting and lysing the harvested cells in 100 mM Tris Buffer, pH 8.0, by vortexing with 150 micron acid-washed glass beads. The cell homogenate was then used as the source of phytoene.

Although the *R. sphaeroides* E-7 phytoene dehydrogenase-3H transforms phytoene to either phytofluene or neurosporene but not to lycopene, as in *Erwinia herbicola*, the assay conditions delineated for the Rhodobacter enzyme were also efficacious for the *Erwinia herbicola* phytoene dehydrogenase-4H. These conditions were used to detect phytoene dehydrogenase-4H activity in both *E. coli* and *S. cerevisiae* harboring the *Erwinia herbicola* structural gene for phytoene dehydrogenase-4H, as is discussed below.

To isolate the phytoene dehydrogenase-4H from either bacteria or yeast harboring the *Erwinia herbicola* gene, cells were grown until mid-late log phase and harvested by pelleting. The cell pellet was either frozen for later use or used immediately. A frozen or fresh cell pellet was resuspended in one volume of 100 mM Tris Buffer, pH 8.0, and lysed by vortexing as described above for Rhodobacter (150 micron beads were used to lyse bacteria and 450 micron beads were used to lyse yeast). This cell lysate provided a source of phytoene dehydrogenase-4H for testing.

An aliquot of the *Erwinia herbicola* phytoene dehydrogenase-4H-containing lysate was admixed with an aliquot of the Rhodobacter I-3 cell lysate described above in a buffer containing 100 mM Tris, pH 8.0, 10 mM ATP, 2.5 mM NADP, 4 mM DTT, 4 mM $MgCl_2$, 6mM $MnCl_2$ in a total volume of 1–2 ml. The reaction mixture was incubated at 30° C. in the dark for 2–8 hours, and the contents were extracted first with hexane and then with chloroform. The organic layers were pooled, dried, and analyzed by HPLC on a C-18 analytical column (4.6×250 mm) developed with a linear gradient, starting with 30 percent isopropyl alcohol and 70 percent acetonitrile:water (9:1) and ending with 55 percent isopropyl alcohol and 45 percent acetonitrile:water (9:1), in 30 minutes at a flow rate of 1 ml/minute. Lycopene, which eluted at about 16.2 minutes, was quantitated from a predetermined standard curve.

EXAMPLE 11

Lycopene Production in *E. coli* a. Method One—Plasmid(s) containing the engineered genes for GGPP synthase, phytoene synthase and phytoene dehydrogenase Active GGPP synthase, phytoene synthase, and phytoene dehydrogenase-4H enzymes can convert ubiquitous cellular precursors into lycopene. Lycopene was produced in *E. coli* when plasmids containing the three genes for the above enzymes were introduced into the bacterial host cells. One combination producing lycopene utilized host cells transformed with the plasmids pARC275 and pARC496A.

The plasmid pARC275 was constructed in the following manner. First, the plasmid pARC376-Pst 110 was made by deleting the about 2999 bp Pst I segment (between positions 7792 and 10791, FIG. 5) from pARC376 as described before. Second, the Eco RI (3370) to Hind III (13463 FIG. 5) segment from plasmid pARC376-Pst110 was excised and cloned into the Eco RI to Hind III sites of plasmid pSOC925 to produce plasmid pARC275.

The plasmid pSOC925 is about a 9 kilobase plasmid whose restriction map is illustrated in FIG. 12. This plasmid contains the kanamycin and chloramphenicol (CAT) resistance genes and the R1162 origin of replication. The chloramphenicol resistance gene can be excised from the plasmid by digestion with Eco RI and Hind III (FIG. 12).

The fragment (Eco RI to Hind III of plasmid pARC376-Pst 110) containing the relevant portion of the *Erwinia herbicola* carotenoid genes was isolated. Plaesmid pSOC925 was digested with Eco RI and Hind III, excising the CAT gene. About 100 ng of the larger portion of digested plasmid pSOC925 was admixed with about 200 ng of the Eco RI to Hind III fragment from plasmid pARC376-Pst 110 in a total volume of 20 µl to which 2 µl of Ligation Buffer and 1 Unit of T4 Ligase were added. The ligation mixture was incubated at 4° C. for about 15 hours and then transformed into *E. coli* HB101 cells. Transformants were grown in Luria-Broth supplemented with 25 µg/ml of kanamycin. DNA was isolated from prospective clones and those clones containing the desired DNA insert were identified by restriction analysis. The resultant pARC275 plasmid confers the ability to produce phytoene on *E. coli*.

Transformation of *E. coli* host cells with plasmids pARC275 and pARC496A produced red colonies of the transformed host cells, as is discussed in Example 10.

b. Method Two—Plasmid with a defective gene for lycopene cyclase

Following production of lycopene, the next step in the *Erwinia herbicola* biosynthetic pathway is the transformation of lycopene to beta-carotene by lycopene cyclase. When the gene encoding lycopene cyclase is inhibited, mutated, or in some other manner made non-functional, the enzyme lycopene cyclase, which transforms lycopene to beta-carotene, does not function. Lycopene accumulates when this occurs.

The plasmid pARC376-Ava 102, a derivative of plasmid pARC376 in which the gene for lycopene cyclase has been deleted, was constructed by partially digesting plasmid pARC376 with Ava I to remove two adjacent, relatively short Ava I-Ava I fragments and religating the cut ends of the remaining, relatively large fragment. The two relatively small Ava I-Ava I fragments included the about 1611 bp Ava I fragment (10453–8842 FIG. 5) and the about 611 bp Ava I-Ava I fragment from (8842–8231 FIG. 5). In total, about 2222 bp of DNA were deleted from the plasmid pARC376.

The resulting plasmid pARC376-Ava 102 was transformed into *E. coli* HB101, and the transformants were grown on Luria-Broth with 100 µg/ml of ampicillin. Normally, *E. coli* cells that contain the entire plasmid pARC376 are yellow due to the production of zeaxanthin and zeaxanthin derivatives. Following transformation, some of the clones were now red in color.

Plasmid DNA was isolated from one of these red *E. coli* clones and subjected to restriction analysis, which revealed that the two Ava I-Ava I fragments had been deleted from the original pARC376 plasmid. This deletion of the Ava I fragments from plasmid pARC376 impaired the gene for lycopene cyclase.

Under this circumstance, the three genes for GGPP synthase, phytoene synthase, and phytoene dehydrogenase-4H on plasmid pARC376-Ava 102 functioned properly and produced lycopene. Because the gene for lycopene cyclase did not function properly, the transformed *E. coli* host cells accumulated lycopene.

EXAMPLE 12

Lycopene Production in *S. cerevisiae*

Normal yeast cells do not produce lycopene. Genes sufficient to make lycopene in *S. cerevisiae* include those for GGPP synthase, phytoene synthase, and phytoene dehydrogenase-4H. The plasmid pARC145G (Example 6) has the genes for GGPP synthase and phytoene synthase on both sides and adjacent to the GAL 10 and GAL 1 divergent promoter region. Both of these genes are expressed in *S. cerevisiae* using these two promoters.

The gene for phytoene dehydrogenase-4H is located on the plasmid pARC146D described hereinafter. These two plasmids were transformed into *S. cerevisiae*, strain YPH499.

The yeast strain YPH499 contains a non-functional TRP 1 gene and a non-functional URA 3 gene (as discussed in Example 6). Plasmid pARC145G contains a functioning TRP 1 gene as well as the genes for GGPP synthase and phytoene synthase. Plasmid pARC146D contains a functioning URA 3 gene as well as the gene for phytoene dehydrogenase-4H. After both plasmids were introduced, the yeast cells were grown on Medium 4 (Example 6) with galactose to induce the expression of the three carotenoid genes.

The cells were grown to stationary phase, collected, extracted, and analyzed by HPLC according to the protocols described before. Yeast cells with the three carotenoid structural genes produced lycopene at about 0.01 percent dry weight.

a. Construction of Plasmid pARC146

The plasmid pARC146 is a *S. cerevisiae* vector constructed to direct the expression of the phytoene dehydrogenase-4H gene in yeast.

The construction of plasmid pARC145B (FIG. 9) was outlined before in Example 6 for production of phytoene. Two modifications were made to plasmid pARC145B in order to construct plasmid pARC146.

The first modification was the introduction of the PGK terminator at the Sph I site of pARC145B, downstream from the GAL 1 promoter. A polycloning site, into which a structural gene could be cloned, is present between the GALI promoter and the PGK terminator.

Thus, an about 500 bp Eco RI-Hind III fragment containing the *S. cerevisiae* PGK terminator was excised from plasmid pARC117 (Example 6). This is substantially the same PGK terminator fragment discussed in Example 6 and shown in FIG. 7 for plasmid pARC135. The Eco RI and Hind III ends of this fragment were blunted by treatment with the Klenow fragment of DNA Polymerase. Synthetic double-stranded sequences each containing a potential Sph I cleavage site (BRL) were then ligated to both ends of the PGK terminator fragment, and that fragment was digested with Sph I, producing sticky ends. Plasmid pARC145B was digested with Sph I, and the Sph I-linked PGK terminator was ligated to form the resulting plasmid pARC145C.

The second modification was to replace the yeast TRP 1 gene with the yeast URA 3 gene. This enabled transfer of the plasmid into yeast cells that had a mutation in the URA 3 gene on the yeast chromosome. Here, the plasmid pARC145C was digested with restriction enzymes Msc I and Eco RV, and a 737 bp fragment containing the TRP 1 gene was deleted.

Synthetic double-stranded sequences containing a potential Xho I cleavage site (BRL) were ligated to the Msc I and Eco RV blunt ends (there are no other Xho I sites in plasmid pARC145). The resulting DNA fragment was digested with Xho I to produce a-DNA having Xho I sticky ends.

Meanwhile, an about 1000 bp Hind III fragment, including the entire URA 3 gene, was excised from the plasmid YEp24 (ATCC 37051). The ends of this fragment were blunted with the Klenow fragment of DNA Polymerase. Synthetic double-stranded sequences, each containing a potential Xho I cleavage site were ligated to the blunt ends. This fragment was then digested with Xho I, producing sticky ends.

This URA 3 gene fragment was then ligated into the Xho I-digested pARC145C plasmid (from which the TRP 1 gene had been deleted). The final plasmid was named pARC146 and is similar to plasmid pARC145C except that plasmid pARC146 contains a URA 3 selectable marker instead of a TRP 1 gene.

Unexpectedly, plasmid pARC146 did not contain two Xho I sites. The Xho I site expected at the location of the Eco RV site of the original vector, denoted as (Xho I) in FIG. 13, could not be digested. However, the apparent loss of the site did not effect the utility of plasmid pARC146 as aURA 3 selectable vector and also did not effect the utility of plasmid pARC146 as an expression vector.

The relevant features of this new plasmid construct are i) the presence of the divergent GAL 1 and GAL 10 promoters, ii) the PGK terminator at the 3' end of the GAL 1 promoter, iii) the 2 micron STB terminator (2 MIC STB TERM) at the 3' end of the GAL 10 promoter, iv) the URA 3 gene that is the selectable marker for transferring the plasmid into *S. cerevisiae*, and v) the 2 micron origin of replication that permits the maintenance of the plasmid in yeast. This plasmid also contains the pMB1 origin of replication for maintenance in *E. coli* and the ampicillin resistance gene for selection in *E. coli*. A restriction map of the plasmid pARC146 is shown in FIG. 13.

b. Construction of pARC496B

Plasmid pARC496B was constructed to introduce a Sal I site immediately upstream from the initiation methionine of the phytoene dehydrogenase-4H structural gene and a Sal I site at the 3' end of the gene to enable the gene for phytoene dehydrogenase-4H to be moved as a Sal I-Sal I fragment. This version of the gene was used as the structural gene for phytoene dehydrogenase-4H in constructing the plasmid pARC146D (described below) that was transformed into *S. cerevisiae* in combination with transformation with plasmid pARC145G to cause the production of lycopene in the transformed yeast. The plasmid pARC496B was constructed using the PCR protocol described before (plasmid pARC496A) to introduce Sal I sites at the 5' and 3' ends of the gene.

i. Template DNA for the PCR

The plasmid pARC271D (Example 10) was digested with Sal I and Xmn I and an about 3.035 bp fragment (9340–6305, FIG. 5) was isolated after separation on agarose gel electrophoresis. This fragment was used as the template for PCR.

ii. Probes for the PCR

Two oligonucleotide probes were used to introduce Sal I sites at the 5' and the 3' ends of the gene for phytoene dehydrogenase-4H. At the 5' end of the gene, the newly introduced Sal I site was immediately upstream from the initiation methionine. At the 3' end of the gene, the newly introduced Sal I site was immediately upstream from the Nco I site at 6342.

The original sequence of the 5' end was:

5' G AGA TAA AGG ATG AAA AAA ACC GTT GTG AT 3'
                    MET ...
(SEQ ID NO:57)

The oligonucleotide probe for the 5' end was:

Sal I
5' G AGG TCG ACG ATG AAA AAA ACC GTT GTG AT 3'
                    MET ...        (SEQ ID NO:58), in which the altered bases are shown in bold face.

The second strand oligonucleotide probe for the 3' end of the gene was:

Sal I
5' AT GGT CGA CGT GGC GTG GTC AAG CAG CGG 3'
(SEQ ID NO:59)

The polymerass chain reaction was carried out as described before. After completion, the reaction mixture was extracted twice with ether and the DNA was precipitated with ethanol.

iii. Cloning of the PCR Produced DNA Fragment The DNA accumulated from the PCR was digested with Sal I, producing an about 1508 bp fragment (from the "T" of the TCGAC overhang at the 5' end of the gene to the "G" of the Sal I site at the 3' end of the gene). Five µg of the plasmid pARC306A (FIG. 6) was digested with Sal I. About 100 ng of the Sal I-digested pARC306A and about 200 ng of the Sal I-Sal I fragment of the phytoene dehydrogenase-4H structural gene prepared by PCR were admixed with 2 µl of Ligation Buffer (IBI) and 1 Unit of T4 Ligase in a total volume of 20 µl. The ligation reaction mixture was incubated at 4° C. for about 15 hours.

The resulting plasmid was transformed into *E. coli* HB101, and the transformants were selected by growth in Luria-Broth supplemented with 100 µg/ml of ampicillin. DNA from prospective clones was isolated and the identity of clones containing the phytoene dehydrogenase-4H gene was confirmed by restriction enzyme analysis.

The resultant plasmid was named pARC496B. The about 1508 bp Sal I-Sal I fragment (also referred to as a Sal I fragment), another particularly preferred DNA segment, was cloned from plasmid pARC496B into the yeast vector pARC146, to generate the plasmid pARC146D as described hereinafter.

iv. Sequence of the Phytoene Dehydrogenase-4H Gene Fragment of Plasmid pARC496B

The introduction of the Sal I sites at the 5' and 3' ends of the gene for phytoene dehydrogenase-4H changed the nucleotide sequence of the native DNA fragment slightly.

Original sequence at the 5' end of the gene:

(SEQ ID NO:60)
5' GAG ATA AAG G ATG AAA AAA ACC GTT GTG AT 3'
             MET Lys Lys Thr Val Val ...
(SEQ ID NO:61)

Sequence of the genetically engineered versions of the gene at the 5' end:

```
                    Nco I                (SEQ ID NO:62)
        5' CC ATG GAA AAA ACC GTT GTG AT 3'
              MET Glu Lys Thr Val Val
                                         (SEQ ID NO:63)

Sal I                (SEQ ID NO:64)
        5' GAG GTC GAC G ATG AAA AAA ACC GTT GTG AT 3'
                      MET Lys Lys Thr Val Val ...
                                         (SEQ ID NO:65)
```

Original sequence at the 3' end of the gene:

```
                              Nco I (6342)
        5' CC GCT GCT TGA CCA CGC CAC GCA GAC CAT GG 3'
                                         (SEQ ID NO:66)
```

After the introduction of the Sal I site from the PCR reaction the new sequence became:

```
                         Sal I    Nco I (6342)
        5' CC GCT GCT TGA CCA CGC CAC GTC GAC CAT GG 3'
                                         (SEQ ID NO:67)
```

Altered bases in the above sequences are shown in bold face.

c. Construction of the Plasmid pARC146D

An about 1508 bp Sal I fragment described above containing the structural gene for phytoene dehydrogenase-4H was excised from plasmid pARC496B and was ligated into the Sal I site of the pARC146 plasmid described before. The result was the plasmid pARC146D construct, placing the gene for phytoene dehydrogenase-4H between and adjacent to the GAL1 promoter and the PGK terminator. A restriction map of the pARC146D plasmid is illustrated in FIG. 14, in which the location of the phytoene dehydrogenase-4H gene is shown as "PDH".

EXAMPLE 13

Expression of Erwinia herbicola Phytoene Dehydrogenase-4H Gene in Rhodobacter sphaeroides This Example describes the construction of a plasmid, pATC228, that was transformed into a mutant strain of *R. sphaeroides*, causing the expression of *Erwinia herbicola* phytoene dehydrogenase-4H in that organism. Plasmid vector pATC228 was made by combining the plasmid pATC1619, which contains a genetically engineered phytoene dehydrogenase-4H structural gene, with plasmid pSOC244, which is capable of transforming and being maintained in both *E. coli* and *R. sphaeroides*. The following is a description of the multistep construction of plasmid pATC228.

a. Construction of Plasmid pATC1619

The plasmid pATC1619 contains a genetically engineered version of the phytoene dehydrogenase-4H gene cloned adjacent to the TAC promoter of pDR540 (Pharmacia). The gene for phytoene dehydrogenase-4H is expressed in *E. coli* and photosynthetic bacteria using the TAC promoter. Plasmid pATC1619 was constructed in a multistep procedure requiring several intermediate plasmids as outlined below.

i. Plasmid pARCBglII401

The plasmid pARCBglII401 was constructed by cloning the about 5513 bp Bgl II fragment from plasmid pARC376 (from position 6836 to position 12349 in FIG. 5) into the Bam HI site of plasmid pARC306A (FIG. 6).

ii. Plasmid pATC1403

An about 1548 bp Pst I to Sal I fragment from plasmid pARCBglII401 (original coordinates in FIG. 5 were 7792 and 9340, respectively) was cloned into the Pst I and Sal I sites of plasmid M13mp19 (BRL) to generate plasmid pATC1403. Plasmid pATC1403 contains a beginning portion of the phytoene dehydrogenase-4H gene.

iii. Plasmid pATC1404

A Sph I site was introduced at the initiation Met codon of the phytoene dehydrogenase-4H gene in plasmid pATC1403, using the in vitro mutagenesis protocol described in *Current Protocols in Molecular Biology*, Ausabel et al. eds., John Wiley & Sons, New York (1987), pp. 8.1.1–8.1.6 (see Example 2). The oligonucleotide probe used as the primer was:

```
                    Sph I                (SEQ ID NO:68)
        5' G ACG AGA TAA AGC ATG CAA AAA ACC GTT GT 3'
                      MET Gln Lys Thr Val ...
                                         (SEQ ID NO:69)
```

The sequence in the native phytoene dehydrogenase-4H gene was:

```
                                         (SEQ ID NO:70)
        5' G ACG AGA TAA AGG ATG AAA AAA ACC GTT GT 3'
                      MET Lys Lys Thr Val ...
                                         (SEQ ID NO:71)
```

As a result of the introduction of the Sph I site, the second amino acid of the phytoene dehydrogenase-4H enzyme was changed from Lys to Gln. Thus, the new sequence became:

```
                    Sph I                (SEQ ID NO:72)
        5' G ACG AGA TAA AGC ATG CAA AAA ACC GTT GT 3'
                      MET Gln Lys Thr Val
                                         (SEQ ID NO:73)
```

This plasmid, with the Sph I site at the initiation methionine codon of the phytoene dehydrogenase-4H structural gene, was named pATC1404. Altered bases are shown in bold face in the above sequences.

iv. Plasmid pATC816

The plasmid, pARC306A (FIG. 6) was digested with Pst I and Sma I. The plasmid pARC376 (FIG. 5) was digested with Pst I and Bal I. An about 1451 bp Pst I (7792) to Bal I (6341) fragment was isolated from an agarose gel. Both Bal I and Sma I digestions leave a blunt end. The approximately 1451 bp Pst I-Bal I fragment from plasmid pARC376 was cloned into the Pst I and Sma I digested pARC306A to form plasmid pATC816.

Plasmid pARC306A contains an Eco RI site about 30 bp downstream from the Sma I site. The Eco RI site originally present in plasmid pARC306A is maintained in plasmid pATC816.

v. Plasmid pATC1605

As previously stated, the plasmid pATC1404 contains only the beginning portion of the gene encoding phytoene dehydrogenase-4H. To fuse this portion with the remainder of the phytoene dehydrogenase-4H gene, an about 1052 bp Sma I to Pst I fragment from plasmid pATC1404 (original position 8844 to 7792 of plasmid pARC376 in FIG. 5) was excised and cloned into plasmid pATC816 (which contains the 3' portion of the phytoene dehydrogenase-4H gene) as follows.

Plasmid pATC816 was digested with Ssp I and Pst I (both sites are unique in the pATC816 plasmid). Digestion with Ssp I left a blunt end. The Sma I to Pst I fragment from plasmid pATC1404 was cloned into the digested plasmid pATC816, resulting in plasmid pATC1605. This cloning procedure completed the sequence of the phytoene dehydrogenase-4H gene. There is a superfluous DNA segment immediately upstream from the initiation codon of the phytoene dehydrogenase-4H gene.

In addition, the newly created Sph I site of plasmid pATC1404 containing the codon for the initial Met residue of the enzyme became a part of the phytoene dehydrogenase-4H structural gene. The originally present Nco I site shown near the 3' end of the sequence of FIG. 11-4 is also present in this construct as is the Eco RI site downstream therefrom that was introduced from plasmid pARC306A. The Sph I-Eco RI fragment of plasmid pATC1605 that contains the structural gene for phytoene dehydrogenase-4H contains about 1550 bp.

vi. Plasmid pATC1607

Plasmid pATC1605 was digested with Sph I and Eco RI enzymes. The resultant fragment of about 1550 bp was cloned into the plasmid pUC19 (Pharmacia), which had been digested with Sph I and Eco RI enzymes, resulting in the plasmid, pATC1607.

vii. Plasmid pATC1619

Upstream and adjacent to the Sph I site on plasmid pATC1607 is a Hind III site that originates from the polylinker region of plasmid pUC19. The structural gene for phytoene dehydrogenase-4H was excised from plasmid pATC1607 by digesting with Hind III and Eco RI. The ends of the resultant fragment, also of about 1550 bp, were blunted by treating with the Klenow fragment of *E. coli* DNA Polymerass.

The plasmid pDR540 (Pharmacia), which contains the TAC promoter for gene expression in some bacteria, including *E. coli* and *R. sphaeroides*, and a unique Bam HI site downstream of the TAC promoter, was digested with Bam HI, and the ends were blunted as above. The blunt ended DNA fragment from plasmid pATC1607 (above) was cloned into plasmid pDR540, resulting in the plasmid pATC1619, which contained the bacterial TAC promoter adjacent to the structural gene for phytoene dehydrogenase-4H. Plasmid pATC1619 also contains a unique Hind III site.

b. Construction of Plasmid pATC228

Plasmid pSOC244 is a plasmid that contains i) the R1162 origin of replication, ii) the chloramphenicol acetyltransferase gene that confers resistance to chloramphenicol adjacent to the TAC promoter, and iii) a unique Hind III site. This plasmid can transform and be maintained in both *E. coli* and *R. sphaeroides*. The construction of plasmid pSOC244 is discussed below.

i. plasmid pSOC200

Plasmid pQR176a was obtained from Dr. J. A. Shapiro of the University of Chicago, Chicago, Ill., and is described in Meyer et al., *J. Bacteriol.*, 152:140 (1982). This plasmid contains the R1162 origin of replication and the transposon Tn5, which confers resistance to kanamycin. This plasmid contains about 14.5 kilobases and contains several Hind II restriction sites.

Digestion of plasmid pQR176a with Hind II, followed by religation of appropriate fragments provided plasmid pSOC200, which contained about 8.5 kilobases. This plasmid retained the R1162 origin of replication and the kanamycin resistance gene from Tn5.

ii. Plasmid pSOC244

Plasmid pSOC200 was digested with Hind III and Sma I endonucleases to remove the kanamycin resistance gene. Plasmid pSOC925 was similarly digested to provide an approximately 1000 bp fragment containing the chloramphenicol acetyltransferase (CAT) structural gene with the adjacent TAC promoter. That approximately 1000 bp fragment was then cloned into the Hind III- and Sma I-digested plasmid pSOC200 fragment to provide plasmid pSOC244.

iii. Plasmid pATC228

Both plasmids, pATC1619 and pSOC244, were digested with Hind III. The two plasmids were ligated together and selected in *E. coli* grown in medium containing ampicillin (using the ampicillin resistance gene from the pATC1619 plasmid) and chloramphenicol (using the chloramphenicol resistance gene from the pSOC244 plasmid). The resultant plasmid was pATC228, which contains the structural gene for phytoene dehydrogenase-4H and can transform and be maintained in *R. sphaeroides*. This structural gene can be excised from plasmid pATC228 as an approximately 1506 bp Sph I-Nco I restriction fragment. Plasmid pATC228 is shown schematically in FIG. 16.

c. Expression of the Erwinia herbicola Phytoene Dehydrogenase-4H Gene in a *R. sphaeroides* I-3 Mutant The *R. sphaeroides* I-3 mutant (utilized in Example 10g), possesses an impaired native crtI gene for phytoene dehydrogenase-3H, and thus accumulates phytoene. Cells from *R. Sphaeroides* I-3 were transformed as hosts with plasmid pATC228. The transformants were selected in the presence of chloramphenicol. The mutant cells that were previously colorless, were colored red after transformation. The red pigment produced by these cells had physicochemical characteristics that were consistent with the properties of the carotenoid spirilloxanthin.

The red pigment produced by the plasmid pATC228-transformed *R. sphaeroides* I-3 mutant host cells was compared to authentic spirilloxanthin extracted from *R. rubrum* (ATCC 25903) cells grown in culture. The two pigments had the same UV-V is spectra and the same HPLC profiles. The red pigment produced by the transformed cells was not positively identified as spirilloxanthin and is therefore referred to as a spirilloxanthin-like carotenoid. Spirilloxanthin from *R. rubrum* is derived from lycopene through a series of catalytic steps that include two dehydrogenations, hydration, and then methylation. The photosynthetic Bacteria, Roderick et al. eds., Plenum Press, New York, pages 729–750 (1978).

*R. sphaeroides* normally transforms phytoene to neurosporene, not to lycopene. It is believed, therefore, that in the production of the spirilloxanthin-like pigment in the transformed *R. sphaeroides*, the *Erwinia herbicola* phytoene dehydrogenase-4H catalyzed desaturation of accumulated phytoene to produce lycopene. The produced lycopene was thereafter further metabolized by native enzymes present in the *R. sphaeroides* mutant to form spirilloxanthin-like carotenoid.

EXAMPLE 14

Lycopene Production in *Pichia pastoris*

The above-described method is also extendable to other yeasts. One yeast system that serves as an example is the methylotrophic yeast, *Pichia pastoris*.

To produce lycopene in *P. pastoris*, structural genes for GGPP synthase, phytoene synthase, and phytoene dehydrogenase-4H are placed under the control of regulatory sequences that direct expression of structural genes in Pichia. The resultant expression-competent forms of those genes are introduced into Pichia cells.

For example, the transformation and expression system described by Cregg et al., *Biotechnology* 5:479–485 (1987); *Molecular and Cellular Biology* 12:3376–3385 (1987) can be used. A structural gene for GGPP synthase such as that from plasmid pARC489D is placed downstream from the alcohol oxidase gene (AOX1) promoter and upstream from the transcription terminator sequence of the same AOX1 gene. Similarly, structural genes for phytoene synthase and phytoene dehydrogenase-4H such as those from plasmids pARC140N and pARC146D are placed between AOX1 promoters and terminators. All three of these genes and their flanking regulatory regions are then introduced into a plasmid that carries both the *P. pastoris* HIS4. gene and a *P. pastoris* ARS sequence (Autonomously Replicating Sequence), which permit plasmid replication within *P. pastoris* cells [Cregg et al., *Molecular and Cellular Biology*, 12:3376–3385 (1987)].

The vector also contains appropriate portions of a plasmid such as pBR322 to permit growth of the plasmid in *E. coli* cells. The final resultant plasmid carrying GGPP synthase, phytoene synthase, and phytoene dehydrogenase-4H genes, as well as the various additional elements described above, is illustratively transformed into a his4 mutant of *P. pastoris*, i.e. cells of a strain lacking a functional histidinol dehydrogenase gene.

After selecting transformant colonies on media lacking histidine, cells are grown on media lacking histidine, but containing methanol as described by Cregg et al., *Molecular and Cellular Biology*, 12:3376–3385 (1987), to induce the AOX1 promoters. The induced AOX1 promoters cause expression of the enzymes GGPP synthase, phytoene synthase, and phytoene dehydrogenase-4H and the production of lycopene in *P. pastoris*.

The three genes for GGPP synthase, phytoene synthase, and phytoene dehydrogenase-4H can also be introduced by integrative transformation, which does not require the use of an ARS sequence, as described by Cregg et al., *Molecular and Cellular Biology*, 12:3376–3385 (1987).

EXAMPLE 15

Lycopene Production in *A. nidulans*

The genes encoding GGPP synthase, phytoene synthase, and phytoene dehydrogenase-4H as discussed before can be used to synthesize and accumulate lycopene in fungi such as *Aspergillus nidulans*. Genes are transferred to Aspergillus by integration.

For example, the structural gene for GGPP synthase is introduced into the *E. coli* plasmid pBR322. The promoter from a cloned Aspergillus gene such as argB [Upshall et al., *Mol. Gen. Genet.* 204:349–354 (1986)] is placed into the plasmid adjacent to the GGPP synthase structural gene. Thus, the GGPP synthase gene is now under the control of the Aspergillus argB promoter.

Next, the entire cloned amds gene [Corrick et al., *Gene* 53:63–71 (1987)] is introduced into the plasmid. The presence of the amds gene permits acetamide to be used as a sole carbon or nitrogen source, thus providing a means for selecting those Aspergillus cells that have become stably transformed with the amds-containing plasmid.

Thus, the plasmid so prepared contains the Aspergillus argB promoter fused to the GGPP synthase gene and the amds gene present for selection of Aspergillus transformants. Aspergillus is then transformed with this plasmid according to the method of Ballance et al., *Biochem. Biophys. Res. Commun.* 112:284–289 (1983).

The phytoene synthase and phytoene dehydrogenase-4H structural genes are each similarly introduced into the *E. coli* plasmid pBR322. Promoters for the cloned Aspergillus argB gene [Upshall et al., *Mol. Gen. Genet*, 204:349–354 (1986)] are placed immediately adjacent to the phytoene synthase and phytoene dehydrogenase-4H structural genes. Thus, these structural genes are controlled by the Aspergillus argB promoters.

The entire, cloned Aspergillus trpC gene [Hamer and Timberlake, *Mol. Cell. Biol.*, 7:2352–2359 (1987)] is introduced into the plasmid. The trpC gene permits selection of the integrated plasmid by virtue of permitting transformed trpC mutant Aspergillus cells Go now grow in the absence of tryptophan. The Aspergillus strain, already transformed with the plasmid containing the GGPP synthase gene, is now capable of synthesizing lycopene.

EXAMPLE 16

Phytoene Dehydrogenase-4H in Higher Plants

Higher plants have the genes encoding the enzymes required for lycopene production and so inherently have the ability to produce lycopene. Lycopene normally is not accumulated, however, because lycopene so produced in most plants is further converted to other products. Even in the case of ripe tomato fruits, the level of lycopene accumulated is only about 0.01 percent dry weight. The carotenoid-specific genes from *Erwinia herbicola* can be used to express phytoene dehydrogenase-4H for use by the plant as well as to improve accumulation of lycopene in plants. Two useful approaches are described below.

a. Transport to the Chloroplast

In the first approach, the gene for phytoene dehydrogenase-4H was modified to introduce the restriction site Sph I at the initiation methionine codon, as discussed before. An about 177 bp DNA fragment that encodes for the transit (signal) peptide of the tobacco gene for ribulose bis-phosphate carboxylase-oxygenase containing a Nco I site at the 5' end and a Sph I site at the 3' end, was ligated to the Sph I site of the structural phytoene dehydrogenase-4H gene. This modified gene was inserted into the plasmid pCaMVCN (Pharmacia, Piscataway, N.J.) replacing the CAT gene. The resultant plasmid contained a gene for phytoene dehydrogenase-4H with the transit peptide sequence placed between and adjacent to both the CaMV 35S plant promoter and the NOS polyadenylation sequence at the 3' end.

This phytoene dehydrogenase-4H gene construct was inserted into the plasmid pGA482 (Pharmacia) in a convenient restriction site within the multiple cloning linker region to form plasmid pATC1616. The relevant features of plasmid pGA482 include (i) an origin of replication that permits maintenance of the plasmid in *Agrobacterium tumefaciens*, (ii) the left and right border sequences from the T-DNA region that direct the integration of the DNA segment between the borders into the plant genome, and (iii) the NOS promoter adjacent to the kanamycin resistance gene that permits plant cells to survive in the presence of kanamycin.

This phytoene dehydrogenase-4H gene construct was transformed into *Agrobacterium tumefaciens* LBA4404

(Clontech, Inc.) according to standard protocols. Agrobacterium cells containing the plasmid with the phytoene dehydrogenase-4H gene construct were transferred by infection of tobacco leaf discs using the method of Horsch et al., Science, 227:1229–1231 (1985). During the infection process, the entire DNA segment between the left and right borders of the pGA482 plasmid was transfected into the plant cells. Transfected plant cells are selected for kanamycin resistance.

Transgenic tobacco plants were grown in the presence of the herbicide norflurazon (Sandoz). Control plants that had been transformed with the control plasmid pGA482 and that did not contain Erwinia herbicola phytoene dehydrogenase-4H structural gene bleached when grown in the presence of 0.2 µg/ml norflurazon in the growth medium. Transgenic plants containing the Erwinia herbicola phytoene dehydrogenase-4H structural gene grew normally in the presence of 0.8 µg/ml of norflurazon. Thus, the introduction of the Erwinia herbicola phytoene dehydrogenase-4H structural gene caused the expression of Erwinia herbicola phytoene dehydrogenase-4H, and plants to become resistant to a herbicidal amount of norflurazon.

The specific DNA segments, recombinant molecules and techniques utilized in the preparation of the above norflurazon-resistant tobacco plants are discussed below.

i. Transit Peptide

The construction and sequence of the transit peptide DNA is discussed in Example 3.

ii. Plasmid pATC212

The construction of pasmid pATC212 is discussed in Example 3.

iii. Plasmid pATC1616

Plasmid pATC1616 is a derivative of plasmid pGA482 that contains the gene for phytoene dehydrogenase-4H with the transit peptide sequence in frame with the coding sequence of the phytoene dehydrogenase-4H gene. This gene construct is driven by the CaMV 35S promoter and contains the NOS polyadenylation site downstream of the structural gene. The plasmid was made in the following way.

The plasmid pATC1607 (Example 13) contains a version of the phytoene dehydrogenase-4H with a Sph I site at the initiation methionine codon. Plasmid pATC1607 was digested with Nco I. The cleaved Nco I site is the same as the Nco I site at about position 6342 in FIG. 5 and is the Nco I site at about position 1510 in FIG. 11. The Nco I site was made blunt by treating with the Klenow fragment of DNA polymerase.

The thus treated pATC1607 plasmid was then digested with Sph I. This digestion caused the production of an about 1506 bp fragment, which includes the structural gene for phytoene dehydrogenase-4H. At the 5' end of the fragment is a Sph I site and at the 3' end of the fragment is a blunt end.

Plasmid pATC212 was digested with Sph I and Sma I. The Sph I site is at the 3' end of the transit peptide sequence and the Sma I site is downstream in the polylinker sequence of the plasmid pATC212. The above Sph I-blunt ended phytoene dehydrogenase-4H gene fragment was cloned into the pATC212 plasmid, resulting in plasmid pATC1612.

Plasmid pATC1612 contains the CaMV 35S promoter, the transit peptide sequence, the structural phytoene dehydrogenase-4H gene, and the NOS polyadenylation sequence. This whole region of plasmid pATC1612 can be moved as an Xba I-Xba I fragment, since there are Xba I sites upstream from the CaMV 35S promoter and downstream from the NOS polyadenylation sequence.

Plasmid pATC1612 was digested with Xba I and the about 2450 bp Xba I-Xba I fragment (450 bp CaMV 35S promoter, 177 bp transit peptide sequence, 1506 bp phytoene dehydrogenase-4H gene, and the 300 bp NOS polyadenylation sequence) was cloned into the Xba I site of plasmid pGA482. The resulting plasmid is pATC1616.

b. Production in the Plant Cytoplasm

To prepare lycopene in the cytoplasm, the carotenoid genes described before are introduced into appropriate vector(s), as also described above for chloroplasts, using identical techniques, except that the transit peptide is eliminated. Because they are not targeted to the chloroplast, the enzymes remain in the cytoplasm, and, acting on the ubiquitous isoprenoid intermediate, farnesyl pyrophosphate, produce lycopene in the cytosol.

EXAMPLE 17

Lycopene Cyclase Gene a. Localization

The location of the lycopene cyclase gene on pARC376 was established as described before for the other enzyme genes. If the gene for lycopene cyclase were deleted, mutated or otherwise impaired, there would not be an active lycopene cyclase enzyme and lycopene would accumulate. Lycopene imparts a red color to E. coli cells producing it, whereas beta-carotene imparts a yellow color to E. coli cells producing beta-carotene.

The following experiments demonstrated that the gene is located on a 1548 bp DNA fragment of plasmid pARC376 bounded by the Sal I site (9340) and the Pst I site (7792) shown in FIG. 5.

Plasmid pARC376 was partially digested with Ava I, the ends were religated, and the plasmid DNA was transformed into E. coli strain HB101 cells. This plasmid, named pARC376-Ava 102, contained a 611 bp Ava I fragment deletion from position 8231 to 8842 and also a 1611 bp Ava I fragment deletion from position 8842 to 10453.

Some E. coli cells transformed with the Ava I digested pARC376 plasmid were found to have impaired lycopene cyclase gene function, and therefore, accumulated lycopene. These results indicated that the gene for lycopene cyclase was present in the region near the Sal I site at 9340.

b. Plasmid pARC1009

Example 10b describes the construction of plasmid pARC137B, whose Erwinia herbicola DNA insert is diagrammatically illustrated below.

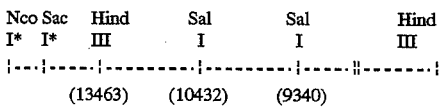

The Nco I and Sal I sites in the above diagram with asterisks are in the polylinker portion of parent plasmid pARC306A.

Plasmid pARC137B was digested with Sal I and then the region from the polylinker Sal I site to the Sal I site at about original position 9340 was ligated back together, to form plasmid pARC137-5. A Sal I-Sal I fragment of about 4123 bp was thereby removed. The formed plasmid pARC137-5 retained the Rec 7 promoter that was now adjacent to the

*Erwinia herbicola* DNA beginning at about the Sal I site at about original position 9340.

The resulting plasmid also contained two Stu I restriction sites between the remaining Sal I and Hind III sites. Those Stu I sites were at about original positions 7306 and 3538.

Digestion of plasmid pARC137-5 with Stu I, and religation of the Stu I-terminated fragments containing the above-illustrated Nco I and Hind III sites resulted in a new plasmid named pARC1009. That plasmid contained *Erwinia herbicola* DNA of interest from the Sal I site originally at about position 9340 to the Stu I site originally at about position 7306, and the Rec 7 promoter adjacent to that Sal I site.

Plasmid pARC1009 was transformed into *E. coli*, strain JM101, and the cells were grown and treated with nalidixic acid to induce the Rec 7 promoter. The protein fraction was isolated, analyzed on PAGE and a dominant protein band of 36 kilodaltons was noted. This protein band was identified as the enzyme lycopene cyclase, as discussed hereinafter. The protein band was isolated and subjected to N-terminal amino acid sequencing. The first 25 N-terminal amino acid residues were determined as shown in FIG. 19.

Comparison of the N-terminal amino acid sequence of the lycopene cyclase enzyme with the DNA sequence of the pARC376 plasmid revealed the position of the initiation codon of the lycopene cyclase gene. Surprisingly, the initiation codon is GTG, not the much more common ATG. A GTG codon normally codes for the amino acid valine, but under rare instances in bacteria, it can also code for methionine when it is the first amino acid in a protein (G. D. Stormo, 1986, in *Maximizing Gene Expression*, W. Reznikoff, L. Gold (Eds) Butterworths, Stoneham, Mass., pp 195–224.) Thus, from this comparison, the 5' end of the gene for lycopene cyclase was found to begin about 338 bp downstream from the Sal I site at original position 9340.

c. Plasmid pARC465

A series of studies was performed to determine the location of the 3' end of the gene. A plasmid, pARC465, which contains the carotenoid genes for GGPP synthase, phytoene synthase, phytoene dehydrogenase-4H and the chloramphenicol acetyltransferase gene that confers resistance to the antibiotic chloramphenicol, was constructed as follows.

The plasmid pARC307D is an analogous plasmid to the plasmid pUC8, except that plasmid. pARC307D contains the chloramphenicol acetyltransferase gene instead of the ampicillinase gene. Plasmid pARC307D also contains the same polycloning linker as plasmid pUC8.

Plasmid pARC307D was digested with Hind III and Eco RI. The plasmid pARC376-Ava 102 (Example 11b) was also digested with Hind III and Eco RI. The resultant about 8000 bp fragment from Hind III (13463) to Eco RI (3370) of plasmid pARC376-Ava 102 Was isolated from an agarose gel (the fragment size is only about 8000 bp because the Ava I deletions in plasmid pARC376-Ava 102 described before deleted about 2200 bp from the parent pARC376 plasmid). This about 8000 bp Hind III-Eco RI fragment was cloned into the Hind III- and Eco RI-digested plasmid pARC307D. The resulting plasmid, pARC465, caused the production of lycopene when transformed into *E. coli*, and also conferred resistance to the antibiotic chloramphenicol.

The plasmid pARC1009, which contains the gene for lycopene cyclase, was introduced into *E. coli* cells containing plasmid pARC465, and the cells were grown on chloramphenicol and ampicillin. These cells produced beta-carotene. This indicated that the 3' end of the gene for lycopene cyclase was upstream from the Stu I site (original position about 7306).

d. Plasmid pARC1008

To further define the location of the 3' end of the gene, the 1548 bp Sal I (9340) to Pst I (7792) DNA fragment (Example 17a) was cloned into plasmid pARC306A. The resulting plasmid, pARC1008, was introduced into *E. coli* cells that already contained plasmid pARC465. These cells, grown in the presence of chloramphenicol and ampicillin, produced beta-carotene. These results indicated that the 3' end of the gene was present upstream from the Pst I (7792) site.

In summary then, the gene for lycopene cyclase is contained in an about 1548 bp Sal I to Pst I fragment of plasmid pARC376. The actual initiation codon is about 338 bp downstream from the Sal I site. Therefore, the bounds of the gene for lycopene cyclase are approximately from position 9002 to the Pst I site at position 7792 in FIG. 5, enclosing an approximately 1210 bp DNA segment. FIG. 19 contains the nucleotide sequence obtained and an amino acid sequence for lycopene cyclase.

Several constructs have been made in which the 5' end of the gene for lycopene cyclase has been modified. Two are described below.

e. Plasmid pARC147

In one construct, the initiation codon was changed from a GTG sequence to an ATG sequence by introducing a Nco I site by in vitro mutagenesis at the beginning of the gene as follows. An oligonucleotide probe was synthesized that had the following sequence as compared with the normal sequence:

Native DNA Sequence
\*Met
A GAG CGT ATC GTG AGG GAT CTG ATT TTA GTC GGC G
(SEQ ID NO:74)

New DNA Sequence
<u>Nco I</u>
G CGC GGA T<u>CC ATG G</u>GG GAT CTG ATT TTA GTC GGC G
 \*Met          (SEQ ID NO:75)
\*Initiation Methionine; bold-faced letters are as described before.

The Nco I restriction site sequence is CC ATGG, therefore, the new sequence at the initiation methionine introduced an Nco I site.

This new DNA sequence also altered the amino acid sequence at the NH$_2$ terminus of the proteins.

Native Amino Acid Sequence
Met Arg Asp Leu Ile  Leu Val  Gly Gly Gly
(SEQ ID NO:76)

New Amino Acid Sequence
Met Gly Asp Leu Ile  Leu Val  Gly Gly Gly
(SEQ ID NO:77)

This newly modified, variant lycopene cyclase gene, starting at the introduced Nco I site was cloned into the plasmid pARC306A to generate the plasmid pARC147. Plasmid pARC147 was introduced into *E. coli* cells already containing plasmid pARC465, and the cells were grown in the presence of chloramphenicol and ampicillin. These cells produced beta-carotene. Thus, a functional variant lycopene cyclase gene within an about 1210 bp DNA fragment from Nco I to Pst I that can be moved into other plasmids for the expression of the enzyme, was constructed.

f. Lycopene Cyclase Assay

Cultured *E. coli* cells separately transformed with plasmid pARC1606, described below, that cause lycopene accumulation in *E. coli*, and with plasmid pARC147, discussed before, that contains the Rec 7-driven lycopene cyclase gene were separately homogenized. The homogenates were mixed at a ratio of 1:1 in the presence of 2.5 mM $MgCl_2$, 3 mM $MnCl_2$, 4 mM dithiothreitol (DTT), and 6 mM ATP for six hours at 30° C.

The assay mixture was thereafter lyophilized and extracted with acetone:methanol (7:2, v:v). The extract was concentrated and analyzed by HPLC. β-Carotene was detected; about 54 ng of the cis isomer and about 27 ng of the trans isomer. Thus, the genetically engineered gene for lycopene cyclase present in plasmid pARC147, was actively transcribed by the transformed *E. coli* host cells.

Cofactors such as FAD, NADP and FMN are not required for lycopene cyclase activity. ATP is, however, essential for activity.

Construction of Plasmid pARC1606

The construction of plasmid pARC1606 proceeded with a series of intermediate vectors.

The plasmid pARC376 was partially digested with Bam HI and then religated. The religated plasmid was transformed into *E. coli* cells and cells were selected that contained a plasmid in which Bam HI fragments of about 1045 bp (from original position 3442 to 4482) and of about 815 bp (from original position 5302 to 4487) were deleted from the pARC376 plasmid. The name of the new plasmid was pARC376-Bam 100, and the presence of the plasmid caused the *E. coli* cells to produce β-carotene, since the gene for β-carotene hydroxylase was deleted.

The plasmid pARC376-Bam 100 was digested with Hind III and Eco RI. The fragment containing the *Erwinia herbicola* carotenoid genes was isolated and religated. The coordinates for the Hind III and Eco RI sites originally from plasmid pARC376 are 13463 and 3370, respectively.

Plasmid pARC307D, supra, also contains the pUC8 polycloning linker. Plasmid pARC307D was digested with Hind III and Eco RI, and the *Erwinia herbicola* Hind III and Eco RI fragment excised from plasmid pARC376-Bam 100 was cloned into plasmid pARC307D to form plasmid pARC279. This plasmid conferred chloramphenicol resistance to the *E. coli* cells and also caused them to produce β-carotene. The plasmid pARC279 contains about 11.7 kb.

Plasmid pARC279 was partially digested with Bgl II and Bam HI and then religated to delete specific regions from the pARC279 plasmid that were not necessary for β-carotene production and make the plasmid as small as possible. A clone was found in which the size of the plasmid was about 10 kb (about 1.7 kb had been deleted), that conferred chloramphenicol resistance to *E. coli* and caused the synthesis of β-carotene. That plasmid was named pARC281B.

Plasmid pARC1606 was made from pARC281B by mutagenizing *E. coli* cells that contained plasmid pARC281B with nitrosoguanidine (NTG) according to the following protocol.

The following is the NTG mutagenesis protocol:

1. *E. coli* cells containing plasmid pARC281B were grown to log phase—about $3-5\times10^8$ cells/ml or an absorbance of 0.3–0.6 at 600 mR.
2. The cells were washed twice with phosphate buffer (50 mM, pH 7.0), and then resuspended in 1/10th of the original volume of growth medium.
3. NTG was added to the cells in phosphate buffer to a final concentration of μg/ml. The cells were incubated for 1 hour at 37° C.
4. The cells were washed three times in phosphate buffer to remove the NTG. The cells were then resuspended in Luria-Broth with 25 μg/ml of chloramphenicol and grown for about 15–18 hours at 37° C.
5. The cells were then diluted and plated on Luria-Broth agar (1.5 percent agar) containing 25 μg/ml chloramphenicol. A colony was found that produced lycopene as evidenced by the red appearance of the colony. The plasmid contained in that colony was isolated and called pARC1606.

A mutation was induced somewhere in the gene for lycopene cyclase after the nitrosoguanidine treatment that caused the inactivation of the enzyme. This caused the cells to accumulate lycopene, the precursor to β-carotene. Cells that contained the plasmid with this mutation were now red, due to the accumulation of lycopene, instead of the β-carotene yellow color.

Cells containing plasmid pARC1606 were used as a source of lycopene for the lycopene cyclase assays described before.

g. Plasmid pARC1509

The new construct, plasmid pARC147, that works effectively in *E. coli*, is not effective in yeast. It appears that the second N-terminal amino acid, which was changed from Arg to Gly by the above procedure made this variant gene inactive in yeast. Therefore both 5' and 3' ends of the lycopene cyclase gene were genetically re-engineered to introduce a new 3' restriction site, and restore the second N-terminal amino acid to the native sequence. This new variant DNA was prepared as follows.

A Sph I restriction site at the initiation Met codon and a Bam HI restriction Site at the 3' end of the gene were introduced into the native sequence by PCR (as described before) using the following probes:

For the Sph I site at the 5' end

```
     Sph I
5' G CGG CGC ATG CGG GAT CTG ATT TTA GTC GGC G 3'
                    (SEQ ID NO:78)
```

For the Bam HI site at the 3' end

```
     Bam HI
5' CAT CGG ATC CTG TCA GGA AAA TGG TTC AGC 3'
                    (SEQ ID NO:79)
```

An about 3012 bp fragment from Sal I (9340) to the Nco I site (6342) was excised from the plasmid pARC271D described in Example 10c. This fragment was used as the template for the PCR reaction that was performed as described previously.

After PCR, the reaction mixture was digested with Sph I and Bam HI. The about 1142 bp fragment shown in FIG. 19, between the first G residue of the Sph I (about 18) site and the first G residue of the Bam HI (about 1168) site, was isolated on an agarose gel as previously described. This about 1142 bp Sph I-Bam HI fragment of the lycopene cyclase variant gene was cloned into pUC18 that had been previously digested with Sph I and Bam HI. The resulting plasmid was called pARC1509.

h. Plasmid pARC1510

To determine whether the genetically engineered version of the lycopene cyclase gene in pARC1509 codes for an active protein, the structural gene segment was introduced adjacent to the TAC promoter in the plasmid pKK223-3 (Pharmacia) as follows. Upstream from the Sph I site of plasmid pARC1509 (in the polycloning sequence) is a unique Hind III site. The plasmid pARC1509 was digested with Hind III and Bam HI, and an about 1156 bp Hind III-Bam HI fragment was isolated. The fragment ends were made blunt by treatment with the Klenow fragment of DNA Polymerase I.

The plasmid pKK223-3 contains a unique Eco RI site adjacent to the TAC promoter. Plasmid pKK223-3 was digested with Eco RI and the ends were likewise blunted with the Klenow reagent. The fragment containing the structural gene segment for lycopene cyclase was ligated into the blunted Eco RI site adjacent to the TAC promoter to produce the plasmid pARC1510.

To verify that the new variant gene for lycopene cyclase was capable of expressing an active protein, plasmid pARC1510 was introduced into E. coli cells that already contained the plasmid pARC465 that contains the CAT resistance gene and the genes necessary to produce colored lycopene, but from which the gene for lycopene cyclase had been deleted. E. coli cells containing both plasmids pARC465 and pARC1510, were grown with both chloramphenicol and ampicillin, and produced beta-carotene.

EXAMPLE 8

Beta-carotene production in E. coli a. Method One—Plasmid(s) containing engineered genes for GGPP synthase, phytoene synthase, phytoene dehydrogenase-4H and lycopene cyclase Four carotenoid enzyme genes are required to produce beta-carotene from ubiquitous precursors, i.e., the genes for GGPP synthase, phytoene synthase, phytoene dehydrogenase-4H, and lycopene cyclase. In one example, the first three genes; i.e., for GGPP synthase, phytoene synthase, and phytoene dehydrogenase-4H enzymes, were present on the plasmid pARC465. This plasmid also contains the chloramphenicol acetyltransferase gene that confers resistance to the antibiotic chloramphenicol in E. coli.

The plasmid pARC1009, described in Example 17, contains the about 2038 bp Sal I to Stu I DNA fragment inserted into plasmid pARC306A. When plasmid pARC1009 was transferred to E. coli cells that contained the plasmid pARC465, the cells produced beta-carotene at a level of about 0.05 percent (dry weight).

The plasmid pARC147, also described in Example 17, contains the about 1215 bp Nco I to Pst I fragment that was inserted into the pARC306A plasmid. This plasmid was also introduced into E. coli cells that contained the plasmid pARC465, and those cells also synthesized beta-carotene at a level of about 0.05 percent (dry weight). Because it was subsequently discovered that this variant of the lycopene cyclase structural gene was inactive in yeast, its use was discontinued and the gene was altered as described in Example 17 to produce plasmid pARC1510. Plasmid pARC1510, transferred in combination with plasmid pARC465, produced beta-carotene in E. coli.

b. Alternate Method—Plasmid pARC376 with a defective gene for beta-carotene hydroxylass The plasmid pARC376 has a sufficient gene complement to effectuate the synthesis of carotenoids up to and including zeaxanthin diglucoside in E. coli. Beta-carotene is the metabolic substrate for the beta-carotene hydroxylase enzyme that adds two hydroxyl groups at the 3 and 3' positions of beta-carotene to produce zeaxanthin. If the gene for beta-carotene hydroxylase is deleted, mutated, or in some other way made non-functional, the cells accumulate the substrate beta-carotene.

i. Plasmid pARC376-Pst 102

The gene for beta-carotene hydroxylase is contained on a 975 bp DNA fragment bounded by a Pst I site (4886) and the Sma I site (5861) in plasmid pARC376. To delete part of the gene for this enzyme, plasmid pARC376 was partially digested with Pst I, and the appropriate cut ends were religated. Analysis of the plasmid DNA determined that the 392 bp Pst I fragment from original position 4886 to 5215 was deleted. This plasmid was named pARC376-Pst 102.

After transformation of plasmid pARC376-Pst 102 into E. coli, colonies with an orange-yellow color were picked and analyzed for carotenoid content by methods described before. The normal color of E. coli colonies containing the intact pARC376 plasmid and producing zeaxanthin diglucoside is yellow. Analysis of the orange-yellow colored colonies revealed that only beta-carotene was being produced at a level of about 0.1 percent (dry weight).

ii. Plasmid pARC376-Bam 100

In an analogous procedure, plasmid pARC376 was partially digested with Bam HI and appropriately religated, causing the deletion of an approximately 815 bp fragment from about original position 4487 to 5302. The resultant plasmid was called pARC376-Bam 100. The plasmid DNA was transformed into E. coli HB101, and orange-yellow colonies were selected and analyzed for carotenoid content. Beta-carotene accumulated in these cells at a level of about 0.1 percent.

EXAMPLE 19

Production of beta-carotene in S. cerevisiae

The structural gene for each of the four enzymes required for beta-carotene synthesis is placed adjacent to an appropriate promoter and termination sequence that will properly function in S. cerevisiae. Appropriate promoters include the GAL 1 and GAL 10 divergent promoters, described in the Detailed Description and Example 6, and the phosphoglyceric acid kinase gene promoter (PGK), likewise described. An appropriate terminator is the termination sequence from the pGK gene.

The structural genes for GGPP synthase and phytoene synthase are present in the plasmid pARC145G, adjacent to the GAL 10 and GAL 1 promoters as described in Example 6. The termination sequence from the PGK gene is at the 3' end of the gene for phytoene synthase. To produce beta-carotene it was necessary to introduce the genes for phytoene dehydrogenase-4H and lycopene cyclase in vectors that direct the expression of these genes in this microorganism.

One approach to induce beta-carotene synthesis in yeast is to insert these two genes into a vector, such as plasmid pARC146, that contains the GAL 10 and GAL 1 divergent promoters and introduce the resultant plasmid into S. cerevisiae that already contains plasmid pARC145G. The resulting population has all of the genetic material required to produce beta-carotene in a form that permits high level expression of the genes.

a. Plasmid pARC1520

The plasmid pARC146D (Example 12) already contains the gene for phytoene dehydrogenase-4H adjacent to the GAL 1 promoter. The structural gene for lycopene cyclase described in Example 17 was cloned into plasmid pARC146D adjacent to the GAL 10 promoter as follows:

The plasmid pARC1509, described in Example 17, was digested with Hind III and Bam HI. The about 1156 bp fragment containing the structural gene for lycopene cyclase was isolated and the ends were blunted by treatment with the Klenow fragment of DNA Polymerase I.

Plasmid pARC146D was digested with Eco RI (restriction site is unique in plasmid pARC146D—see FIG. 14). The ends of the Eco RI digested plasmid were also blunted and the lycopene cyclase gene was cloned into plasmid pARC146D to produce the plasmid pARC1520. Plasmid pARC1520, therefore, contains the gene for phytoene dehydrogenase-4H adjacent to the GAL 1 promoter, the gene for lycopene cyclase adjacent to the GAL 10 promoter, and the URA 3 gene (described before) useful for selection in yeast. Plasmid pARC1520 was introduced into the S. cerevisiae, strain YPH499, which already contained the plasmid pARC145G. Beta-carotene was produced at the level of about 0.01 percent of the dry weight.

EXAMPLE 20

Production of Increased Levels of Carotenoids in Higher Plants.

a. Chloroplast

Although beta-carotene is synthesized in the chloroplasts of plants, most higher plant species do not accumulate very high levels of it. Carrot roots are among the best accumulators, but even in these the concentration is only about 0.01–0.1 percent (dry weight). The objective, then, is to increase the catalytic activity of lycopene cyclase and thereby the accumulation of beta-carotene.

Lycopene production is thought to be the divergence point of carotenoid synthesis. In one branch, lycopene is converted to alpha-carotene that in turn is converted to lutein. Lutein is the carotenoid that accumulates in plants to the highest concentration level of all carotenoids. In the other branch, lycopene is converted to beta-carotene, which does not accumulate to as high a level as lutein. If the level for the enzyme for lycopene cyclase is increased, however, beta-carotene accumulates to higher levels.

To increase the level of lycopene cyclase in the chloroplast, the following steps were taken. Plasmid pARC1509 (Example 17) was digested with Sph I and Bam HI. The resulting approximately 1142 bp Sph I-Bam HI fragment was cloned into the Sph I and Bam HI sites of plasmid pATC212, discussed in Example 3, to produce plasmid pARC1511.

Plasmid pARC1511 was digested with Xba I, generating a Xba I fragment of approximately 2069 bp that contained the 35S promoter, the transit peptide sequence, the lycopene cyclase gene, and the NOS polyadenylation sequence. This Xba I fragment was cloned into the Xba I site of plasmid pGA482 (Pharmacia). The resulting plant-transforming plasmid was named pARC1512.

The relevant features of plasmid pGA482 were described previously and include (i) the left and right borders of the T-DNA sequence, which directs the integration of the DNA sequences between these borders into the plant genome; (ii) the kanamycin resistance gene using the NOS promoter for expression, which allows the selection of kanamycin resistant plants containing the lycopene cyclase gene; and (iii) an origin of replication that allows the replication of plasmid pGA482 in Agrobacterium tumefaciens.

Plasmid pARC1512 was transformed into Agrobacterium tumefaciens LBA4404 (Clontech, Inc.) according to standard protocols. Agrobacterium cells containing the plasmid pARC1512 with the lycopene cyclase gene construct was transferred by infection of tobacco leaf discs using the method of Horsch et al., Science, 227:1229–1231 (1985). During the infection process, the entire DNA segment between the left and right borders of the pGA482 plasmid is transfected into plant cells. Transfected plant cells were selected for kanamycin resistance.

The level of total carotenoids in the resulting kanamycin-resistant transgenic plants was examined. Some transgenic tobacco plants transformed with plasmid pARC1512 contained total carotenoid levels two to three times higher than wild type, untransformed tobacco plants.

Other carotenoid enzyme-specific genes can also be utilized in conjunction with the lycopene cyclase gene to increase the production and accumulation of beta-carotene. These include genes for GGPP synthase, phytoene synthase, and phytoene dehydrogenase-4H. The introduction of these genes into higher plants involves the same manipulations as described above for lycopene cyclase. The genes are attached to the tobacco transit peptide DNA sequence and are then placed adjacent to a functional plant promoter, such as the CaMV 35S promoter. Also placed adjacent, is a polyadenylation sequence, such as the NOS polyadenylation sequence.

These gene constructs are introduced into plants along with the gene for lycopene cyclase, and the combination results in increased total enzyme activity in this portion of the carotenoid synthesis pathway. This further results in an increase of beta-carotene synthesis and accumulation in the chloroplast.

b. Cytoplasm

Introducing Erwinia herbicola genes for GGPP synthase, phytoene synthase, phytoene dehydrogenase-4H, and lycopene cyclase results in beta-carotene synthesis in the cytoplasm. In order to express these enzymes in plant cells, the structural genes are individually cloned into one or more vectors that contain a promoter and a polyadenylation sequence that will function in plants. One such vector is the before-described pCaMVCN, with the CaMV 35S promoter and the NOS polyadenylation sequence. The four genes with the appropriate promoters and polyadenylation signals are then inserted into the before-described plasmid, pGA482.

Plasmid pGA482, containing the four carotenoid-specific genes with the appropriate regulatory signals, is transformed into A. tumefaciens, such as strain A281. Subsequently, plants such as tobacco and alfalfa are infected with the A. tumefaciens, containing the four carotenoid genes, during which process, the carotenoid genes are transfected and integrated into the plant genome. The result is that the transformed plants have the necessary genes, and the capacity to produce and accumulate beta-carotene in the cytoplasm. The CaMV 35S promoter causes the carotenoid genes to be expressed.

EXAMPLE 21

β-Carotene Production in Pichia pastoris

The before-described method is also extendable to other yeasts. One yeast system that serves as an example is the methylotrophic yeast, Pichia pastoris.

To produce β-carotene in P. pastoris, structural genes for GGPP synthase, phytoene synthase, phytoene dehydrogenase-4H and lycopene cyclase are placed under the control of regulatory sequences that direct expression of structural genes in Pichia. The resultant expression-competent forms of those genes are introduced into Pichia cells.

For example, the transformation and expression system described by Cregg et al., *Biotechnology* 5:479–485 (1987); *Molecular and Cellular Biology* 12:3376–3385 (1987) can be used. A structural gene for GGPP synthase such as that from plasmid pARC489D is placed downstream from the alcohol oxidase gene (AOX1) promoter and upstream from the transcription terminator sequence of the same AOX1 gene. Similarly, structural genes for phytoene synthase, phytoene dehydrogenase-4H, and lycopene cyclase such as those from plasmids pARC140N, pARC146D and pARC1509, respectively, are placed between AOX1 promoters and terminators. All four of these genes and their flanking regulatory regions are then introduced into a plasmid that carries both the *P. pastoris* HIS4 gene and a *P. pastoris* ARS sequence (Autonomously Replicating Sequence), which permit plasmid replication within *P. pastoris* cells [Cregg et al., *Molecular and Cellular Biology*, 12:3376–3385 (1987)].

The vector also contains appropriate portions of a plasmid such as plasmid pBR322 to permit growth of the plasmid in *E. coli* cells. The final resultant plasmid carrying GGPP synthase, phytoene synthase, phytoene dehydrogenase-4H and lycopene cyclase genes, as well as the various additional elements described above, is illustratively transformed into a his4 mutant of *P. pastoris*, i.e. cells of a strain lacking a functional histidinol dehydrogenase gene.

After selecting transformant colonies on media lacking histidine, cells are grown on media lacking histidine, but containing methanol as described by Cregg et al., *Molecular and Cellular Biology*, 12:3376–3385 (1987), to induce the AOX1 promoters. The induced AOX1 promoters cause expression of the enzymes GGPP synthase, phytoene synthase, phytoene dehydrogenase-4H and lycopene cyclase and the production of β-carotene in *P. pastoris*.

The four genes for GGPP synthase, phytoene synthase, phytoene dehydrogenase-4H, and lycopene cyclase can also be introduced by integrative transformation, which does not require the use of an ARS sequence, as described by Cregg et al., *Molecular and Cellular Biology*, 12:3376–3385 (1987).

EXAMPLE 22

β-Carotene Production in *A. nidulans*

The genes encoding GGPP synthase, phytoene synthase, phytoene dehydrogenase-4H and lycopene cyclase as discussed before can be used to synthesize and accumulate β-carotene in fungi such as *Aspergillus nidulans*. Genes are transferred to Aspergillus by integration.

For example, the structural gene for GGPP synthase is introduced into the *E. coli* plasmid pBR322. The promoter from a cloned Aspergillus gene such as argB [Upshall et al., *Mol. Gen. Genet.* 204:349–354 (1986)] is placed into the plasmid adjacent to the GGPP synthase structural gene. Thus, the GGPP synthase gene is now under the control of the Aspergillus argB promoter.

Next, the entire cloned amds gene [Corrick et al., *Gene* 53:63–71 (1987)] is introduced into the plasmid. The presence of the amds gene permits acetamide to be used as a sole carbon or nitrogen source, thus providing a means for selecting those Aspergillus cells that have become stably transformed with the amds-containing plasmid.

Thus, the plasmid so prepared contains the Aspergillus argB promoter fused to the GGPP synthase gene and the amds gene present for selection of Aspergillus transformants. Aspergillus is then transformed with this plasmid according to the method of Ballance et al., *Biochem. Biophys. Res. Commun.* 112:284–289 (1983).

The phytoene synthase, phytoene dehydrogenase-4H and lycopene cyclase structural genes are each similarly introduced into the *E. coli* plasmid pBR322. Promoters for the cloned Aspergillus argB gene [Upshall et al., *Mol. Gen. Genet*, 204:349–354 (1986)] are placed immediately adjacent to those three structural genes. Thus, these structural genes are controlled by the Aspergillus argB promoters.

The entire, cloned Aspergillus trpC gene [Hamer and Timberlake, *Mol. Cell. Biol.*, 7:2352–2359 (1987)] is introduced into the plasmid. The trpC gene permits selection of the integrated plasmid by virtue of permitting transformed trpC mutant Aspergillus cells to now grow in the absence of tryptophan. The Aspergillus strain, already transformed with the plasmid containing the GGPP synthase gene, is now capable of synthesizing β-carotene.

Although the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

---

What is claimed is:

1. A purified and isolated DNA segment comprising a nucleotide sequence that contains at least 1125 base pairs that define the structural gene for the *Erwinia herbicola* enzyme lycopene cyclase that is present in a restriction endonuclease fragment comprising the approximately 1142 base pair Sph I-Bam HI restriction fragment of plasmid pARC1509, the approximately 1210 base pair Nco I-Pst I fragment of plasmid pARC147 or the approximately 1148 base pair fragment of plasmid pARC1520, said lycopene cyclase converting lycopene into beta-carotene.

2. A purified and isolated DNA segment comprising a nucleotide sequence that contains at least 1125 base pairs that define a structural gene for the *Erwinia herbicola* enzyme lycopene cyclase that is present in a plasmid selected from the group consisting of pARC1509, pARC147, pARC1520, pARC1512 or a DNA variant that has at least 80 percent identity to said gene and hybridizes with said gene under moderately high stringency conditions comprising hybridization at a temperature of about 50°–55° C. in 6XSSC and a final wash at a temperature of 68° C. in 1–3XSSC, said nucleotide sequence encoding an enzyme that converts lycopene into beta-carotene.

3. A recombinant DNA molecule comprising a vector operatively linked to an exogenous DNA segment that contains at least 1125 base pairs defining a structural gene for the *Erwinia herbicola* enzyme lycopene cyclase that is present in a plasmid selected from the group consisting of pARC1509, pARC147, pARC1520 and pARC1512 or a DNA variant that has at least 80 percent identity to said gene and hybridizes with said gene under moderately high stringency conditions comprising hybridization at a temperature of about 50°–55° C. in 6XSSC and a final wash at a temperature of 68° C. in 1–3XSSC, said nucleotide sequence encoding an enzyme that converts lycopene into beta-carotene, and a promoter for driving the expression of said enzyme in host organism cells.

4. The recombinant DNA molecule according to claim 3 wherein said host organism cells are of a prokaryote.

5. The recombinant DNA molecule according to claim 4 wherein said prokaryote cells are of *Escherichia coli*.

6. The recombinant DNA molecule according to claim 5 wherein said promoter is Rec 7.

7. The recombinant DNA molecule according to claim 4 wherein said prokaryote cells are of *Agribacterium tumefaciens*.

8. The recombinant DNA molecules according to claim 3 wherein said host organism cells are of a eukaryote.

9. The recombinant DNA molecule according to claim 8 wherein said eukaryote cells are of *Saccharomyces cerevisiae*.

10. The recombinant DNA molecule according to claim 9 wherein said promoter is the Gal 1 or Gal 10 promoter.

11. The recombinant DNA molecule according to claim 8 wherein said eukaryote host cells are of a higher plant.

12. A process for preparing the *Erwinia herbicola* enzyme lycopene cyclase comprising the steps of:
   (i) initiating a culture, in a nutrient medium, of procaryotic or eukaryotic host cells transformed with a recombinant DNA molecule as described in claim 3; and
   (ii) culturing the transformed host cells for a time period sufficient for said cells to express said lycopene cyclase protein molecule.

13. Plasmid pARC1510 having ATCC accession number 40851.

14. Plasmid pARC1520 having ATCC accession number 40852.

15. Plasmid pARC1509 having ATCC accession number 40850.

* * * * *

UNITED STATES PATENT AND TRADEMARK OFFICE
CERTIFICATE OF CORRECTION

PATENT NO.: 5,656,472

DATED: August 12, 1997

INVENTOR(S): Rodney L. Ausich, Friedhelm Luetke Brinkhaus, Indrani Mukharji, John Proffitt, James Yarger, Heui-Che Bill Yen It is certified that error appears in the above-identified patent and that said Letters Patent is hereby corrected as shown below:

| Col. | Line | |
|---|---|---|
| 5 | 30 | reads "ribulose his- "<br>should read --ribulose bis- -- |
| 8 | 46 | reads "an expressions control element"<br>should read --an expression control element-- |
| 9 | 13 | reads "progess as shown"<br>should read --process as shown-- |
| 21 | 27 | reads "*Proc. Natl. Acad. Sci. USA*, 82:58-24 (1985)"<br>should read --*Proc. Natl. Acad. Sci. USA*, 82:5824 (1985)-- |
| 24 | 15 | reads "includes the steps I of"<br>should read --includes the steps of-- |
| 25 | 41 | reads "art of carotenoid isblation."<br>should read --art of carotenoid isolation.-- |
| 33 | 24 | reads "region from pUC1S,"<br>should read --region from pUC18,-- |

UNITED STATES PATENT AND TRADEMARK OFFICE
CERTIFICATE OF CORRECTION

PATENT NO.: 5,656,472
DATED: August 12, 1997
INVENTOR(S): Rodney L. Ausich, Friedhelm Luetke Brinkhaus, Indrani Mukharji, John Proffitt, James Yarger, Heui-Che Bill Yen It is certified that error appears in the above-identified patent and that said Letters Patent is hereby corrected as shown below:

| Col. | Line | |
|---|---|---|
| 37 | 44 | (Table 3 A) reads "KH$_4$Cl" should read --NH$_4$Cl-- |
| 38 | 39 | reads "to form a cell peliet." should read --to form a cell pellet.-- |
| 44 | 51 | reads "ii. pATe212" should read --ii. pATC212-- |
| 47 | 14 | reads "Bam MI" should read --Bam HI-- |
| 47 | 21 | reads "Mind III site" should read --Hind III site-- |
| 48 | 16 | reads "approximately 2bp" should read --approximately 1112 bp-- |
| 52 | 6 | reads "the fused TRPi" should read --the fused TRP1-- |
| 54 | 1-7 | (Table) delete, is repeated previously in Column 53 |

UNITED STATES PATENT AND TRADEMARK OFFICE
CERTIFICATE OF CORRECTION

Page 3 of 4

PATENT NO.: 5,656,472
DATED: August 12, 1997
INVENTOR(S): Rodney L. Ausich, Friedhelm Luetke Brinkhaus, Indrani Mukharji, John Proffitt, James Yarger, Heui-Che Bill Yen It is certified that error appears in the above-identified patent and that said Letters Patent is hereby corrected as shown below:

| Col. | Line | |
|---|---|---|
| 54 | 17 | reads "* Dropout Mixtures" cut and move to Column 53, Line 58 immediately below "720 mg/l Dropout Mixture*" |
| 56 | 16 | reads "5' TCG CAT GCG" should read --5' TCG CAT GCG-- (2nd & 3rd "C" bold) |
| 64 | 39 | reads "GALI promoter" should read --GAL 1 promoter-- |
| 65 | 55 | reads "about 3.035 bp fragment" should read --about 3035 bp fragment-- |
| 67 | 34 | reads "to the GALI promoter" should read --to the GAL 1 promoter-- |
| 70 | 41 | reads "the same UV-V is spectra" should read --the same UV-Vis spectra-- |
| 72 | 17 | reads "Aspergillus cell Go now grow" should read --Aspergillus cell to now grow-- |
| 76 | 42 | reads "G CGC GGA" should read --G CGC GGA-- (1st & 2nd "C" bold) |

UNITED STATES PATENT AND TRADEMARK OFFICE
CERTIFICATE OF CORRECTION

PATENT NO.: 5,656,472

DATED: August 12, 1997

INVENTOR(S): Rodney L. Ausich, Friedhelm Luetke Brinkhaus, Indrani Mukharji, John Proffitt, James Yarger, Heui-Che Bill Yen It is certified that error appears in the above-identified patent and that said Letters Patent is hereby corrected as shown below:

Patent reads:

| Col. | Line | |
|------|------|---|
| 77 | 64 | reads "absorbance of 0.3-0.6 mR." should read --absorbance of 0.3-0.6 nm.-- |
| 78 | 2 | reads "final concentration of µg/ml." should read --final concentration of 100 µg/ml.-- |

Signed and Sealed this

Twenty-ninth Day of December, 1998

Attest:

BRUCE LEHMAN

Attesting Officer   Commissioner of Patents and Trademarks